US011249069B2

(12) United States Patent
Sakairi et al.

(10) Patent No.: US 11,249,069 B2
(45) Date of Patent: Feb. 15, 2022

(54) CANCER ANALYSIS SYSTEM AND CANCER ANALYSIS METHOD

(71) Applicant: Hirotsu Bio Science Inc., Tokyo (JP)

(72) Inventors: Minoru Sakairi, Tokyo (JP); Masakazu Sugaya, Tokyo (JP); Koichi Terada, Tokyo (JP); Taku Nakamura, Tokyo (JP); Norihito Kuno, Tokyo (JP)

(73) Assignee: Hirotsu Bio Science Inc.

( * ) Notice: Subject to any disclaimer, the term of this patent is extended or adjusted under 35 U.S.C. 154(b) by 450 days.

(21) Appl. No.: 15/767,244

(22) PCT Filed: Feb. 28, 2017

(86) PCT No.: PCT/JP2017/007964
§ 371 (c)(1),
(2) Date: Apr. 10, 2018

(87) PCT Pub. No.: WO2017/150569
PCT Pub. Date: Sep. 8, 2017

(65) Prior Publication Data
US 2019/0079071 A1 Mar. 14, 2019

(30) Foreign Application Priority Data
Feb. 29, 2016 (WO) .................. PCT/JP2016/056137

(51) Int. Cl.
*G01N 33/493* (2006.01)
*G01N 33/574* (2006.01)
*G01N 33/48* (2006.01)
*G01N 33/483* (2006.01)

(52) U.S. Cl.
CPC .......... *G01N 33/493* (2013.01); *G01N 33/48* (2013.01); *G01N 33/483* (2013.01); *G01N 33/57488* (2013.01); *G01N 2333/43534* (2013.01)

(58) Field of Classification Search
CPC .......... G01N 33/483; G01N 33/57488; G01N 33/48; G01N 2333/43534; G01N 33/493
See application file for complete search history.

(56) References Cited

U.S. PATENT DOCUMENTS

2005/0051723 A1* 3/2005 Neagle ................ G01N 21/253
250/306
2017/0016906 A1* 1/2017 Hirotsu ............ G01N 33/57488

FOREIGN PATENT DOCUMENTS

EP 3081935 A1 12/2014
WO 2015/088039 A1 6/2015

OTHER PUBLICATIONS

Osamu Ikegami, "Extraction of Characteristics of Behavior from Recorded Images of Locomotion of the Nematode", IEICE Technical Report, Nov. 20, 1996 (Nov. 20, 1996), vol. 96, No. 379, pp. 13 to 17, fig. 1 (English Abstract provided).

* cited by examiner

*Primary Examiner* — Rebecca M Fritchman
(74) *Attorney, Agent, or Firm* — Harness, Dickey & Pierce, P.L.C.

(57) ABSTRACT

A cancer analysis system includes, so as to perform an efficient image analysis in a cancer screening test using nematodes: a light source unit that irradiates a plate on which nematodes and a urine sample are plotted, from below; a photographing unit that takes an image of the plate irradiated by the light source unit; and an analyzer that analyzes the image taken by the photographing unit. The analyzer: couples a prescribed number of pixels in the image into a larger number of pixels thereof; and performs a chemotaxis assay of the nematodes based on a time variation of information on a luminous center of gravity of the image.

7 Claims, 38 Drawing Sheets

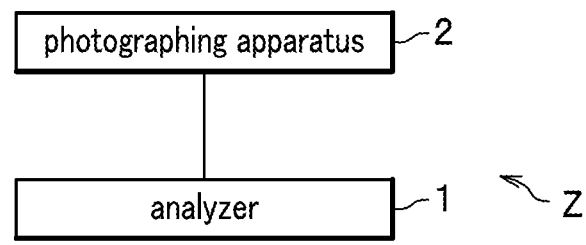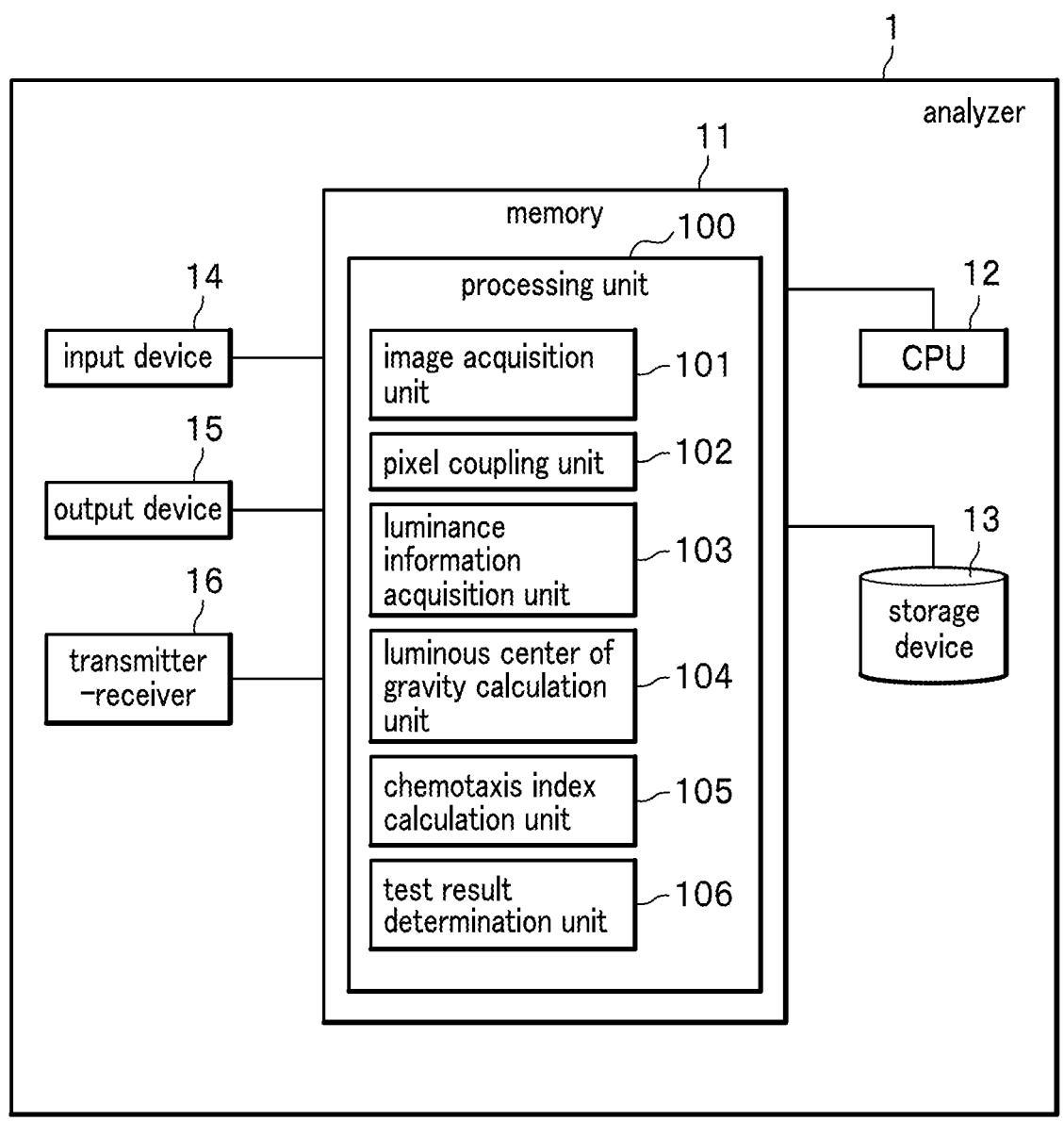

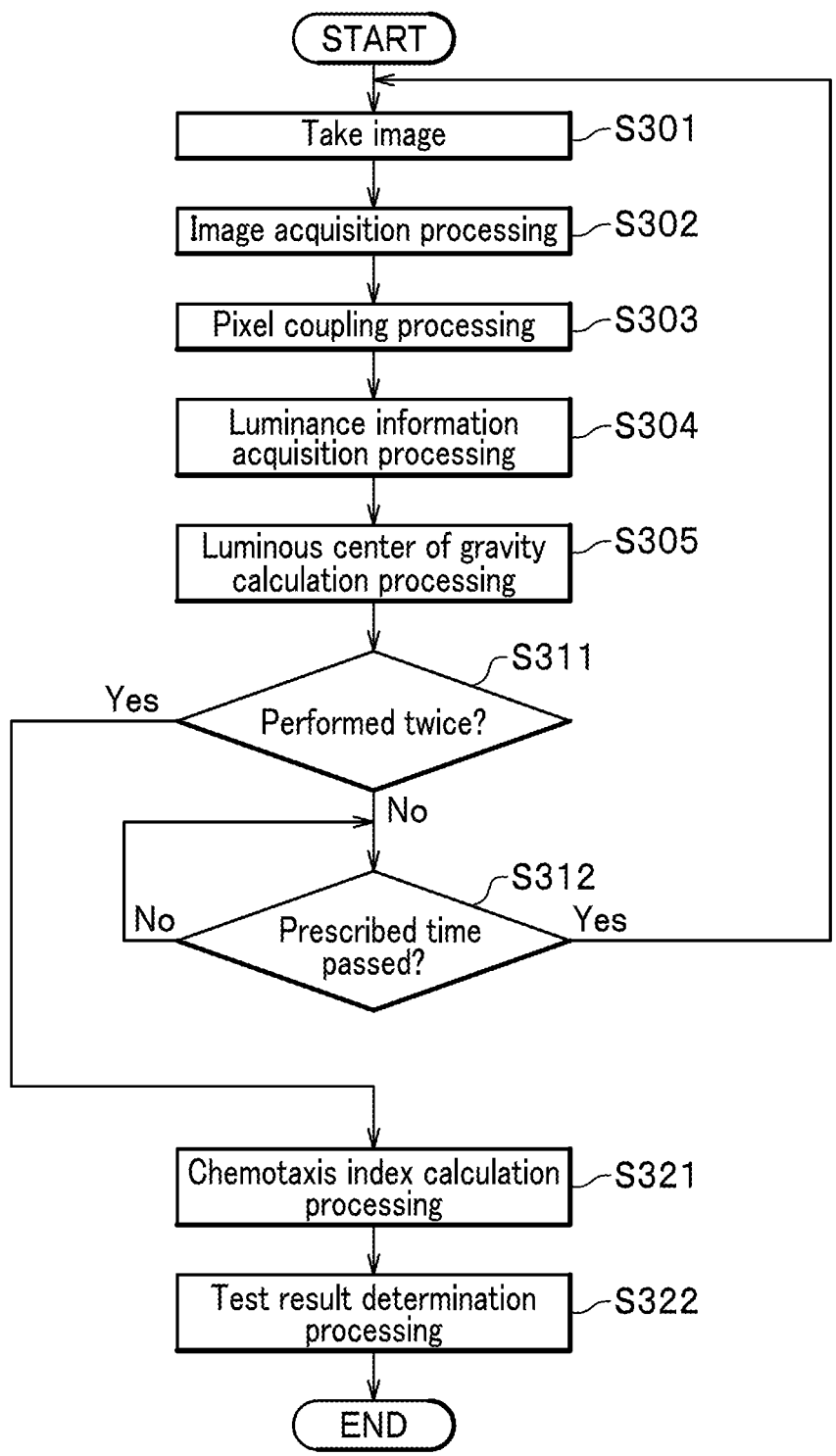

FIG.18A

Before processing

| | Center of Gravity Coordinate | | Change in Coordinates | |
|---|---|---|---|---|
| | X | Y | X | Y |
| immediately after | 0.40 | 0.24 | — | — |
| after 1 minute | 0.35 | 0.13 | -0.04 | -0.10 |
| after 2 minute | 0.54 | 0.28 | 0.15 | 0.05 |
| after 3 minute | 0.71 | -0.03 | 0.31 | -0.27 |
| after 4 minute | 0.90 | -0.46 | 0.50 | -0.70 |
| after 5 minute | 0.94 | -0.54 | 0.54 | -0.78 |
| after 6 minute | 0.83 | -0.70 | 0.43 | -0.93 |
| after 7 minute | 0.72 | -0.72 | 0.32 | -0.95 |
| after 8 minute | 0.86 | -0.86 | 0.46 | 1.10 |
| after 9 minute | 0.72 | -1.02 | 0.32 | -1.26 |
| after 10 minute | 1.10 | -0.91 | 0.70 | -1.15 |
| after 11 minute | 0.91 | -1.17 | 0.51 | -1.40 |
| after 12 minute | 1.01 | -0.93 | 0.61 | -1.17 |
| after 13 minute | 0.77 | -1.07 | 0.37 | -1.30 |
| after 14 minute | 1.05 | -1.09 | 0.65 | -1.32 |
| after 15 minute | 0.78 | -1.27 | 0.38 | -1.51 |

FIG.18B

Pixel removal of central area
(after 3 minutes onward, approx. 14mm)

| | Center of Gravity Coordinate | | Change in Coordinates | |
|---|---|---|---|---|
| | X | Y | X | Y |
| immediately after | 0.40 | 0.24 | — | — |
| after 1 minute | 0.35 | 0.13 | -0.04 | -0.10 |
| after 2 minute | 0.54 | 0.28 | 0.15 | 0.05 |
| after 3 minute | 1.20 | 0.22 | 0.80 | -0.01 |
| after 4 minute | 1.61 | 0.22 | 1.21 | -0.01 |
| after 5 minute | 1.50 | 0.07 | 1.10 | -0.16 |
| after 6 minute | 1.09 | -0.66 | 0.69 | -0.90 |
| after 7 minute | 1.07 | -0.50 | 0.68 | -0.73 |
| after 8 minute | 1.26 | -0.40 | 0.87 | -0.64 |
| after 9 minute | 0.86 | -0.94 | 0.46 | -1.17 |
| after 10 minute | 1.31 | -0.87 | 0.92 | -1.11 |
| after 11 minute | 1.00 | -0.86 | 0.60 | -1.09 |
| after 12 minute | 1.17 | -0.67 | 0.77 | -0.90 |
| after 13 minute | 0.92 | -0.96 | 0.52 | -1.20 |
| after 14 minute | 1.34 | -0.73 | 0.95 | -0.96 |
| after 15 minute | 0.97 | -0.92 | 0.57 | -1.15 |

FIG.19A
Before processing

| | Center of Gravity Coordinate | | Change in Coordinates | |
|---|---|---|---|---|
| | X | Y | X | Y |
| immediately after | 0.12 | 0.25 | — | — |
| after 1 minute | -0.18 | 0.23 | -0.30 | -0.02 |
| after 2 minute | -0.55 | 0.44 | -0.67 | 0.18 |
| after 3 minute | -1.06 | 0.42 | -1.18 | 0.17 |
| after 4 minute | -1.45 | 0.45 | -1.57 | 0.20 |
| after 5 minute | -1.68 | 0.22 | -1.80 | -0.04 |
| after 6 minute | -1.93 | 0.26 | -2.04 | 0.01 |
| after 7 minute | -2.09 | 0.09 | -2.20 | -0.16 |
| after 8 minute | -2.19 | 0.03 | -2.31 | -0.22 |
| after 9 minute | -2.18 | -0.05 | -2.30 | -0.30 |
| after 10 minute | -2.13 | 0.22 | -2.25 | -0.03 |
| after 11 minute | -1.98 | 0.01 | -2.10 | -0.25 |
| after 12 minute | -1.94 | 0.03 | -2.06 | -0.22 |
| after 13 minute | -1.66 | 0.07 | -1.78 | -0.18 |
| after 14 minute | -1.61 | -0.08 | -1.72 | -0.34 |
| after 15 minute | -1.31 | -0.16 | -1.43 | -0.42 |

FIG.19B
Pixel removal of central area
(after 3 minutes onward, approx. 14mm)

| | Center of Gravity Coordinate | | Change in Coordinates | |
|---|---|---|---|---|
| | X | Y | X | Y |
| immediately after | 0.12 | 0.25 | — | — |
| after 1 minute | -0.18 | 0.23 | -0.30 | -0.02 |
| after 2 minute | -0.55 | 0.44 | -0.67 | 0.18 |
| after 3 minute | -2.10 | 0.75 | -2.22 | 0.49 |
| after 4 minute | -2.32 | 0.32 | -2.44 | 0.06 |
| after 5 minute | -2.39 | 0.33 | -2.51 | 0.08 |
| after 6 minute | -2.49 | 0.15 | -2.61 | -0.10 |
| after 7 minute | -2.40 | 0.00 | -2.52 | -0.26 |
| after 8 minute | -2.43 | 0.01 | -2.54 | -0.25 |
| after 9 minute | -2.39 | -0.10 | -2.51 | -0.35 |
| after 10 minute | -2.37 | 0.04 | -2.49 | -0.21 |
| after 11 minute | -2.19 | -0.12 | -2.30 | -0.37 |
| after 12 minute | -2.27 | -0.15 | -2.39 | -0.40 |
| after 13 minute | -1.89 | 0.19 | -2.00 | -0.07 |
| after 14 minute | -1.82 | -0.04 | -1.94 | -0.30 |
| after 15 minute | -1.51 | -0.02 | -1.63 | -0.47 |

FIG.22

|  | Center of Gravity Coordinate | | Change in Coordinates | |
|---|---|---|---|---|
|  | X | Y | X | Y |
| immediately after | 0.40 | 0.24 | — | — |
| after 1 minute | 0.35 | 0.13 | −0.04 | −0.10 |
| after 2 minute | 0.54 | 0.28 | 0.15 | 0.05 |
| after 3 minute | 1.20 | 0.22 | 0.80 | −0.01 |
| after 4 minute | 1.61 | 0.22 | 1.21 | −0.01 |
| after 5 minute | 1.50 | 0.07 | 1.10 | −0.16 |
| after 6 minute | 1.09 | −0.66 | 0.69 | −0.90 |
| after 7 minute | 1.07 | −0.50 | 0.68 | −0.73 |
| after 8 minute | 1.26 | −0.40 | 0.87 | −0.64 |
| after 9 minute | 0.86 | −0.94 | 0.46 | −1.17 |
| after 10 minute | 1.31 | −0.87 | 0.92 | −1.11 |
| after 11 minute | 1.00 | −0.86 | 0.60 | −1.09 |
| after 12 minute | 1.17 | −0.67 | 0.77 | −0.90 |
| after 13 minute | 0.92 | −0.96 | 0.52 | −1.20 |
| after 14 minute | 1.34 | −0.73 | 0.95 | −0.96 |
| after 15 minute | 0.97 | −0.92 | 0.57 | −1.15 |

FIG.26

|  | Center of Gravity Coordinate | | Change in Coordinates | |
|---|---|---|---|---|
|  | X | Y | X | Y |
| immediately after | 0.12 | 0.25 | — | — |
| after 1 minute | −0.18 | 0.23 | −0.30 | −0.02 |
| after 2 minute | −0.55 | 0.44 | −0.67 | 0.18 |
| after 3 minute | −2.10 | 0.75 | −2.22 | 0.49 |
| after 4 minute | −2.32 | 0.32 | −2.44 | 0.06 |
| after 5 minute | −2.39 | 0.33 | −2.51 | 0.08 |
| after 6 minute | −2.49 | 0.15 | −2.61 | −0.10 |
| after 7 minute | −2.40 | 0.00 | −2.52 | −0.26 |
| after 8 minute | −2.43 | 0.01 | −2.54 | −0.25 |
| after 9 minute | −2.39 | −0.10 | −2.51 | −0.35 |
| after 10 minute | −2.37 | 0.04 | −2.49 | −0.21 |
| after 11 minute | −2.19 | −0.12 | −2.30 | −0.37 |
| after 12 minute | −2.27 | −0.15 | −2.39 | −0.40 |
| after 13 minute | −1.89 | 0.19 | −2.00 | −0.07 |
| after 14 minute | −1.82 | −0.04 | −1.94 | −0.30 |
| after 15 minute | −1.51 | −0.22 | −1.63 | −0.47 |

FIG.39

| 0 | 0 | 0 | 0 | 5 | 40 | 0 | 0 | 0 | 0 | 0 | 0 |
|---|---|---|---|---|---|---|---|---|---|---|---|
| 0 | 0 | 0 | 17 | 45 | 24 | 24 | 0 | 0 | 0 | 0 | 0 |
| 0 | 9 | 10 | 11 | 37 | 52 | 24 | 0 | 0 | 0 | 0 | 0 |
| 0 | 13 | 32 | 51 | 17 | 27 | 7 | 7 | 7 | 0 | 6 | 0 |
| 0 | 14 | 73 | 117 | 79 | 71 | 33 | 26 | 0 | 0 | 0 | 0 |
| 0 | 82 | 246 | 144 | 184 | 121 | 70 | 32 | 23 | 0 | 0 | 0 |
| 17 | 248 | 1390 | 161 | 103 | 25 | 13 | 22 | 39 | 6 | 25 | 37 |
| 0 | 90 | 63 | 175 | 27 | 21 | 28 | 41 | 24 | 17 | 0 | 0 |
| 11 | 136 | 122 | 54 | 19 | 26 | 18 | 0 | 8 | 0 | 0 | 0 |
| 0 | 41 | 64 | 0 | 13 | 0 | 0 | 0 | 0 | 0 | 0 | 0 |
| 0 | 0 | 20 | 0 | 0 | 0 | 0 | 0 | 0 | 0 | 0 | 0 |
| 0 | 0 | 0 | 0 | 0 | 0 | 2 | 0 | 0 | 0 | 0 | 0 |

Attraction

|  | 5 minutes | 10 minutes |
|---|---|---|
| Relative luminance number | 53% | 75% |
| Integrated value | 118% | 450% |

FIG.54

Repellent

|  | 5 minutes | 10 minutes |
|---|---|---|
| Relative luminance number | −26% | −28% |
| Integrated value | −78% | −221% |

CANCER ANALYSIS SYSTEM AND CANCER ANALYSIS METHOD

CROSS-REFERENCE TO RELATED APPLICATIONS

This application is a U.S. National Stage entry of PCT Application No: PCT/JP 2017/007964, filed on Feb. 28, 2017, and which application is incorporated herein by reference. To the extent appropriate, a claim of priority is made to the above disclosed application.

TECHNICAL FIELD

The present invention relates to techniques of a cancer analysis system and a cancer analysis method used for a cancer screening test using nematodes.

BACKGROUND ART

A cancer screening test has been proposed in which a finding that nematodes exhibit behavior of being attracted to urine of a cancer patient and behavior of being repelled from urine of a healthy subject is utilized.

International Application Publication WO 2015-088039 (to be referred to as Patent Document 1 hereinafter) discloses a cancer detection method using sense of smelling of nematodes.

In a currently-performed cancer screening test using nematodes, a tester plots nematodes with buffer on a plate (a petri dish), and spreads the plotted nematodes together with the buffer in a prescribed range. A taxis of the nematodes is then carried out, and the taxis-induced nematodes are counted, to thereby determine positivity or negativity for cancer. More specifically, the plate is divided into two areas by a center line thereof. When the nematodes migrate toward a specimen side, it is determined as a positive chemotaxis. When the nematodes migrate on a side opposite to the specimen, it is determined as a negative chemotaxis. Positivity and negativity is determined based on the above.

When an image analysis is introduced in a case as described above, there is an idea that the number of nematodes on the plate is counted by capturing features of forms of the nematodes. In this case, a process as follows is adopted.

(1) An industrial camera (50 to 100 million pixels) takes an image of an entire plate, and, in some cases, every one minute.

(2) A threshold of luminance is set based on the photographed image, and a binarization image is acquired.

(3) The number of nematodes is counted making use of the binarization image by which features of forms of the nematodes can be captured.

(4) In which position the counted nematodes are present on the plate is determined, and the number of the nematodes present in each of appropriately set areas thereon is further counted. A chemotaxis index is calculated based on the number of the further counted nematodes.

RELATED ART DOCUMENT

Patent Document

Patent Document 1: International Application Publication WO 2015-088039

SUMMARY OF THE INVENTION

Problems to be Solved by the Invention

The chemotaxis index can be calculated using the technique described above. The technique has, however, problems as follows.

(1) When nematodes are plotted on a plate, as described above, a tester plots the nematodes in a buffer solution on a plate and spreads out the plotted nematodes thereon. Such a spreading process is performed manually, and degrees of spreading are not always constant. Also, the spreading makes a two-dimensional breadth of the nematodes at a start of a taxis assay, which results in an unclear point of origin. Further, even if the point of origin is previously defined, because the spreading is performed manually as described above, the point of origin may be different each time different tests are carried out, and may thus become unclear. In the conventional technology, a chemotaxis index is calculated assuming that a center of a plate be a point of origin. A starting point of a chemotaxis assay may be, however, different each time chemotaxis assays are carried out. There is thus a problem in terms of accuracy in the assay in which the center of the plate is taken as the point of origin.

(2) When the number of nematodes is counted, it is required for storing a large volume of high-definition images. When a 10 million-pixel camera takes images at a frame rate of about 1 fps for about 30 minutes, a capacity may be as much as about 1G byte (some 2M byte per image).

(3) Counting the number of nematodes is not considered to fully use beneficial features of image processing. Further, an algorithm for removing nematodes in poor condition (nematodes slow in movement) becomes complicated.

(4) In counting the number of nematodes, it is often difficult to distinguish a nematode and noise such as dust. That is, there is a problem that dust may be counted as a nematode.

In light of the background described above, the present invention has been made in an attempt to perform an efficient image analysis in a cancer screening test using nematodes.

Means for Solving the Problem

A cancer analysis system includes: a light source unit that is configured to irradiate a plate on which nematodes and a urine sample are plotted, from below; a photographing unit that is configured to take an image irradiated by the light source unit; a quality control unit that is configured to output information on a quality state of the nematodes, based on the image taken by the photographing unit; and a chemotaxis index calculation unit that is configured to, after the quality control unit performs a quality control of the nematodes, perform a chemotaxis assay for calculating a chemotaxis index based on the image, the chemotaxis index being a degree of taxis of nematodes.

Another cancer analysis system includes: a light source unit that is configured to irradiate a plate on which nematodes and a urine sample are plotted, from below; a photographing unit that is configured to take an image irradiated by the light source unit; and an analysis unit that is configured to analyze the image taken by the photographing unit. The analysis unit performs a chemotaxis assay of the nematodes based on a time variation of information on luminance in the image.

Other means for solving the problems will be described in embodiments below.

Advantageous Effects of the Invention

In the present invention, in a cancer screening test using nematodes, an efficient image analysis can be performed.

BRIEF DESCRIPTION OF THE DRAWINGS

FIG. 1 is a functional block diagram illustrating a configuration of a cancer analysis system according to a first embodiment.

FIG. 2 is a functional block diagram illustrating a configuration of an analyzer according to the first embodiment.

FIG. 6A is a diagram illustrating a culture process, and FIG. 6B is a diagram illustrating a cancer screening test process.

FIG. 7 is a flowchart illustrating a procedure of a processing performed by the cancer analysis system used in the first embodiment.

FIGS. 18A and 18B are each a diagram illustrating a time variation in a center of gravity coordinate of a sample of a cancer patient by the minute and a change in coordinates by the minute. FIG. 18A illustrates a case where the pixel removal processing has not yet been performed (before processing). FIG. 18B illustrates a case where the pixel removal processing has already been performed.

FIGS. 19A and 19B are each a diagram illustrating a time variation of a center of gravity coordinate of a healthy subject by the minute and a change in coordinates by the minute. FIG. 19A illustrates a case where the pixel removal processing has not yet been performed (before processing). FIG. 19B illustrates a case where the pixel removal processing has already been performed.

FIG. 22 is a table showing a time variation of a luminous center of gravity in a case where urine of a cancer patient is used as a sample.

FIG. 26 is a table showing a time variation of a luminous center of gravity in a case where urine of a healthy subject is used as a sample.

FIG. 39 is a diagram illustrating a relationship between the actually acquired luminance information, the second quality control area, and the chemotaxis assay area.

FIG. 53 is a table showing an example (attraction) of relative luminance numbers without integration and relative luminance numbers with integration (cumulative addition) of relative luminance numbers (integrated values) every one minute.

FIG. 54 is a table showing an example (repellent) of relative luminance numbers without integration and relative luminance numbers with integration (cumulative addition) of relative luminance numbers (integrated values) every one minute.

EMBODIMENTS FOR CARRYING OUT THE INVENTION

Figure 3:
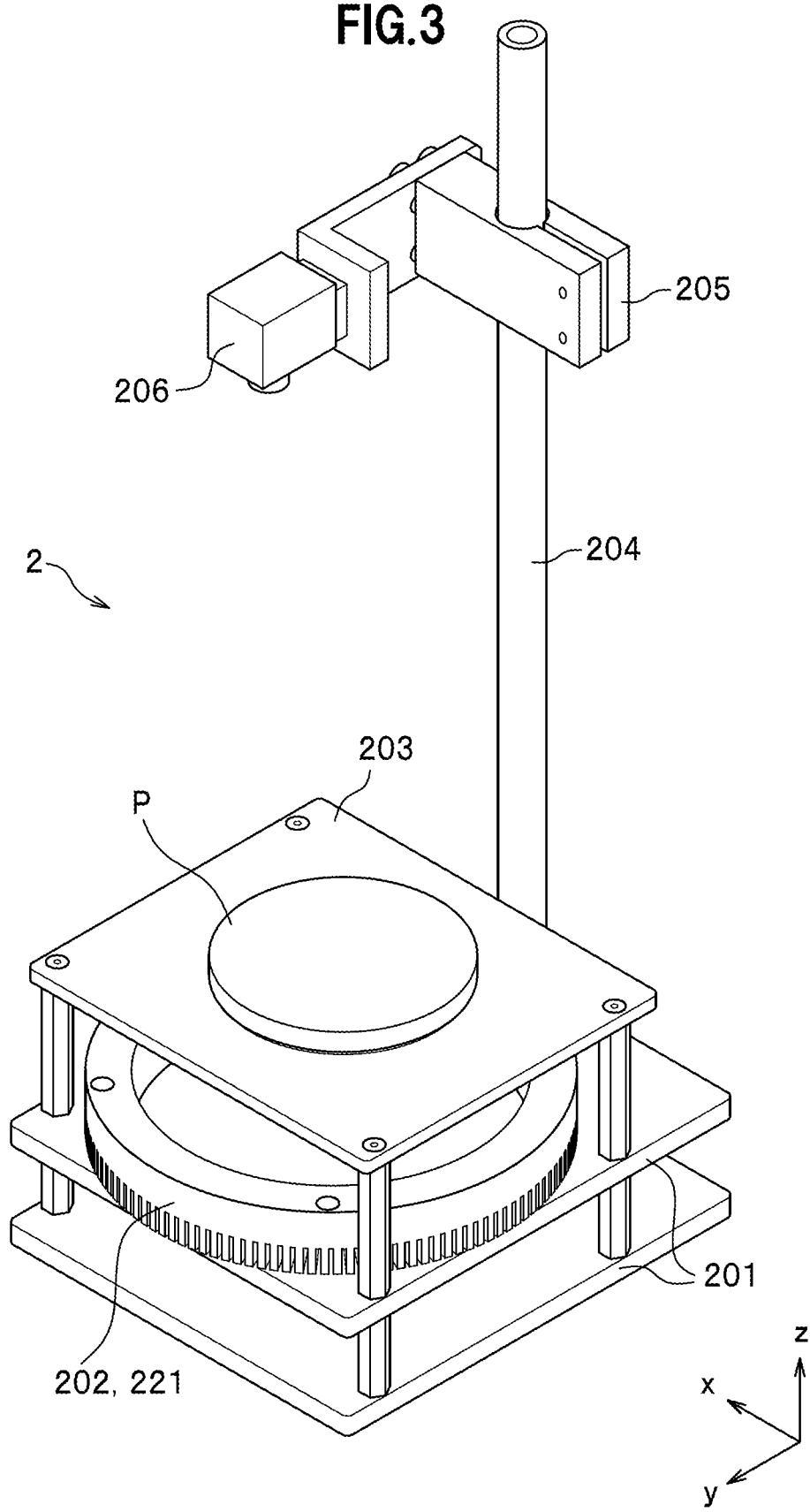
FIG. 3 is an external perspective diagram illustrating a photographing apparatus used in the first embodiment.

Next are described in detail embodiments for carrying out the present invention with reference to the related drawings. In the drawings, same reference numerals are given to similar components, and description thereof is omitted herefrom.

First Embodiment

[System Configuration]

FIG. 1 is a functional block diagram illustrating a configuration of a cancer analysis system according to a first embodiment of the present invention.

A cancer analysis system Z includes an analyzer (analysis unit) 1 and a photographing apparatus (photographing unit) 2.

The photographing apparatus 2: takes a photograph of a plate on which a nematode and a urine sample are plotted; and sends the photographed image to the analyzer 1.

The analyzer 1: acquires information on luminance, based on the image transmitted from the photographing apparatus 2; calculates a chemotaxis index of the nematodes, based on the acquired luminance information; and determines positivity or negativity for cancer, based on the calculated chemotaxis index.

[Analyzer]

FIG. 2 is a functional block diagram illustrating a configuration of the analyzer according to the first embodiment.

The analyzer 1: is realized by a PC (Personal Computer) or the like; and includes a memory 11, a CPU (Central Processing Unit) 12, a storage device 13, an input device 14, an output device 15, and a transmitter-receiver 16.

A program stored in the storage device 13 is loaded into the memory 11, and execution of the loaded program by the CPU 12 realizes a processing unit 100. The execution also realizes an image acquisition unit 101, a pixel coupling unit 102, a luminance information acquisition unit 103, a luminous center of gravity calculation unit 104, a chemotaxis index calculation unit 105, and a test result determination unit 106, all of which are included in the processing unit 100.

The image acquisition unit 101 acquires an image from the photographing apparatus 2.

The pixel coupling unit 102 couples pixels of the image acquired from the photographing apparatus 2.

The luminance information acquisition unit 103 acquires, from the pixels coupled by the pixel coupling unit 102 (which may also be referred to as coupled pixels), luminance information in each of the post-coupled pixels.

The luminous center of gravity calculation unit 104 calculates a luminous center of gravity, based on the luminance information acquired by the luminance information acquisition unit 103. The luminous center of gravity used herein will be explained hereinafter.

The chemotaxis index calculation unit 105 calculates a chemotaxis index of the nematodes, based on the luminous center of gravity calculated by the luminous center of gravity calculation unit 104. The chemotaxis index used herein will be explained hereinafter.

The test result determination unit 106 determines positivity or negativity for cancer, based on the chemotaxis index calculated by the chemotaxis index calculation unit 105.

The input device 14 is a keyboard, a mouse, or the like.

The output device 15 is a display, a printer, or the like.

The transmitter-receiver 16 is a NIC (Network Interface Card) or the like.

[Photographing Apparatus]

Figure 4:
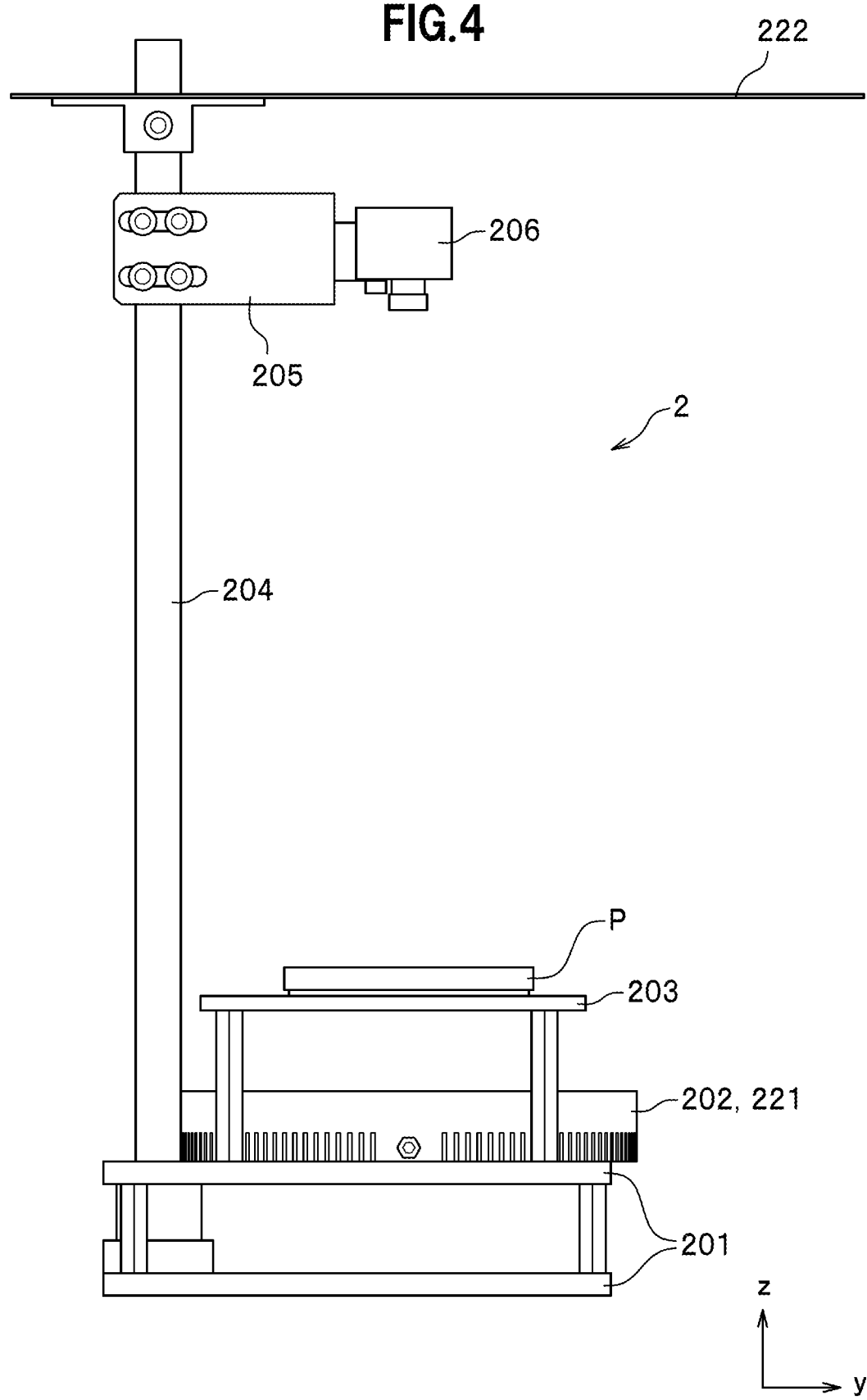
FIG. 4 is an external side elevational diagram illustrating a photographing apparatus according to the first embodiment.
Figure 5:
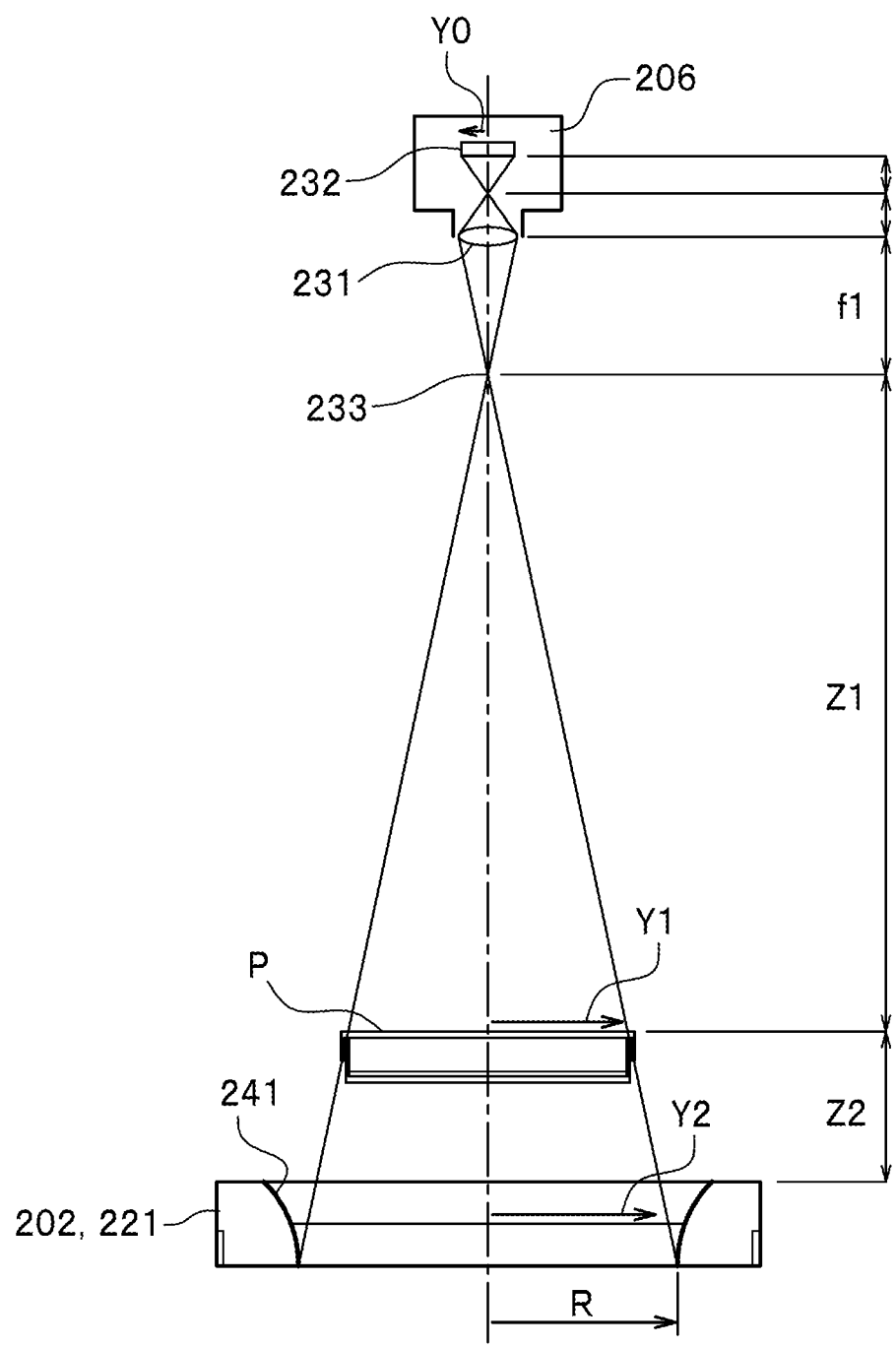
FIG. 5 is a cross-sectional schematic diagram illustrating the photographing apparatus according to the first embodiment.

FIG. 3 is an external perspective diagram illustrating a photographing apparatus used in the first embodiment. FIG. 4 is an external side elevational diagram illustrating the photographing apparatus according to the first embodiment. FIG. 5 is a cross-sectional schematic diagram illustrating the photographing apparatus used in the first embodiment.

As illustrated in FIG. 3 and FIG. 4, the photographing apparatus 2 has a light source unit 202 installed on a base unit 201. The light source unit 202 is realized by a diffuser-panel-attached ring LED light source 221. The diffuserpanel-attached ring LED light source 221 is a ring-shaped LED light source and has a diffuser panel 241 inside the ring thereof, as illustrated in FIG. 5.

As illustrated in FIG. 3 and FIG. 4, a seat 203 on which a plate P is set is disposed on the light source unit 202. The seat 203 has a hole into which the plate P is set. The plate P is fitted into the hole, which allows the plate P to be set up in the photographing apparatus 2.

As illustrated in FIG. 3 and FIG. 4, the base unit 201 is equipped with a bar-like first support member 204. The first support member 204 is equipped with a second support member 205 which can be moved along the first support member 204 in an up-and-down direction (in a Z direction).

The second support member 205 has, on an end thereof, a camera (photographing unit) 206 for photographing the plate P.

As illustrated in FIG. 4, a douser 222 which blocks light in a room such as a fluorescent light is disposed above the camera 206 (in FIG. 3, the douser 222 is not shown, though).

Note that, in FIG. 4, the douser 222 is disposed on the first support member 204, but the present invention is not limited to this. The douser 222 may be disposed anywhere else as long as the plate P is not illuminated by the light in the room, and may be disposed, for example, somewhere in the room.

If light from the light source unit 202 is directly irradiated to the plate P, the light may be too bright, or a specific portion of the plate P such as a rim thereof may become shiny. Because of the reasons above, there is a problem that a S/N (Signal/Noise) ratio of a photographed image is inconveniently reduced.

As illustrated in FIG. 3 to FIG. 5, the diffuser-panel-attached ring LED light source 221 is disposed as the light source unit 202, which allows light irradiated from a LED light source to be diffused. This makes it possible to irradiate appropriate light to the plate P. Thus, the S/N ratio of the photographed image can be improved, and an image analysis to be described later can be performed more easily.

The douser 222 is disposed above the camera 206 as mentioned above. This makes it possible to block light in a room such as a fluorescent light and to prevent a culture medium surface of the plate P from shining owing to light in the room.

Next is described a condition such that an image taken by the camera 206 is not influenced by the light source unit 202, that is, a condition for reducing uneven illuminance on a surface of the image, with reference to FIG. 5.

Let us assume a case where an illumination distance Z2 exists, at which an excellent illuminance distribution of light irradiated to the plate P is shown, depending on properties of the light source unit 202 (the diffuser-panel-attached ring LED light source 221). The excellent illuminance distribution can be obtained, when condition 1 and condition 2 shown below are satisfied. The illumination distance Z2 used herein means a distance between a surface of the light and a surface of an object to be photographed (herein, a culture medium surface of the plate P) as illustrated in FIG. 5.

Condition 1 expresses that f1 and Z1 satisfy formula (1) shown below. The f1 and the Z1 will be described hereinafter. Condition 2 expresses that an internal radius R of the diffuser-panel-attached ring LED light source 221 is larger than a field of view radius Y2 at a position of the light source. When condition 1 and condition 2 are satisfied, an image photographed by the camera 206 is not affected by the light source unit 202. This makes it possible to easily obtain luminance information, which will be described hereinafter.

$$Y1 = (Z1 \times Y0)/f1 \quad (1)$$

In formula (1), f1 is a front focal distance which is a distance between an imaging lens 231 and a front focus 233. Z1 is a distance between the front focus 233 and a surface of an object to be photographed (herein, a culture medium surface on the plate P). Y0 is a size of an image pickup device 232 of the camera 206. Y1 is a size of the object to be photographed.

When the condition 1 and the condition 2 are satisfied, uneven illuminance in an image can be reduced, and a S/N ratio of the image can be improved.

[Test Process]

Figure 6A:
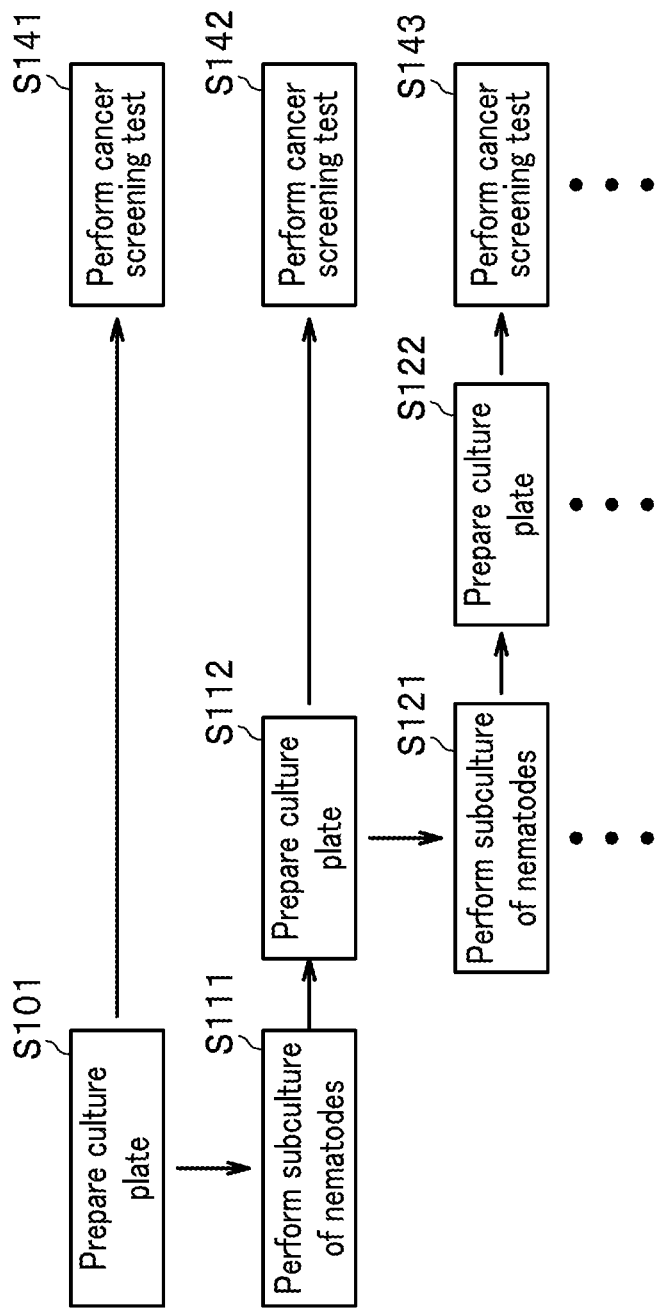
FIGS. 6A and 6B are each an example of a detailed procedure for performing a cancer screening test according to the first embodiment.
Figure 6B:
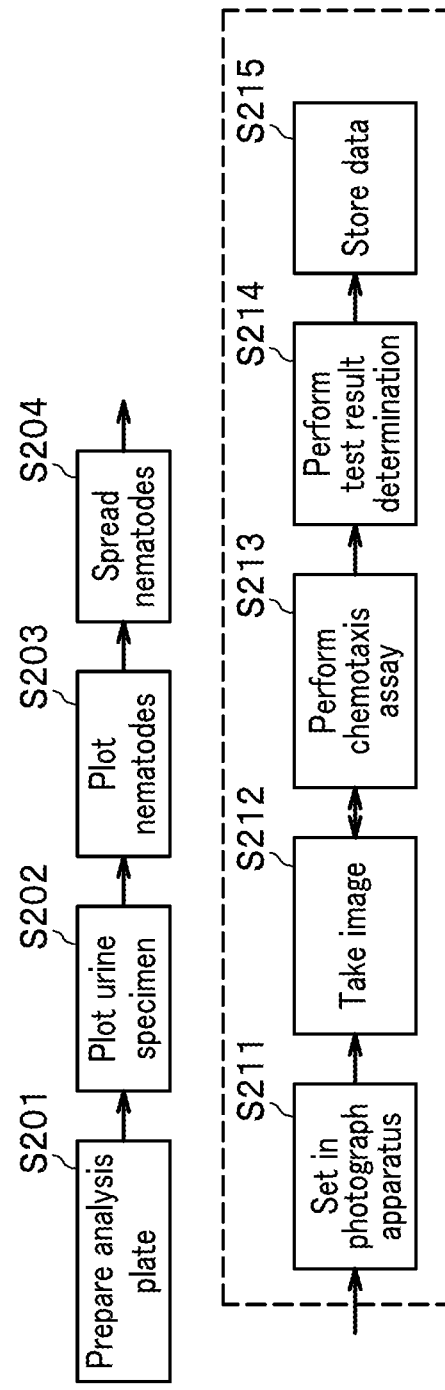

FIGS. 6A and 6B are each a diagram illustrating an example of a detailed procedure for performing a cancer screening test according to the first embodiment. FIG. 6A is a diagram illustrating a culture process, and FIG. 6B is a diagram illustrating a cancer screening test process.

As illustrated in FIG. 6A, a technician in preparing plates prepares a culture plate (S101). The plate technician performs subculture of nematodes where appropriate (S111), to thereby prepare a new culture plate (S112). The plate technician further performs subculture of nematodes, based on the culture plate prepared in step S111 (S121), to thereby prepare a further new culture plate (S122).

After the nematodes in respective culture plates prepared in step S101, S112, and S122 are cultured, a tester performs a cancer screening test using the cultured nematodes (S141 to S143).

FIG. 6B illustrates details of steps S141 to S143 in FIG. 6A. Note that steps S201 to S215 are performed in each of steps S141 to S143.

As illustrated in FIG. 6B, in the cancer screening test, the plate technician prepares an analysis plate (S201).

The tester plots sodium azide for paralyzing the nematodes on an analysis plate prepared by the plate technician, where appropriate. Plotting of the sodium azide may be omitted.

The tester plots a specimen on the analysis plate (S202).

The tester plots the nematodes on the analysis plate (S203).

The tester spreads the nematodes plotted on the analysis plate (S204), and sets the analysis plate in the photographing apparatus 2 (FIG. 1) (S211).

The photographing apparatus 2 takes an image of the analysis plate (S212).

The photographing apparatus 2 transmits the taken image to the analyzer 1 (FIG. 1). The analyzer 1 performs a chemotaxis assay based on the transmitted image (S213). In some cases, those steps are repeatedly performed such that the photographing apparatus 2 takes another image of the analysis plate (S212), and the analyzer 1 performs a chemotaxis assay of the image obtained by taking another image (S213).

The analyzer 1 performs a test result determination processing for determining positivity or negativity of the specimen for cancer, based on a result of the chemotaxis assay in step S213 (S214).

The analyzer 1 stores the result obtained in step S215 in the storage device 13 (FIG. 2) (S215).

[Flowchart]

FIG. 7 is a flowchart illustrating a procedure of a processing performed by the cancer analysis system used in the first embodiment. FIG. 1 to FIG. 3 are also to be referenced where appropriate.

The camera 206 of the photographing apparatus 2 takes an image of the plate P (S301).

The image acquisition unit 101 of the analyzer 2 acquires an image from the photographing apparatus 2, as an image acquisition processing (S302).

The pixel coupling unit 102 performs a pixel coupling processing (S303). The pixel coupling processing will be described hereinafter.

The luminance information acquisition unit 103 acquires luminance information from the pixel coupled in step S303 (a coupled pixel), as a luminance information acquisition processing (S304).

The luminous center of gravity calculation unit 104 calculates a luminous center of gravity based on the luminance information acquired in step S304, as a luminous center of gravity calculation processing (S305). The luminous center of gravity will be explained hereinafter.

The processing unit 100 determines whether or not steps S301 to S305 have been performed twice (S311).

If it is determined in step S311 that steps S301 to S305 have not yet been performed twice (S311→No), the processing unit 100 determines whether or not a prescribed time (for example, 15 minutes) has already passed after completion of step S305 (S312).

If it is determined in step S312 that the prescribed time has not yet passed after completion of step S305 (S312→No), the processing unit 100 returns the processing back to step S312.

If it is determined in step S312 that the prescribed time has already passed after completion of step S305 (S312→Yes), the processing unit 100: returns the processing back to step S301; and sends an instruction to the photographing apparatus 2 to take an image of the plate P.

If it is determined in step S311 that steps S301 to S305 have already been performed twice (S311→Yes), the chemotaxis index calculation unit 105 calculates a chemotaxis index based on the luminous center of gravity calculated in step S305, as a chemotaxis index calculation processing (S321).

The test result determination unit 106 determines positivity or negativity for cancer based on the chemotaxis index calculated in step S321, as a test result determination processing (S322).

Note that: step S301 in FIG. 7 corresponds to step S212 in FIG. 6; steps S302 to S321 in FIG. 7, to step S213 in FIG. 6; and step S322 in FIG. 7, to step S214 in FIG. 6.

[Chemotaxis Assay Using Luminous Center of Gravity]

Figure 8:
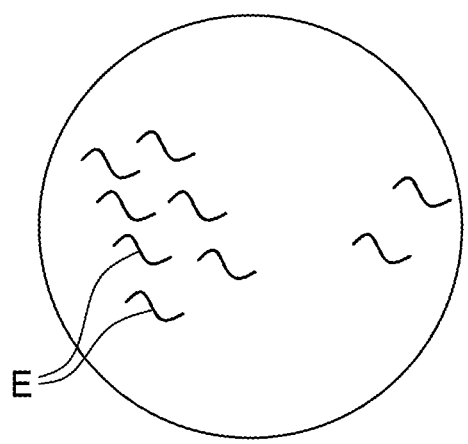
FIG. 8 is a schematic diagram illustrating an image taken by a camera.
Figure 9:
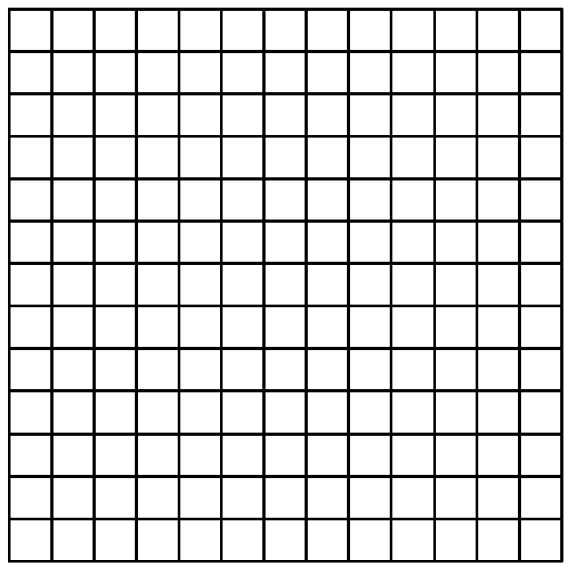
FIG. 9 is a diagram illustrating a coupling processing of pixels performed in the first embodiment.
Figure 10:
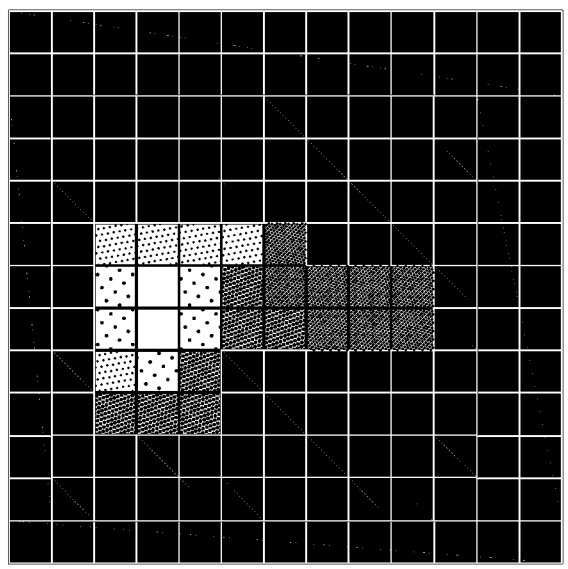
FIG. 10 is a diagram illustrating a result of the pixel coupling processing.

Next is described a chemotaxis assay of nematodes using a luminous center of gravity used in the first embodiment, with reference to FIG. 8 to FIG. 10.

(Image)

FIG. 8 is a schematic diagram illustrating an image taken by a camera. The image is the one acquired in step S302 in FIG. 7.

In FIG. 8, a culture medium appears white and the nematodes E appear black for easy visibility. Actually, however, the culture medium is imaged black and the nematodes E are imaged white.

(Pixel Coupling Processing)

FIG. 9 is a diagram illustrating a coupling processing of pixels performed in the first embodiment. The processing corresponds to step S303 in FIG. 7.

The pixel coupling unit 102 couples a prescribed number of pixels in a photographed image to form a group of approximately 13×13 pixels, as illustrated in FIG. 9. Note that the integration into the approximately 13×13 pixels is one example, and the number of the pixels to be grouped into may be any other number.

(Luminance Information Acquisition Processing)

FIG. 10 is a diagram illustrating a result of the pixel coupling processing.

As illustrated in FIG. 10, in the pixel after coupling (the coupled pixel), the more the nematodes in the pixel, the closer to white the pixel appears. In contrast, the less the nematodes, the closer to black. In other words, the more the nematodes present in the coupled pixel, the higher the luminance. In FIG. 10, whether a large or a small number of the nematodes are present in the coupled pixel is indicated by five-level dots. Actually, however, the number of the nematodes is indicated by, for example, 256-level luminance.

In step S304 in FIG. 7, the luminance information acquisition unit 103 acquires luminance information on the coupled pixel as illustrated in FIG. 10. An x-axis and a y-axis thereof will be described hereinafter.

(Luminous Center of Gravity Calculation Processing)

In step S305 in FIG. 7, the luminous center of gravity calculation unit 104 calculates a luminous center of gravity based on a luminance of the coupled pixel illustrated in FIG. 10. The luminous center of gravity is calculated by the following formula (2) and is a center of gravity of luminance of an image having been subjected to the pixel coupling processing.

[formula]

$$\left( \frac{\sum_{i=1}^{n} (x_i \cdot Bx_i)}{\sum_{i=1}^{n} Bx_i}, \frac{\sum_{j=1}^{m} (y_j \cdot By_j)}{\sum_{j=1}^{m} By_j} \right) \quad (2)$$

In formula (2), let "$x_i$" be an x-coordinate of an i-th coupled pixel from the left in FIG. 10, and let $B_{xi}$ be a luminance of the pixel. Similarly, let "$y_j$" be a y-coordinate of a j-th coupled pixel from the bottom in FIG. 10, and let $By_j$ be a luminance of the pixel. Those x-coordinate and the y-coordinate are on a basis of the x-axis and the y-axis in FIG. 10, respectively. In formula (2), "n" and "m" are the numbers of the coupled pixels in an x-axis direction and a y-axis direction, respectively. In FIG. 10, n=13 and m=13, as one example.

The $Bx_i$ is a value obtained by adding up luminances of the coupled pixels belonging to $x_i$, in the y-axis direction. $By_j$ is a value obtained by adding up luminances of the coupled pixels belonging to $y_j$, in the x-axis direction.

That is, Bxi and Byj in formula (2) are defined by formula (3) and formula (4) as below, respectively, in which "$Bi_j$" is a luminance of a coupled pixel at a position (i, j) (that is, a pixel in an i-th position from the left and a j-th position from the bottom in FIG. 10).

[formulae]

$$Bx_i = \sum_{j=1}^{m} B_{ij} \quad (3)$$

$$Bx_j = \sum_{i=1}^{n} B_{ij} \quad (4)$$

Let ($C_x$, $C_y$) be a luminous center of gravity of a coupled pixel at a position of the calculated (x, y) (that is, at an x-th position from the left and a y-th position from the bottom in FIG. 10). Let ($C_{xt}$, $C_{yt}$) be a luminous center of gravity at a time t.

(Chemotaxis Index Calculation Processing)

In step S305 of FIG. 7, the chemotaxis index calculation unit 105 calculates a chemotaxis index CI using the luminous center of gravity by means of techniques described below. The chemotaxis index CI can be calculated in two ways, one by means of formula (5) and the other by means of formula (6) as shown below. Note that ($C_{x0}$, $C_{y0}$) denotes a luminous center of gravity at the time t=0, that is, immediately after the plotting.

$$CI = C_{x0} - C_{xt} \quad (5)$$

[formula]

$$CI = \sqrt{(C_{x0} - C_{xt})^2 + (C_{y0} - C_{yt})^2} \quad (6)$$

Formula (5) calculates a change over time of a luminous center of gravity in the x-axis direction. Formula (6) calculates a change over time of a luminous center of gravity in the x-axis direction and in the y-axis direction. Note that "t" may take a value of, for example, but not limited to, 15 minutes.

The test result determination unit 106 determines positivity or negativity for cancer of a subject tested, based on the calculated chemotaxis index CI.

In the first embodiment, the chemotaxis index can be obtained not by counting the number of nematodes one by one, but by calculating based on the luminance using a simple algorithm. Analysis of an image taken by the photographing apparatus 1 can also be made efficiently.

Figure 11:
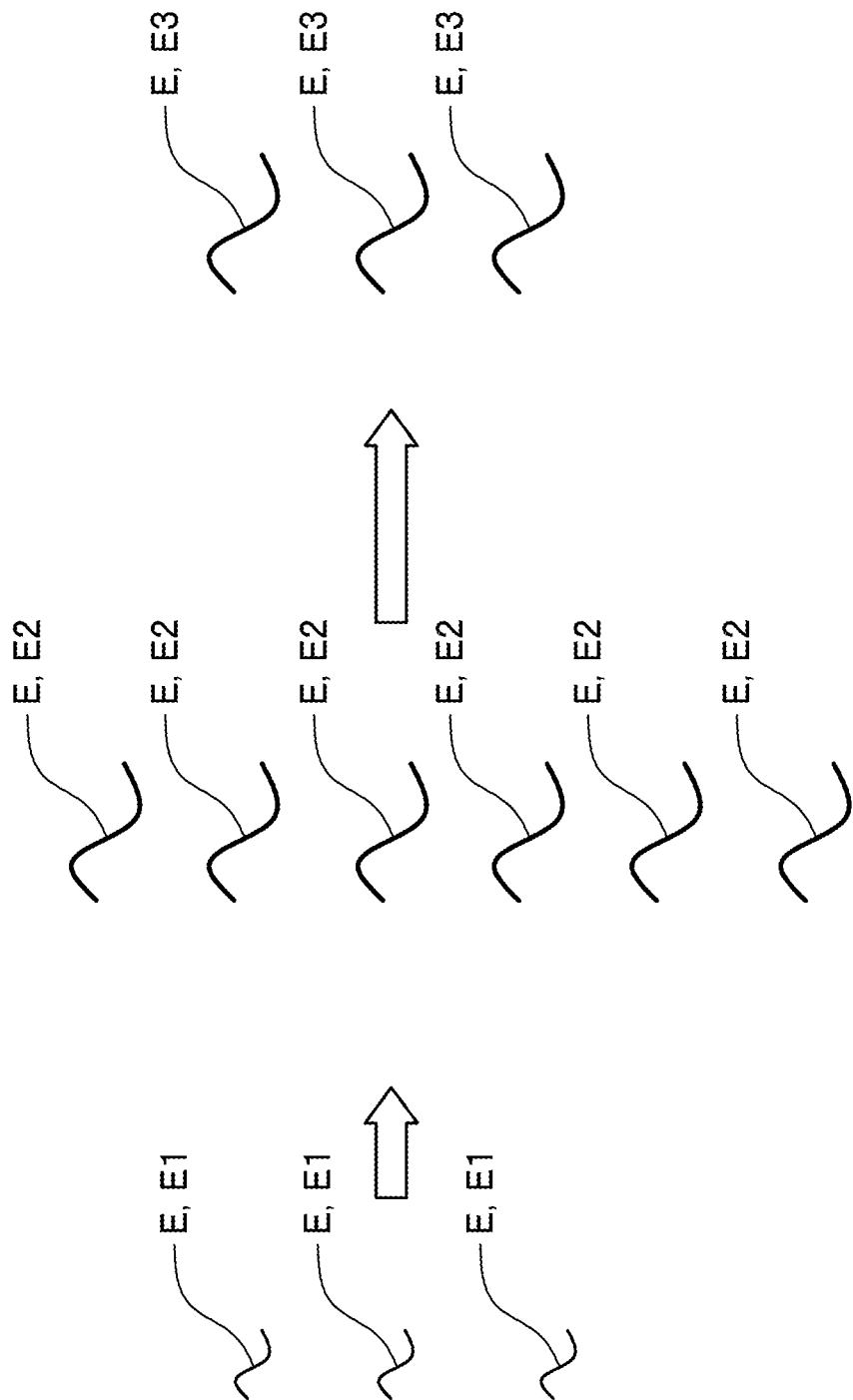
FIG. 11 is a schematic diagram illustrating selection of nematodes.

As illustrated in FIG. 11, even if nematodes E are cultured from a larval stage (a reference numeral E1) to an adult stage (a reference numeral E2) under a uniform condition, it is not possible to keep all of the nematodes in good condition. It is thus necessary to select some of the nematodes E in good condition (a reference numeral E3). The nematodes E3 in good condition used herein mean active nematodes.

Measurement of movement of each of the nematodes E requires, however, a complicated algorithm. The cancer analysis system Z according to the first embodiment can in this regard reduce computational load, by using the luminous center of gravity which makes use of a finding that the more the nematodes E are present in an area in an image, the brighter the area becomes.

As described above, the nematodes E are plotted manually, a plotted point is not necessarily become a precise point of origin. As described above, the nematodes are, after plotted, manually spread in a prescribed range on a culture medium, which naturally has a two-dimensional breadth. Herein, as expressed in formula (5) and formula (6), the chemotaxis index is obtained by calculating a difference between a luminous center of gravity of nematodes immediately after being plotted and that after a lapse of a prescribed time. This makes it possible to eliminate a problem of deviation of the plotted point and to also eliminate a problem of having the two-dimensional breadth.

In other words, the chemotaxis index can be correctly evaluated when the luminous center of gravity immediately after the nematodes are plotted is taken as a point of origin.

The pixel coupling processing is performed herein. This makes it possible to reduce the number of pixels and a volume of images, thus allowing a large number of images to be stored. For example, when images are taken in 5 million pixels for 15 minutes, a capacity of about 1 GB is necessary. The capacity of images can be, however, greatly reduced if the pixel coupling processing is performed as in the first embodiment.

The pixel coupling processing can also makes it possible to average noise such as dust and to thereby eliminate influence of the noise.

Note that Patent Document 1 discloses that fluorescent protein genes are introduced into nematodes and fluorescence intensities thereof are measured. A technique disclosed in Patent Document 1 improves an S/N ratio of an image by making the nematodes fluorescent. In the technique disclosed in Patent Document 1, however, the number of the nematodes is counted one by one, which cannot solve the above-described problems. In the technique according to the first embodiment of the present invention, in contrast, an amount of nematodes is estimated based on luminance in an image, unlike the technique disclosed in Patent Document 1.

In the first embodiment, a chemotaxis index is calculated from a difference between a luminous center of gravity immediately after plotting and that after a lapse of a prescribed time. The chemotaxis index may be, however, calculated from a difference between the luminous center of gravity after a lapse of a prescribed time and a center position of the plate P.

In the first embodiment, pixels of a finely photographed image are coupled, but the present invention is not limited to this. The pixel coupling processing may be, however, omitted by, for example, photographing using the camera 206 (FIG. 3 to FIG. 5) having a small number of pixels. When the camera 206 having a small number of pixels is used, cost can be greatly reduced.

Second Embodiment

[Analysis Apparatus]

Figure 12:
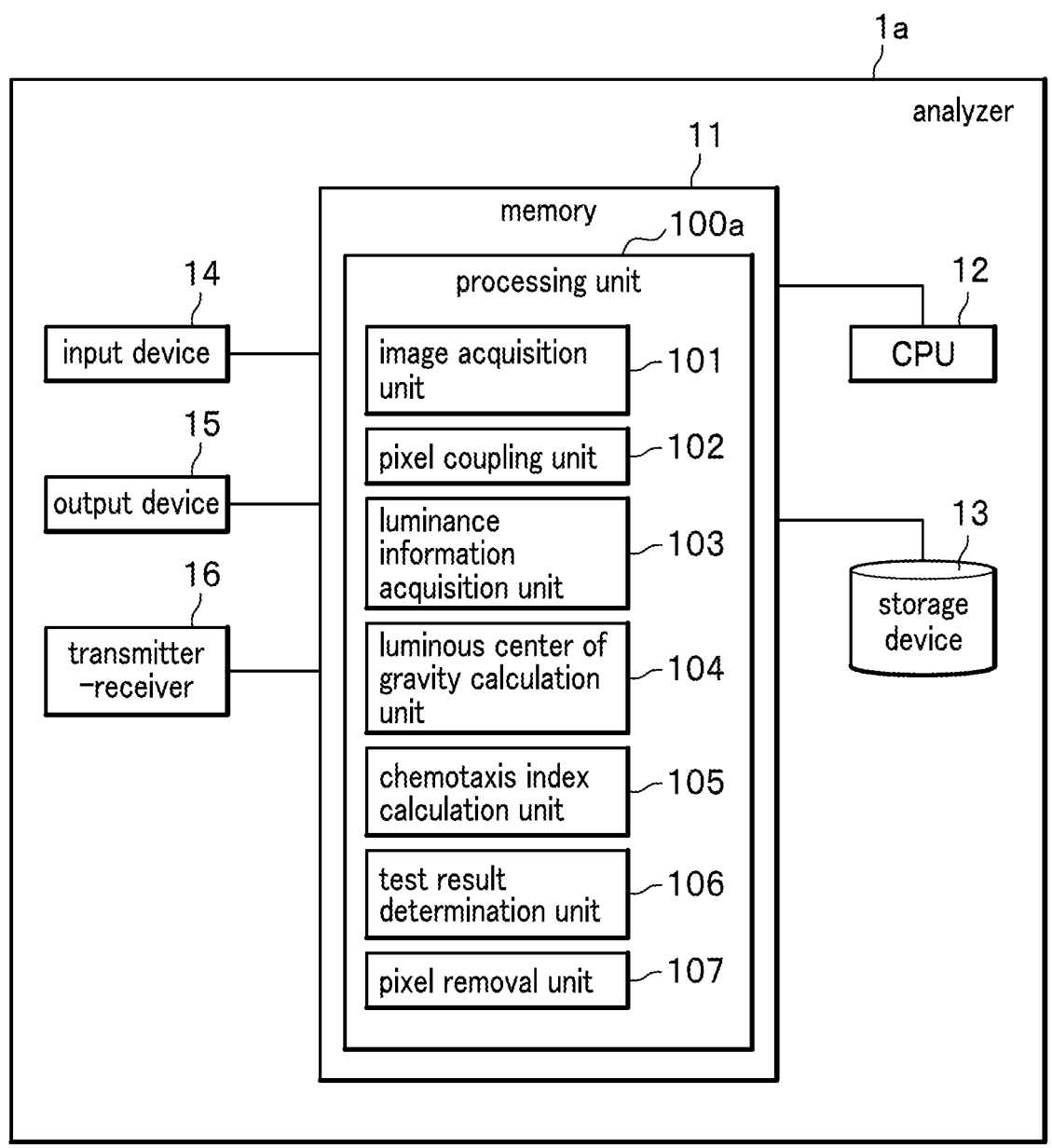
FIG. 12 is a functional block diagram illustrating a configuration of an analyzer according to a second embodiment.

FIG. 12 is a functional block diagram illustrating a configuration of an analyzer according to a second embodiment.

An analyzer 1a illustrated in FIG. 12 is similar to the analyzer 1 illustrated in FIG. 2 except that a processing unit 100a includes a pixel removal unit 107 that removes a coupled pixel positioned near the center.

[Flowchart]

Figure 13:
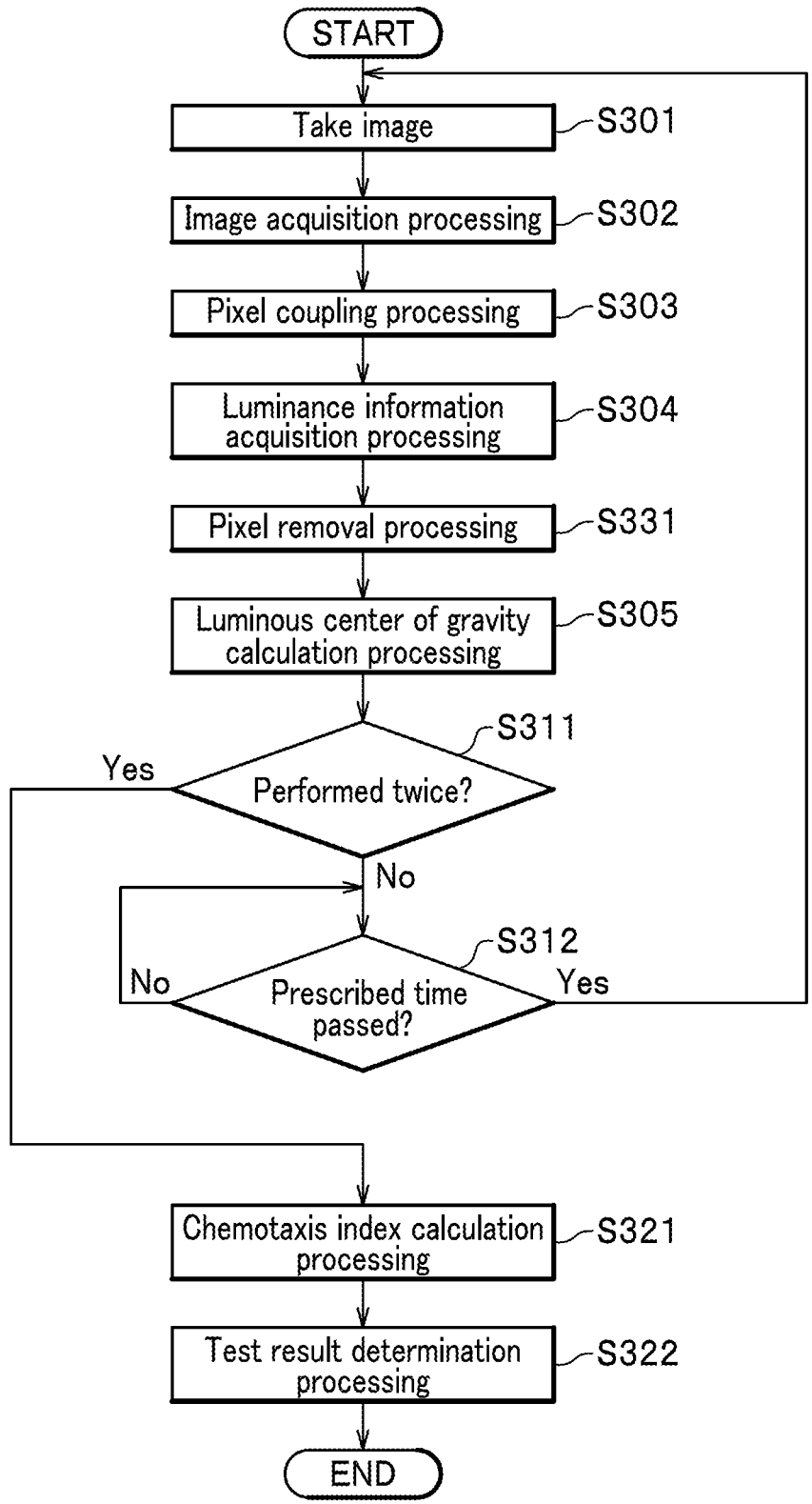
FIG. 13 is a flowchart illustrating a procedure of steps performed by the analyzer according to the second embodiment.

FIG. 13 is a flowchart illustrating a procedure of steps performed by the analyzer 1a according to the second embodiment, which is described with reference to FIG. 12 where appropriate.

The flowchart of FIG. 13 is similar to that of FIG. 7, except that, after step S304, the pixel removal unit 107 performs a pixel removal processing (S331). The pixel removal processing will be described hereinafter.

(Pixel Removal Processing)

Figure 14:
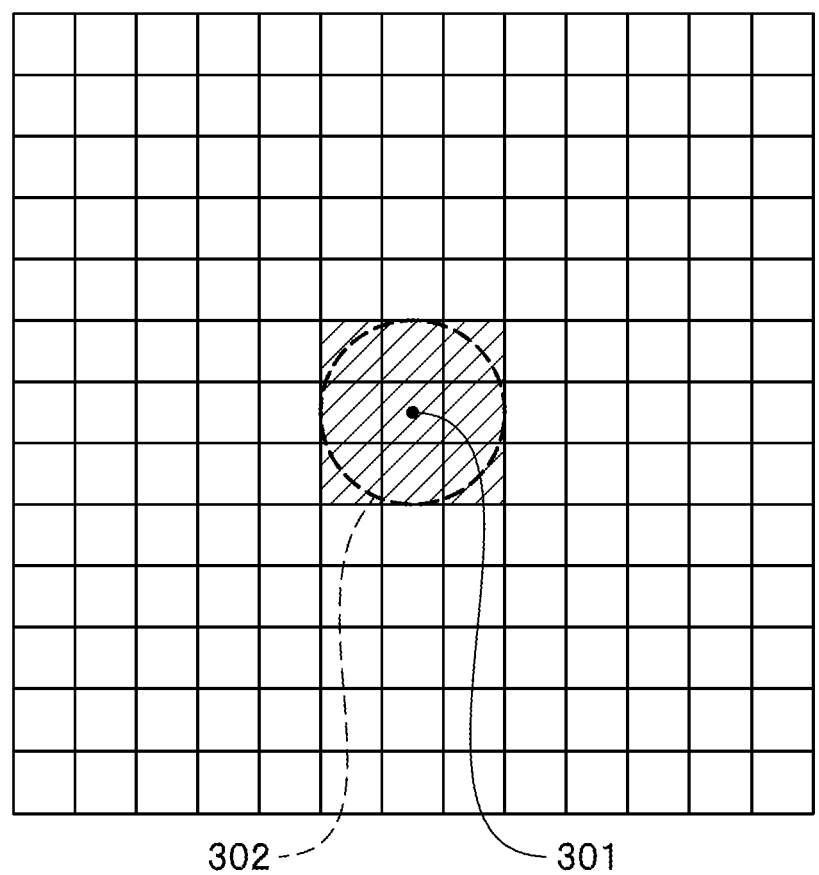
FIG. 14 is a diagram for explaining how to perform a pixel removal processing performed in the second embodiment.
Figure 15:
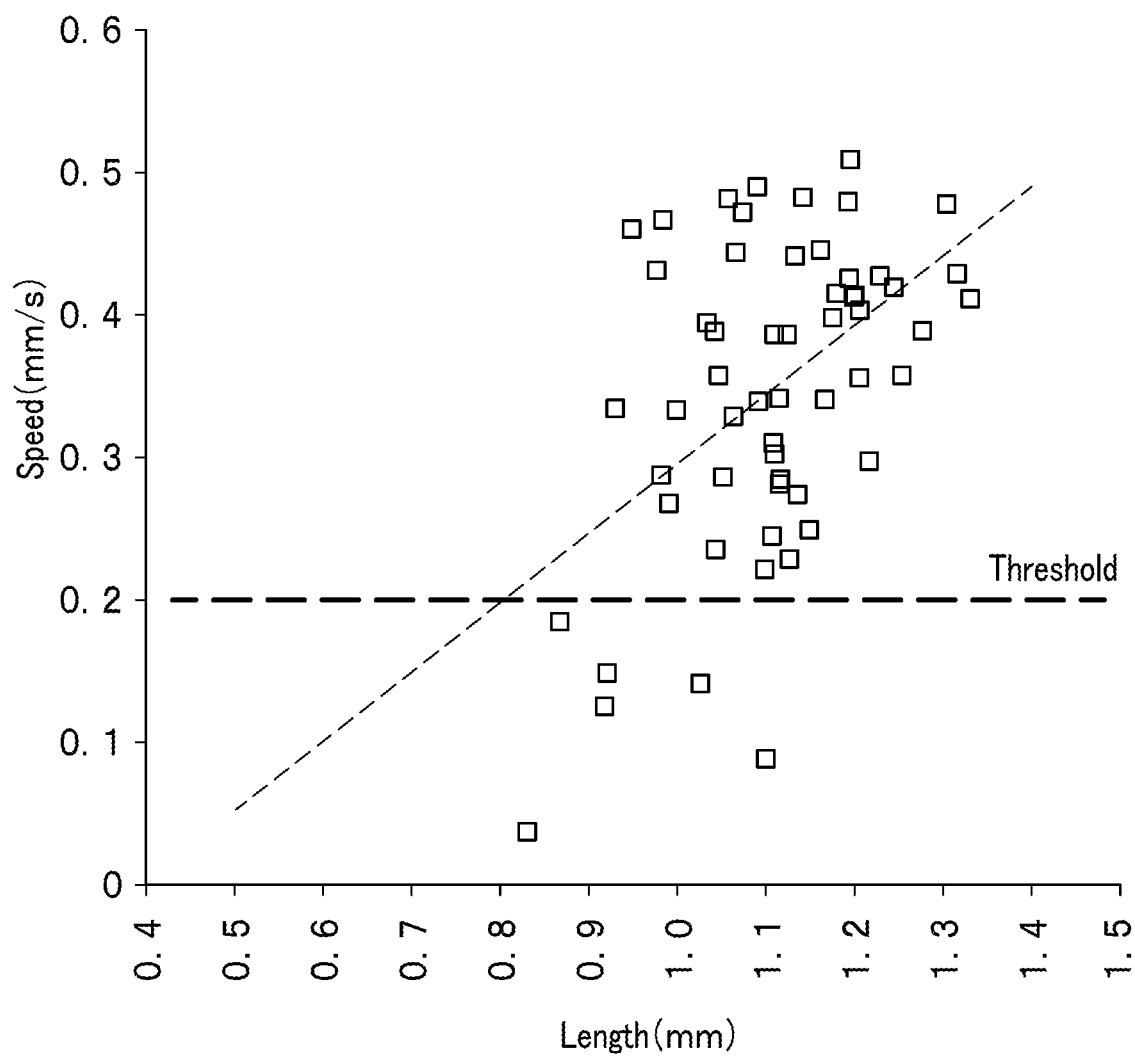
FIG. 15 is a diagram for explaining how to determine an area to be deleted, performed in the second embodiment.
Figure 16:
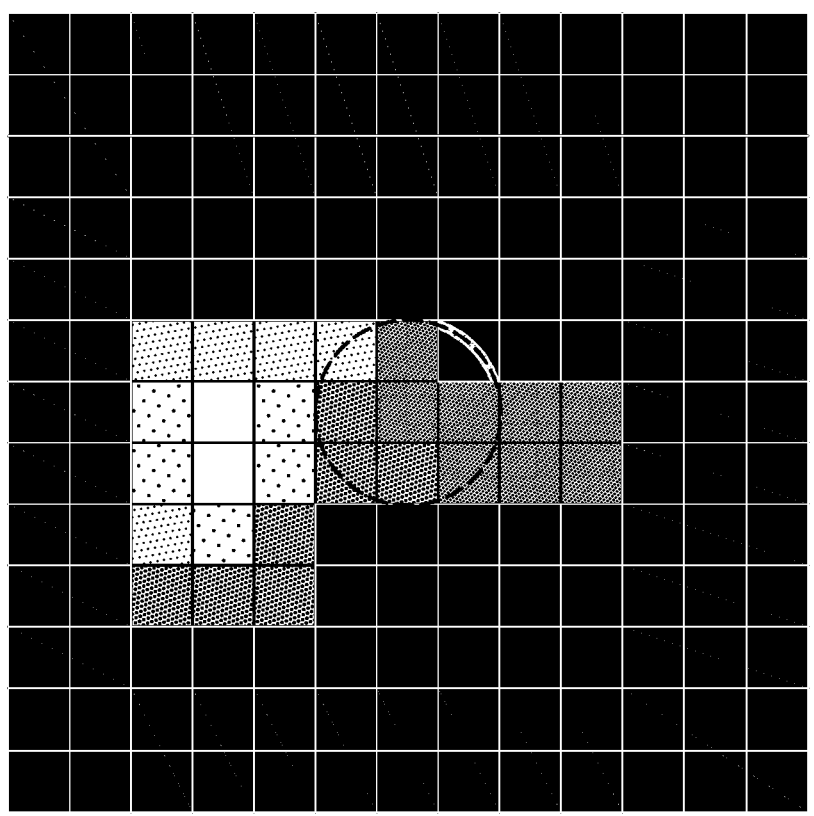
FIG. 16 is a schematic diagram illustrating a coupled pixel before a pixel removal processing is performed (before processing).

Next is described the pixel removal processing in step S331 of FIG. 13, with reference to FIG. 14 to FIG. 16.

FIG. 14 is a diagram for explaining how to perform the pixel removal processing which is performed in the second embodiment.

A pixel illustrated in FIG. 14 is a coupled pixel.

As illustrated in FIG. 14, the pixel removal unit 107 removes a coupled pixel within a prescribed range (a shaded area) from a center (a reference numeral 301) of an image a prescribed time has passed from a start of the chemotaxis. The removal is conducted because nematodes not in good condition stay in a central area (that is, where the nematodes have been plotted). By performing the pixel removal processing, influence by those nematodes not in good condition can be eliminated, and accuracy in the luminous center of gravity and the chemotaxis index can be improved.

An area to be removed may include, for example:

(A1) a coupled pixel, part or all of which is overlapped with a circle having a diameter of (Lapse time after plotting nematodes×Speed of slow nematodes) (a dashed circle 302 in FIG. 14)

(A2) a coupled pixel in an area specified by an operator.

FIG. 15 is a diagram for explaining how to determine an area to be removed, which is performed in the second embodiment.

In FIG. 15, a horizontal axis represents a length (mm) of a nematode, and a vertical axis, a taxis speed (mm/s) thereof. Note that it is known that the length of a nematode is relevant to the taxis speed thereof. That is, it has been found that, if a nematode has a small length, the nematode is low in speed.

As illustrated in FIG. 15, the nematodes can be divided at the speed of 0.2 mm/s into: a group of nematodes in good condition; and a group of nematodes in poor condition.

Thus, a nematode which stays in place for one minute is determined as a nematode in poor condition, and a circle having a radius of "0.2×60 (seconds)=12 mm" (the dashed circle 302 in FIG. 14) is set. A coupled pixel (the shaded coupled pixel in FIG. 14), part or all of which is overlapped with the dashed circle 302 is then set as a coupled pixel to be removed.

Figure 17:
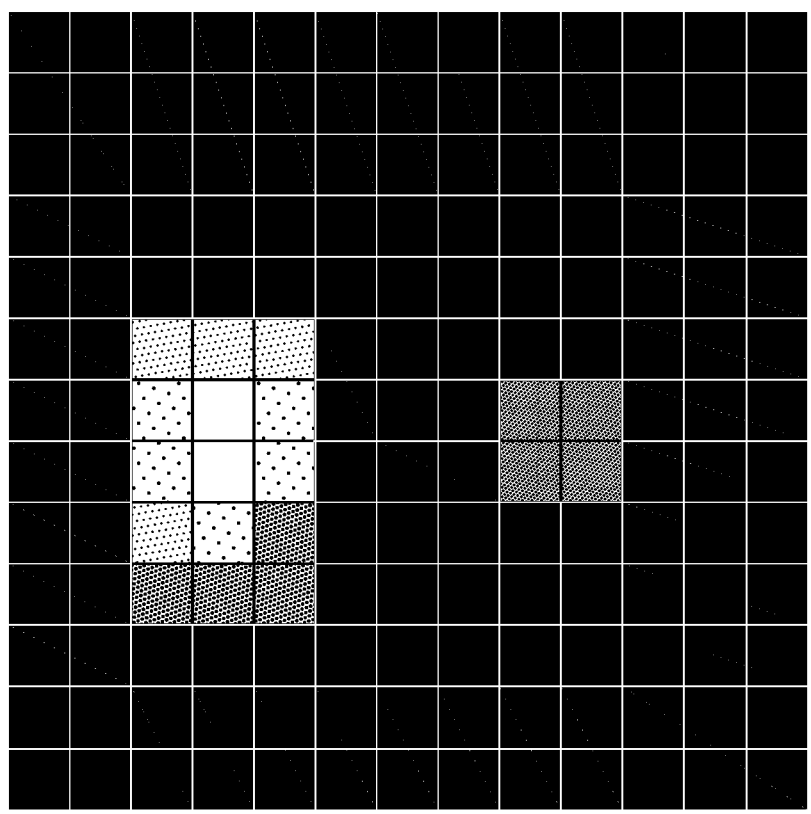
FIG. 17 is a schematic diagram illustrating a coupled pixel after the pixel removal processing is performed.

FIG. 16 is a schematic diagram illustrating a coupled pixel before a pixel removal processing is performed (before processing). FIG. 17 is a schematic diagram illustrating a coupled pixel after the pixel removal processing is performed.

In FIG. 16 and FIG. 17, luminance of a coupled pixel is indicated by five-level dots, similarly to FIG. 10.

FIG. 16 is similar to FIG. 10, and description thereof is omitted herefrom. The pixel removal unit 107 removes a coupled pixel, part or all of which is overlapped with the dashed circle, in a central area of an image after the pixel coupling processing, to thereby obtain an image after coupling as illustrated in FIG. 17. Note that the dashed circle in FIG. 16 is similar to the dashed circle 302 in FIG. 15.

FIGS. 18A and 18B are each a diagram illustrating a time variation in a center of gravity coordinate of a sample of a cancer patient by the minute and a change in coordinates by the minute. FIG. 18A illustrates a case where the pixel removal processing has not yet been performed (before processing). FIG. 18B illustrates a case where the pixel removal processing has already been performed.

Note that, in FIGS. 18A and 18B and FIG. 19 to be described hereinafter, respective x-coordinates and y-coordinates of the luminous center of gravity and the change in coordinates are shown. A urine sample is, however, plotted on the x-axis direction, and a change only in the x-axis direction is observed. In FIGS. 18A and 18B and FIG. 19, the circle corresponding to the dashed circle 302 in FIG. 14 has a diameter of 14 mm. Further, in FIGS. 18A and 18B and FIG. 19, the luminous center of gravity is calculated using the pixel removal processing, in and after 3 minutes from a start of taxis. In other words, in FIG. 18B, the pixel removal processing is not yet performed from a time immediately after plotting, to 2 minutes from the start of the taxis. This is because, if the pixel removal processing is performed, a distance of migration of the nematodes during a period of time from immediately after the plotting to a prescribed time is too short that a coupled pixel in which almost all of the nematodes are still present may be inconveniently removed. As described above, it is preferable not to perform the pixel removal processing during a period of time from a start of a taxis (immediately after plotting) to a prescribed time.

Note that the urine sample for use in FIGS. 18A and 18B and FIG. 19 to be described hereinafter is diluted to 10 times by water.

The term "immediately after" used herein means immediately after plotting of nematodes on a culture medium. The center of gravity coordinate is a coordinate of a luminous center of gravity. The change in coordinates is represented by "(Coordinate of current luminous center of gravity)− (Coordinate of luminous center of gravity immediately after plotting of nematodes)". That is, the luminous center of gravity immediately after plotting is a point of origin. Since the change in coordinates is rounded off the second decimal place, a value of the change in coordinates may not be exactly same as the "(Coordinate of current luminous center of gravity)− (Coordinate of luminous center of gravity immediately after plotting of nematodes)". The same applies hereinafter.

The center of gravity coordinate and the change in coordinates each takes a value of "+" when a nematode exhibits a behavior of being attracted; and, a value of "−" when a nematode exhibits a behavior of being repelled. As described above, a nematode exhibits a behavior of being repelled by urine of a healthy subject and a behavior of being attracted to a cancer patient.

When a result illustrated in FIG. 18A in which the pixel removal processing is yet to be performed is compared to a result illustrated in FIG. 18B in which the processing has already been performed, it is demonstrated that the result illustrated in FIG. 18B in which the processing has already been performed is shifted to a positive direction with respect to the x-axis.

FIGS. 19A and 19B are each a diagram illustrating a time variation of a center of gravity coordinate of a healthy subject by the minute and a change in coordinates by the minute. FIG. 19A illustrates a case where the pixel removal processing has not yet been performed (before processing). FIG. 19B illustrates a case where the pixel removal processing has already been performed. The vertical axes and the horizontal axes in FIGS. 19A and 19B are similar to those in FIGS. 18A and 18B, respectively.

When a result illustrated in FIG. 19A in which the pixel removal processing is yet to be performed is compared to a result illustrated in FIG. 19B in which the processing has already been performed, it is demonstrated that the result illustrated in FIG. 19B in which the processing has already been performed is shifted to a negative direction of the x-axis.

Moving speed of nematodes in good condition, that is, active nematodes is high. It is possible to select nematodes in good condition by measuring movement of each of nematodes.

According to the second embodiment, influence by nematodes in poor condition (inactive nematodes) can be eliminated by removing a coupled pixel within a prescribed range from the center. This makes it possible to improve accuracy of the chemotaxis index. Such pixel removal in the central area can be achieved simply by setting a luminance of a coupled pixel within a prescribed range to null, which is a remarkably simple processing.

Third Embodiment

[Analysis Apparatus]

Figure 20:
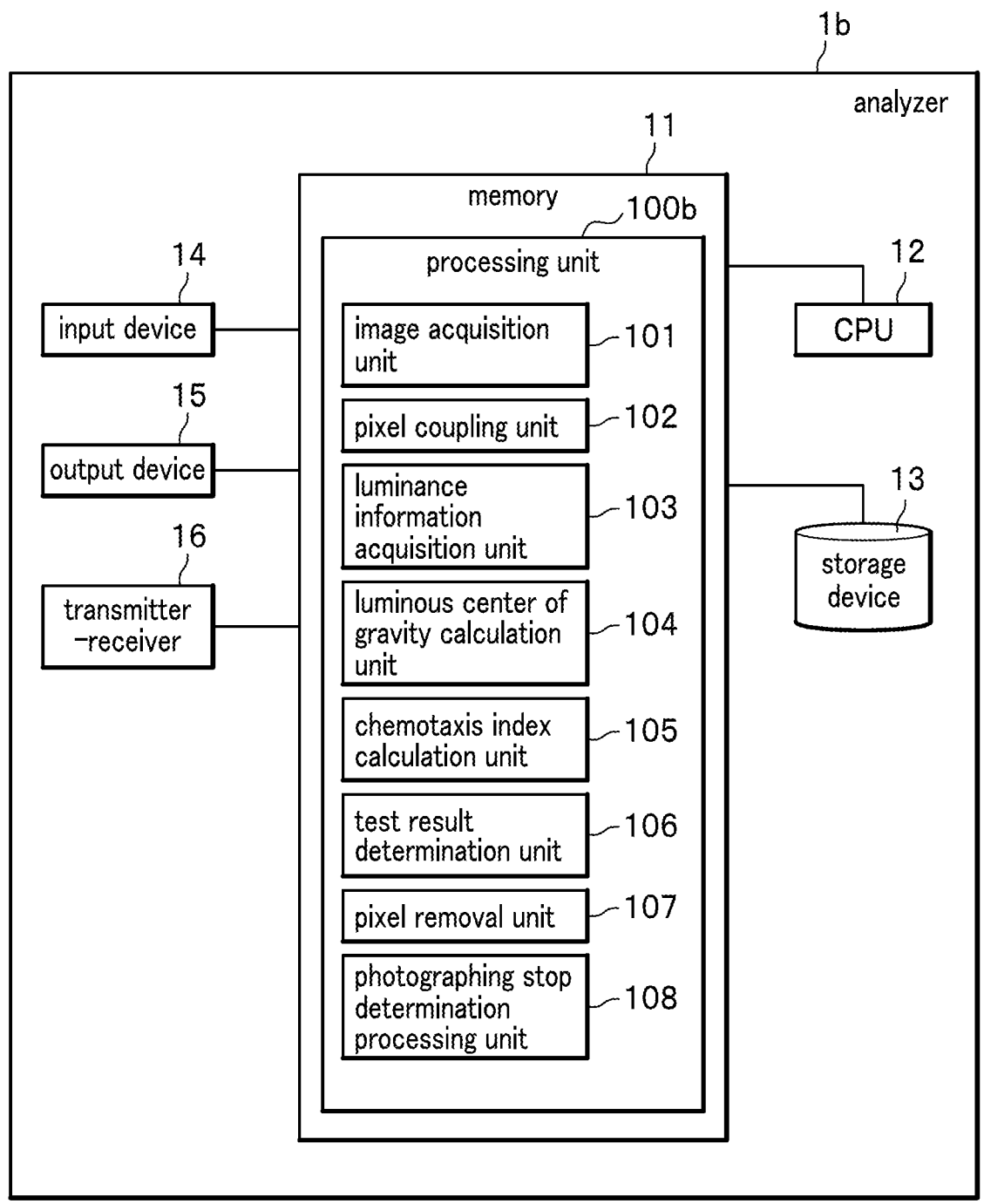
FIG. 20 is a functional block diagram illustrating a configuration of an analyzer according to a third embodiment.

FIG. 20 is a functional block diagram illustrating a configuration of an analyzer according to a third embodiment.

An analyzer 1b illustrated in FIG. 20 is similar to the analyzer 1a illustrated in FIG. 12 except that a processing unit 100b includes a photographing stop determination processing unit 108 that stops calculation of a luminous center of gravity, when a time variation of the luminous center of gravity meets a prescribed condition.

[Flowchart]

Figure 21:
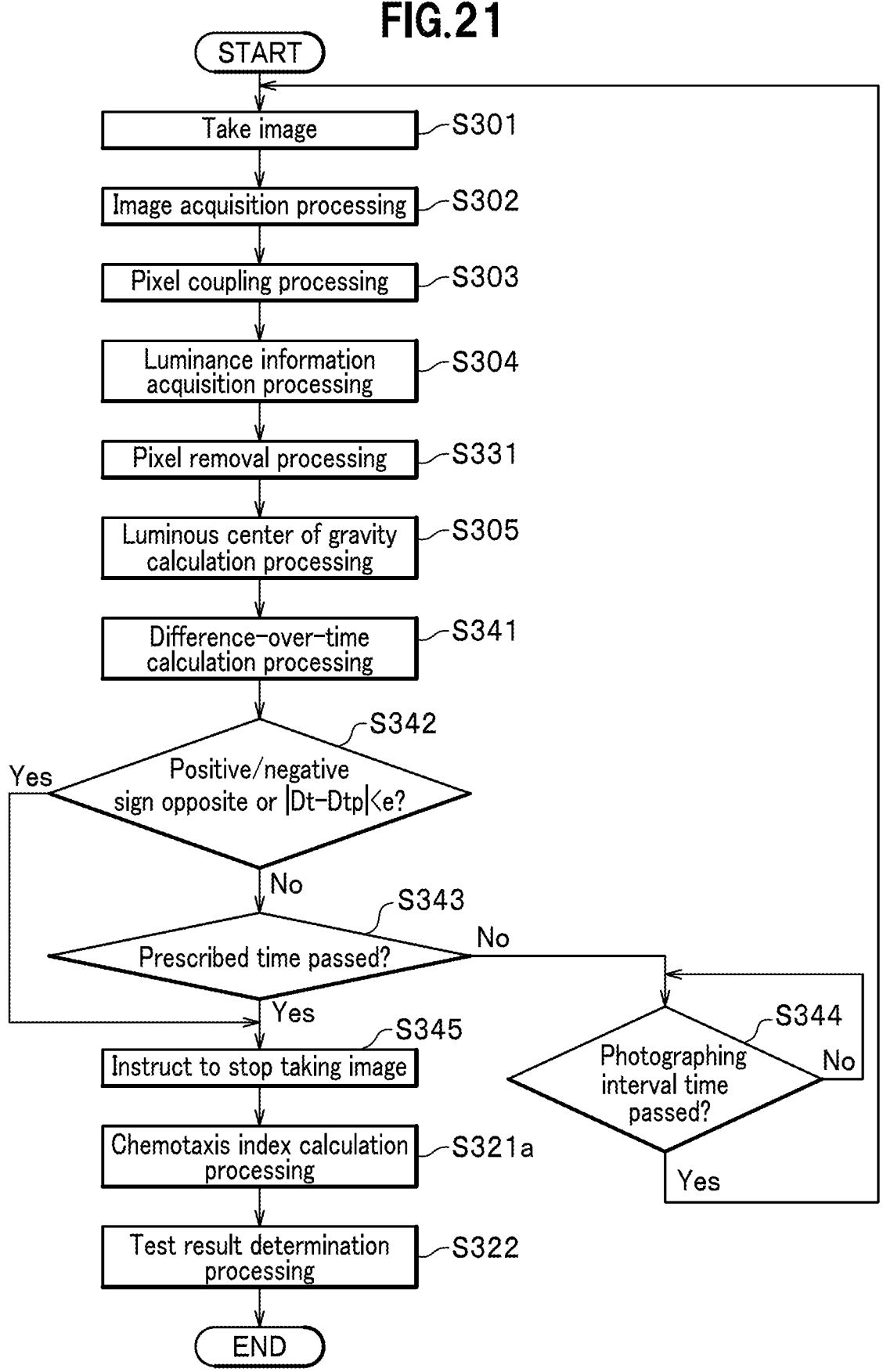
FIG. 21 is a flowchart illustrating a procedure of steps performed by the analyzer according to the third embodiment.

FIG. 21 is a flowchart illustrating a procedure of steps performed by the analyzer according to a third embodiment, which is described with reference to FIG. 3 and FIG. 20 where appropriate.

A processing of FIG. 21 is different from that of FIG. 13 as described below.

In step S305, after the luminous center of gravity calculation unit 104 calculates a luminous center of gravity, the photographing stop determination processing unit 108 calculates a difference over time Dt of the luminous center of gravity, as a difference-over-time calculation processing (S341). The difference over time Dt of the luminous center of gravity is a difference value between a current luminous center of gravity and a preceding luminous center of gravity. Note that, when a direction in which a urine sample is plotted with respect to the center of a plate is defined as an x-axis direction, the difference over time Dt of the luminous center of gravity only in the x-axis direction is to be taken into account. In addition to the x-axis direction, however, that in a y-axis direction may also be taken into account.

The photographing stop determination processing unit 108 determines: whether or not a positive/negative sign of the difference over time of the luminous center of gravity calculated in step S341 becomes opposite to a positive/negative sign of a difference over time of a preceding luminous center of gravity; or, whether or not an absolute value (|Dt-Dtp|) of a difference between the difference over time Dt of the luminous center of gravity calculated in step S341 and a difference over time Dtp of a preceding luminous center of gravity is less than a prescribed value (e) (S342). Note that, in step S342, the latter condition of whether or not the absolute value (|Dt-Dtp|) of the difference between the difference over time Dt of the luminous center of gravity calculated in step S341 and the difference over time Dtp of the preceding luminous center of gravity is less than the prescribed value (e) may be omitted.

If it is determined in step S342 that the positive/negative sign of the difference over time of the luminous center of gravity calculated in step S341 becomes opposite to the positive/negative sign of the difference over time of the preceding luminous center of gravity; or, the absolute value (|Dt-Dtp|) of the difference between the difference over time Dt of the luminous center of gravity calculated in step S341 and the difference over time Dtp of the preceding luminous center of gravity is less than the prescribed value (e) (S342→Yes), the processing unit 100b advances the processing to step S345.

If it is determined in step S342 that the positive/negative sign of the difference over time of the luminous center of gravity calculated in step S341 does not become opposite to the positive/negative sign of the difference over time of the preceding luminous center of gravity; and, at the same time, the absolute value (|Dt-Dtp|) of the difference between the difference over time Dt of the luminous center of gravity calculated in step S341 and the difference over time Dtp of the preceding luminous center of gravity is equal to or more than a prescribed value (e) (S342→No), the processing unit 100b further determines whether or not a prescribed time (for example, 15 minutes) has passed from a start of the chemotaxis (S343).

If it is determined in step S343, the prescribed time has not yet passed from the start of the chemotaxis (S343→No), the photographing stop determination processing unit 108 determines whether or not a photographing interval time (for example, 1 minute) has already passed after a previous image was taken (S344).

If it is determined in step S344 that the photographing interval time has not yet passed (S344→No), the photographing stop determination processing unit 108 returns the processing back to step S344.

If it is determined in step S344 that the photographing interval time has already passed (S344→Yes), the processing unit 100b: returns the processing back to step S301, and sends an instruction to the photographing apparatus 2 to take an image of the plate P.

If it is determined in step S343 that the prescribed time has already passed from the start of the chemotaxis (S343→Yes), the photographing stop determination processing unit 108 transmits an instruction to the photographing apparatus 2 to stop taking an image (S345). Upon the instruction to stop taking an image, the photographing apparatus 2 stops taking an image.

The chemotaxis index calculation unit calculates a chemotaxis index 105 based on a luminous center of gravity most recently calculated (S321a).

[Time Variation of Luminous Center of Gravity]

(Case of Cancer Patient)

FIG. 22 is a table showing a time variation of a luminous center of gravity in a case where urine of a cancer patient is used as a sample.

More specifically, FIG. 22 illustrates coordinates of the luminous center of gravity and a change in the coordinates by the minute. As described above, the change in coordinates used herein is (Coordinate of current luminous center of gravity)−(Coordinate of luminous center of gravity immediately after plotting). Note that, in FIG. 22 to FIG. 29, respective x-coordinates and y-coordinates of the luminous center of gravity and the change in the coordinates are shown. The urine sample is, however, plotted in the x-axis direction, and only a change in the x-axis direction is thus focused on herein. In each of FIG. 22 to FIG. 29, the pixel removal processing is performed using techniques similar to those in FIG. 18 and FIG. 19.

Figure 23:
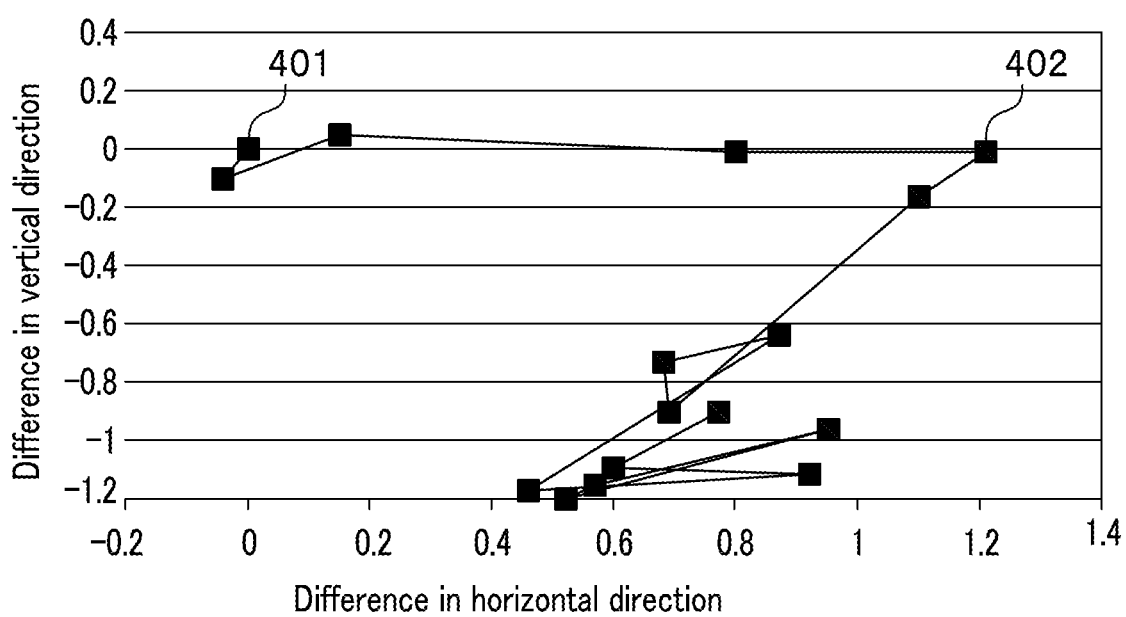
FIG. 23 is a diagram illustrating a time variation of a luminous center of gravity in a case of a cancer patient.

FIG. 23 is a diagram illustrating a time variation of a luminous center of gravity in a case of a cancer patient.

Note that, in FIG. 23 and FIG. 27 to be described hereinafter, plotting on coordinates is performed based on the change in coordinates (formula (6)). This is because plotting of nematodes is manually performed, and also, as described above, the nematodes (and buffer) are spread in a prescribed range after plotting, to thereby plot possibly different points on culture media in repeating tests. In contrast, the change in coordinates has a luminous center of gravity immediately after plotting, as a point of origin, which can eliminate a possible variation of plotted points resulting from manual plotting.

In FIG. 23, the x-axis and the y-axis represent a chemotaxis range of nematodes (on a culture medium).

In FIG. 23, the reference numeral 401 denotes a luminous center of gravity immediately after nematodes are plotted. After that, positions of the luminous centers of gravity every one minute are represented.

The nematodes demonstrate a slowed-down movement on a + side such as migrating back and forth, with a reference numeral 402 as a turning point. One of the reasons may be diffusion of odorous substance of a urine sample.

Note that in FIG. 23, the luminous center of gravity one minute after the start of the chemotaxis is on a "−" side. This can be eliminated by omitting a photographing stop processing for a prescribed time (for example, 3 minutes) after the start of the chemotaxis.

Figure 24:
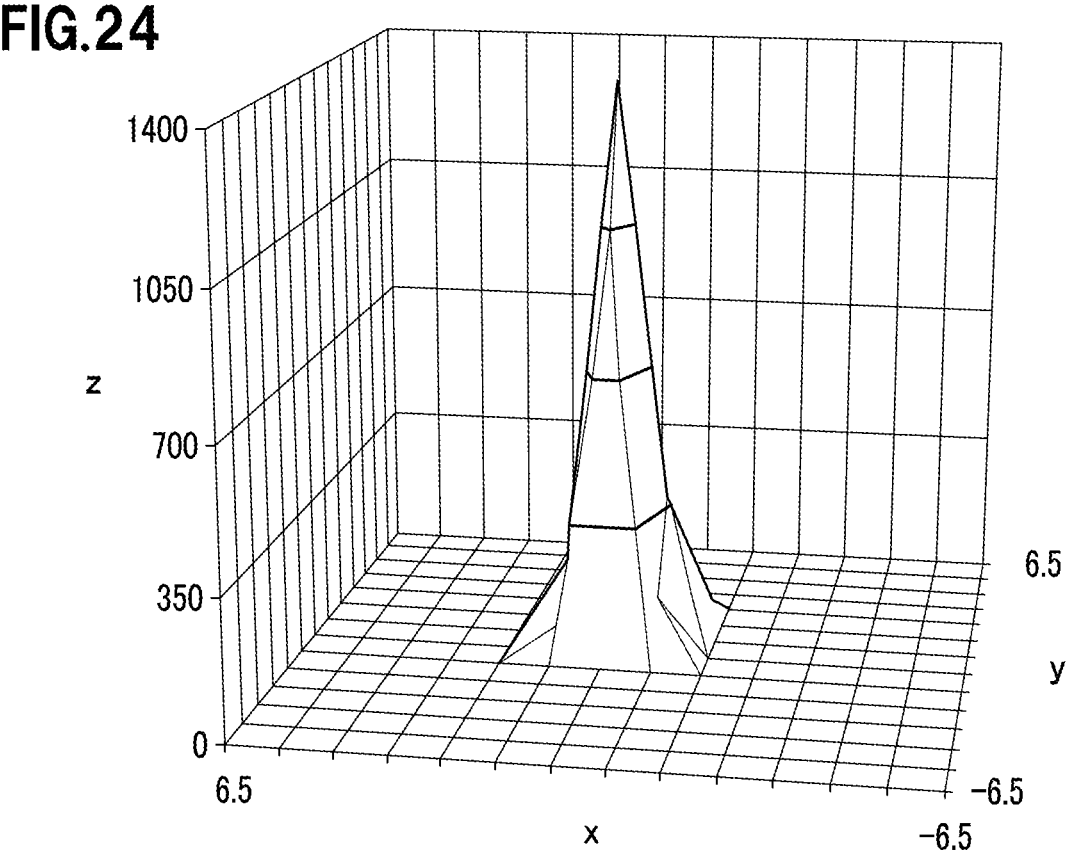
FIG. 24 is a diagram illustrating a luminance distribution of a urine sample of the cancer patient immediately after plotting nematodes.

FIG. 24 is a diagram illustrating a luminance distribution of a urine sample of the cancer patient immediately after the plotting.

Note that, in FIG. 24, coordinates on an x-axis and a y-axis represent an image transmitted from the photographing apparatus 2 (FIG. 1). Grids in FIG. 24 represent coupled pixels. In FIG. 24, a vertical axis represents luminance. The same applies to FIG. 25, FIG. 28, and FIG. 29. Note that each of FIG. 24, FIG. 25, FIG. 28, and FIG. 29 has a direction of the x-axis opposite to that of each of FIG. 23 and FIG. 27.

As illustrated in FIG. 24, the nematodes become concentrated at and around the center of the plate P (FIG. 3) immediately after the plotting, which results in a high luminance at and around the center.

Figure 25:
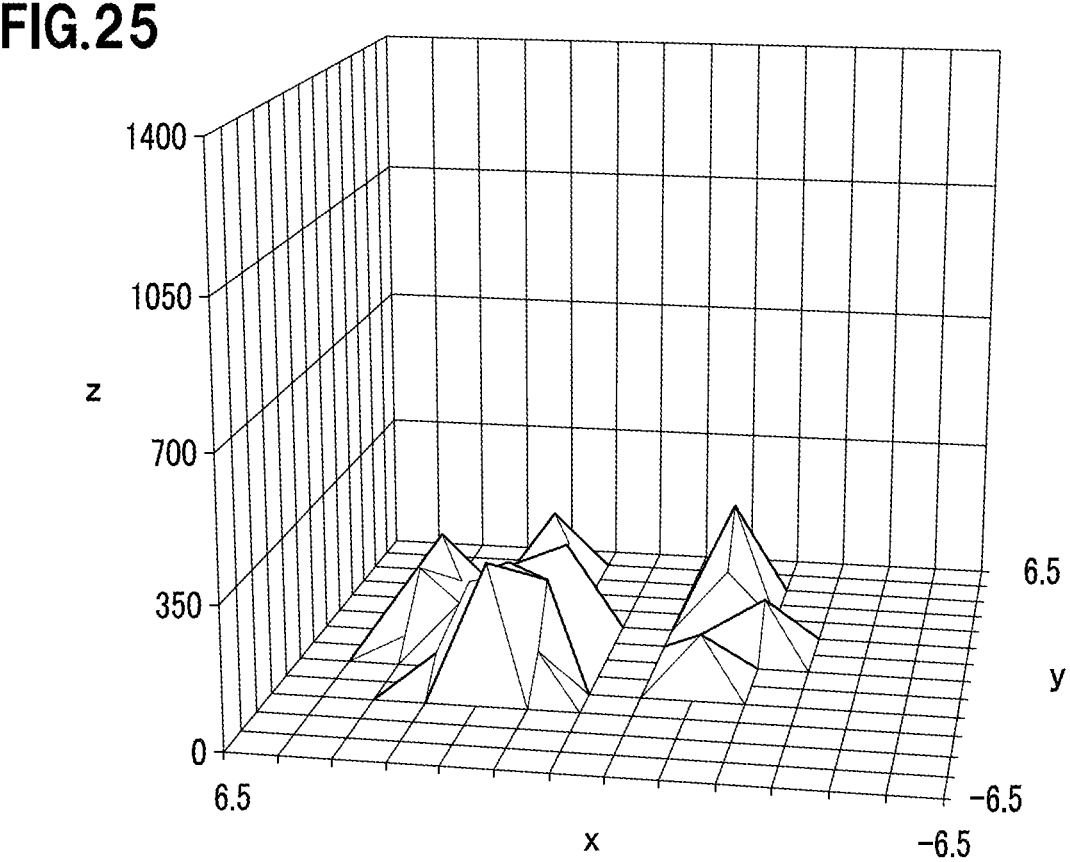
FIG. 25 is a diagram illustrating a luminance distribution of a urine sample of the cancer patient 4 minutes after the start of the chemotaxis.

FIG. 25 is a diagram illustrating a luminance distribution of a urine sample of the cancer patient 4 minutes after the start of the chemotaxis. More specifically, FIG. 25 illustrates a luminance distribution at the reference numeral 402 in FIG. 23.

In FIG. 25, two high peaks appear in the + direction owing to the chemotaxis of the nematodes.

(Case of Healthy Subject)

FIG. 26 is a table showing a time variation of a luminous center of gravity in a case where urine of a healthy subject is used as a sample.

More specifically, FIG. 26 illustrates a coordinate of the luminous center of gravity and a change in the coordinates every one minute.

Figure 27:
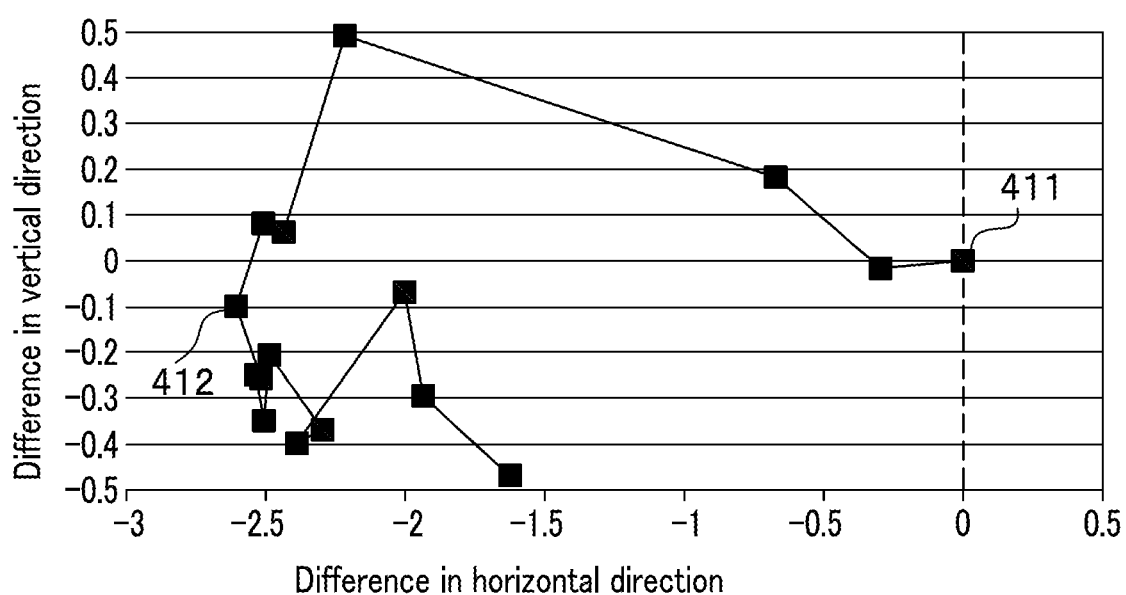
FIG. 27 is a diagram illustrating a time variation of a luminous center of gravity in a case of a healthy subject.

FIG. 27 is a diagram illustrating a time variation of a luminous center of gravity in a case of a healthy subject.

In FIG. 27, a vertical axis is same as that in FIG. 23. Note that a horizontal axis takes a negative value so as to represent behavior of being repelled of the nematodes.

In FIG. 27, a reference numeral 411 denotes a luminous center of gravity of nematodes immediately after the nematodes are plotted. After that, positions of the luminous centers of gravity every one minute are represented.

The nematodes demonstrate a slowed-down movement on a—side such as migrating back and forth, with a reference numeral 412 as a turning point.

Figure 28:
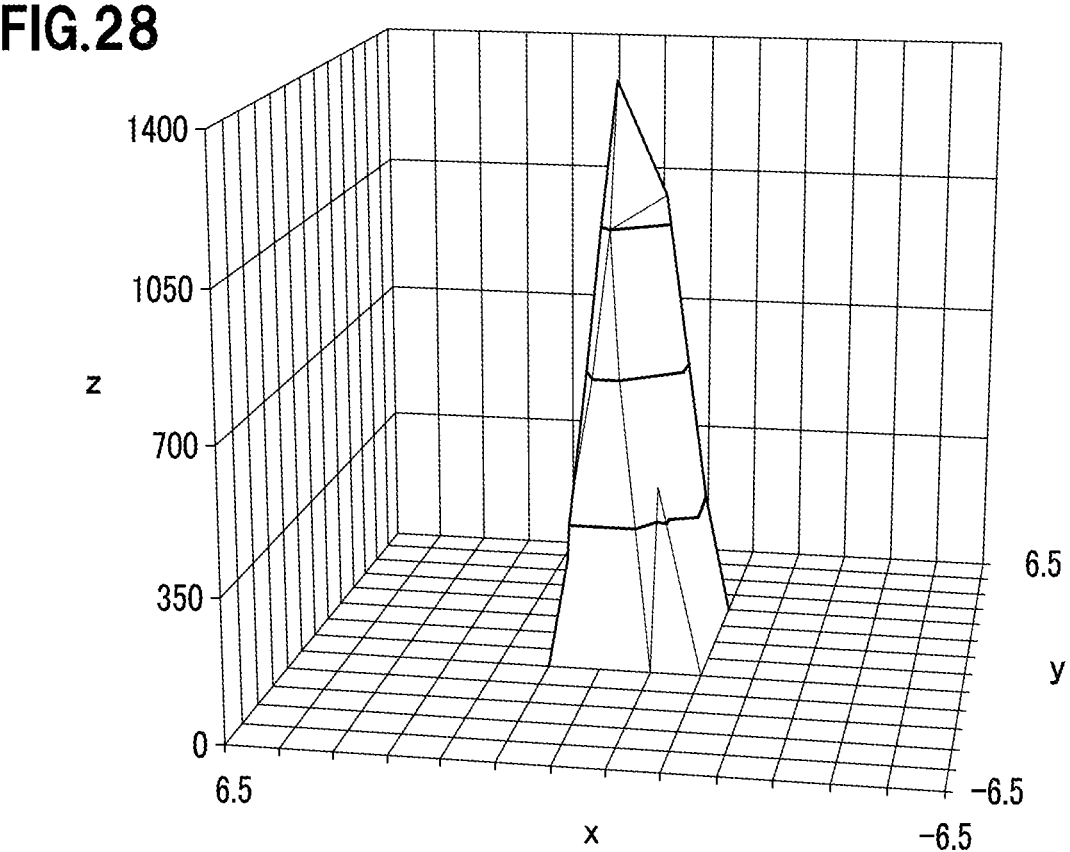
FIG. 28 is a diagram illustrating a luminance distribution of a urine sample of the healthy subject immediately after plotting nematodes.

FIG. 28 is a diagram illustrating a luminance distribution of a urine sample of the healthy subject immediately after the nematodes are plotted.

As illustrated in FIG. 28, the nematodes become concentrated at and around the center of the plate P (FIG. 3) immediately after the plotting, which results in a high luminance at and around the center.

Figure 29:
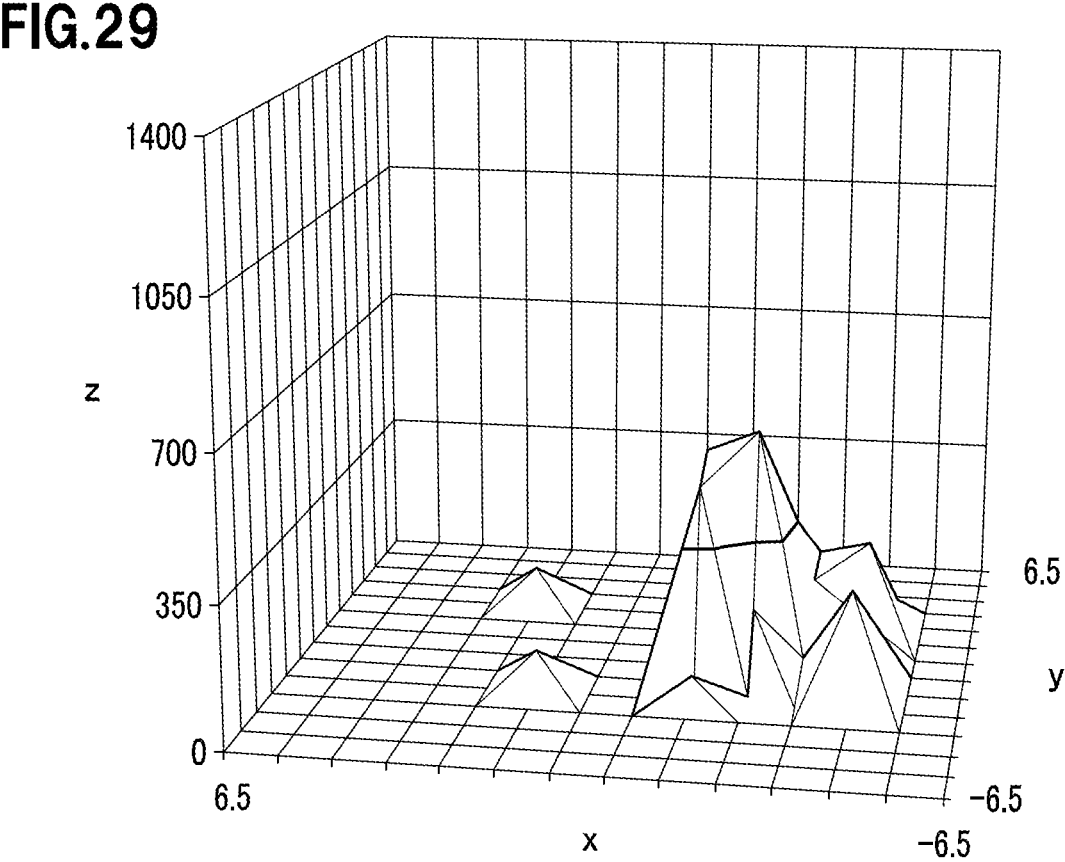
FIG. 29 is a diagram illustrating a luminance distribution of a urine sample of the healthy subject 6 minutes after the start of the chemotaxis.

FIG. 29 is a diagram illustrating a luminance distribution of a urine sample of the healthy subject 6 minutes after the start of the chemotaxis. In other words, FIG. 29 illustrates a luminance distribution at the reference numeral 412 in FIG. 27.

In FIG. 29, one high peak appears in the—direction owing to the taxis of the nematodes.

After the reference numeral 402 in FIG. 23 and the reference numeral 412 in FIG. 27, behavior of the nematodes is slowed down, and, even if the chemotaxis of the nematodes is continued, it is estimated that there is not much meaning.

Thus, the photographing stop determination processing unit 108: monitors the luminous center of gravity every prescribed time; and, when any of the luminous centers of gravity returns nearer to a point of origin (a point at which the nematodes are first plotted), discontinues photographing an image.

The chemotaxis index calculation unit 105 calculates a chemotaxis index using a preceding luminous center of gravity to the one at which photographing an image has been stopped.

In the third embodiment, photographing an image is stopped at a time when it is estimated that there may not be much meaning even if the chemotaxis of the nematodes is still continued. This makes it possible to reduce a time required for a test.

Also, in the third embodiment, the chemotaxis index is calculated based on a luminous center of gravity detected at a time when the chemotaxis exhibited by the nematodes is in a position nearest to the "+" side or the "−" side. This makes it possible to improve accuracy of the chemotaxis index.

The nematodes have been usually paralyzed using sodium azide or the like. In the third embodiment, paralyzation of nematodes by sodium azide is not, however, necessary, because the chemotaxis index is calculated based on the luminous center of gravity detected when the luminous center of gravity returns nearer to the point of origin, or the like. The sodium azide is toxic substance, and a prescribed rule has to be followed for discarding the sodium azide, which is a great burden on test facilities. As described above, if technology in the third embodiment is used, the sodium azide is not required, which is eco-friendly and can greatly reduce burden on test facilities.

Note that, in the third embodiment, the pixel removal processing of step S331 in FIG. 21 may be omitted.

In the third embodiment, the time variation of the luminous center of gravity is monitored each time a test is performed, and the chemotaxis index is calculated based on the luminous center of gravity detected when any of the luminous centers of gravity returns nearer to the point of origin. The present invention is not, however, limited to this. For example, an average value or the like of a period of time from a start of a test until a change in luminance returns nearer to a point of origin may be preliminarily calculated based on experiments, and a chemotaxis of nematodes may be performed only during the period of time. That is, the prescribed time in the first or second embodiment may be taken as an experimentally-calculated average value of periods of time when a test is started until when a change in luminance returns nearer to the point of origin. This makes it possible to reduce a time required for the test.

In the third embodiment, even when odorous substance of a urine sample is evaporated and nematodes return in a direction of the point of origin, the chemotaxis index can be calculated based on luminous center of gravity before the odorous substance of the urine sample is evaporated. This makes it possible to improve accuracy of the chemotaxis index.

Fourth Embodiment

[Analysis Apparatus]

Figure 30:
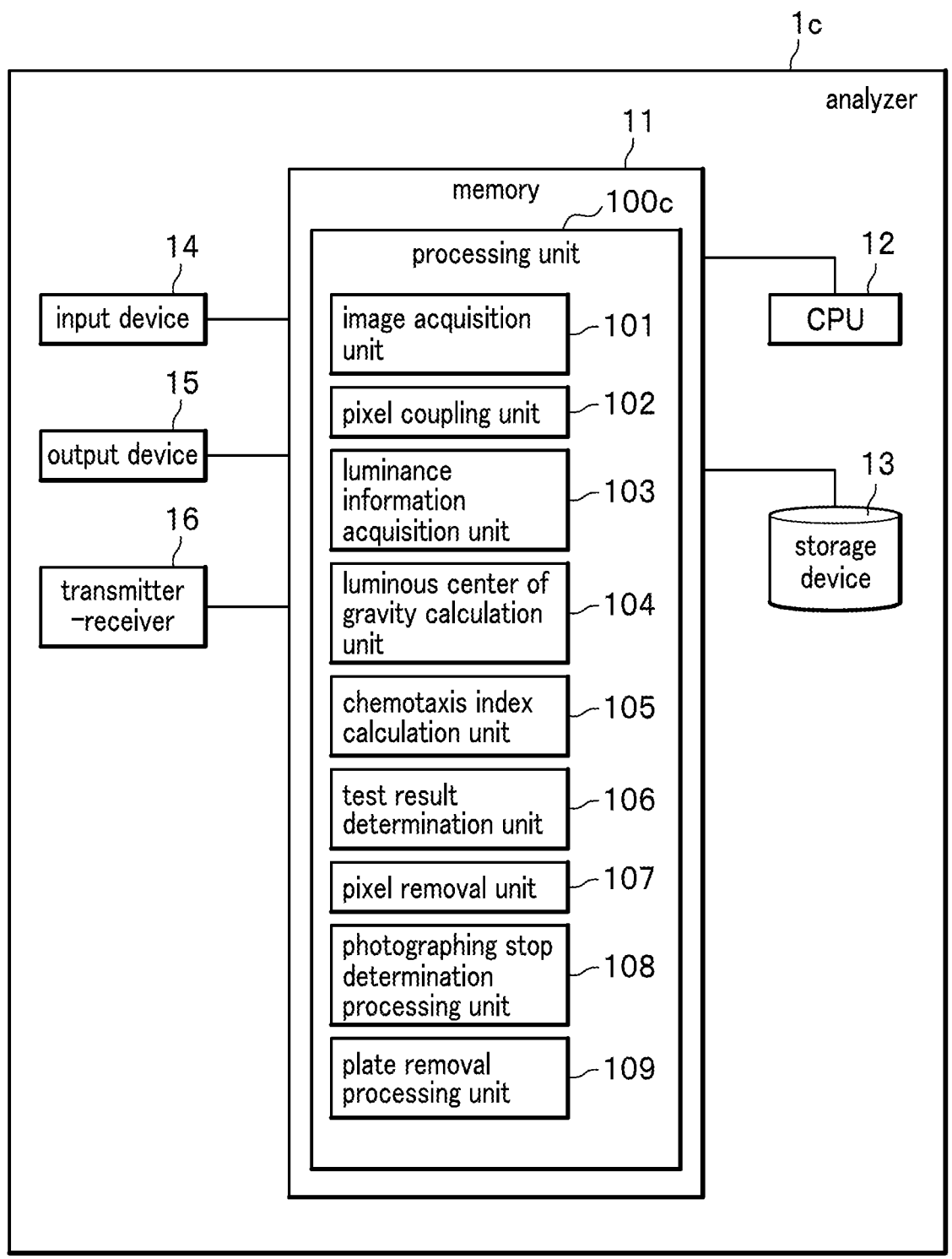
FIG. 30 is a functional block diagram illustrating a configuration of an analyzer according to a fourth embodiment.

FIG. 30 is a functional block diagram illustrating a configuration of an analyzer according to a fourth embodiment.

An analyzer 1c illustrated in FIG. 30 is similar to the analyzer 1b illustrated in FIG. 20, except that a processing unit 100c includes a plate removal processing unit 109 that selects the plate P (FIG. 3) in which no time variation of luminous centers of gravity is shown, as a plate to be removed.

[Flowchart]

Figure 31:
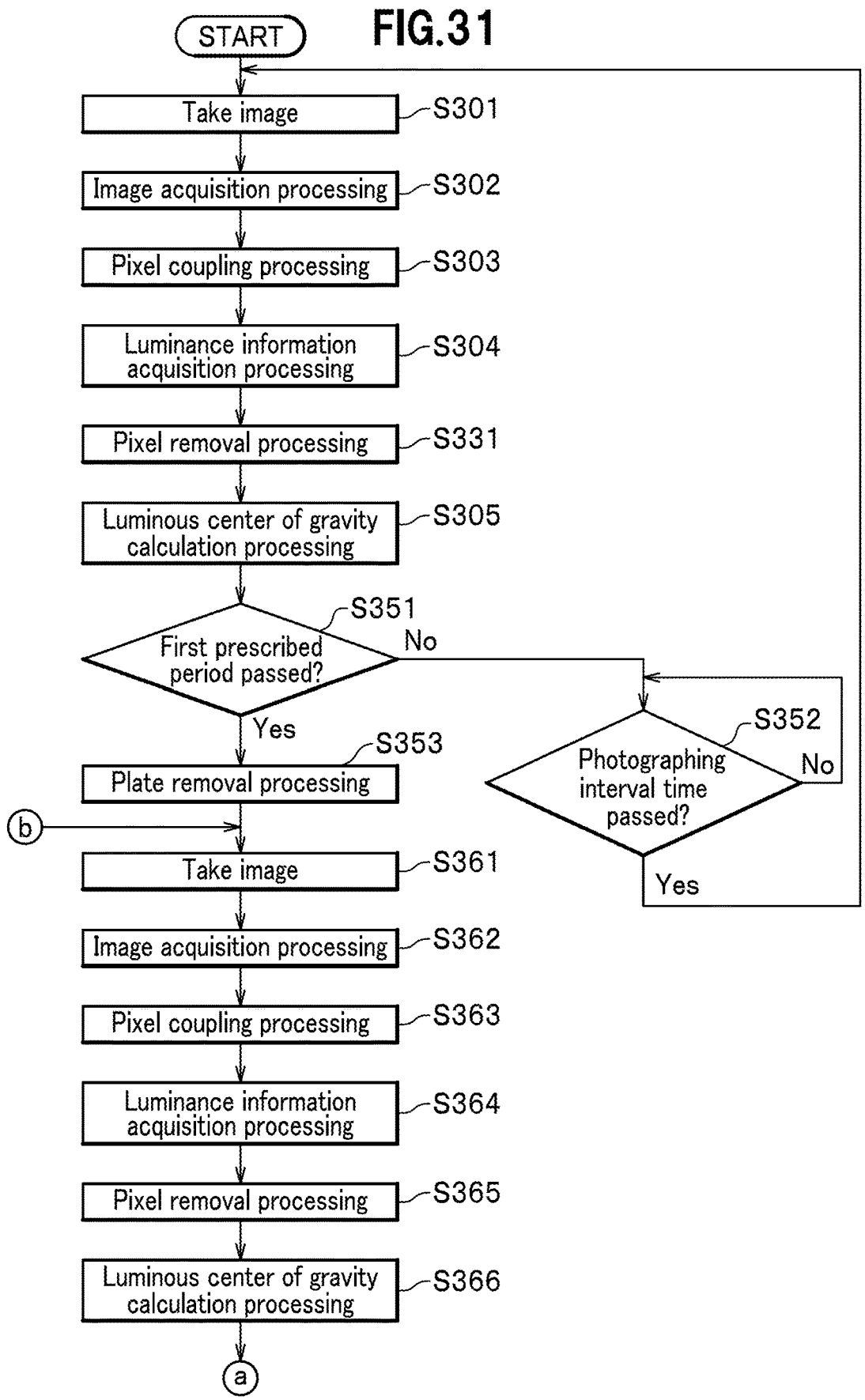
FIG. 31 is a flowchart (part 1) illustrating a procedure of steps performed by the analyzer according to the fourth embodiment.
Figure 32:
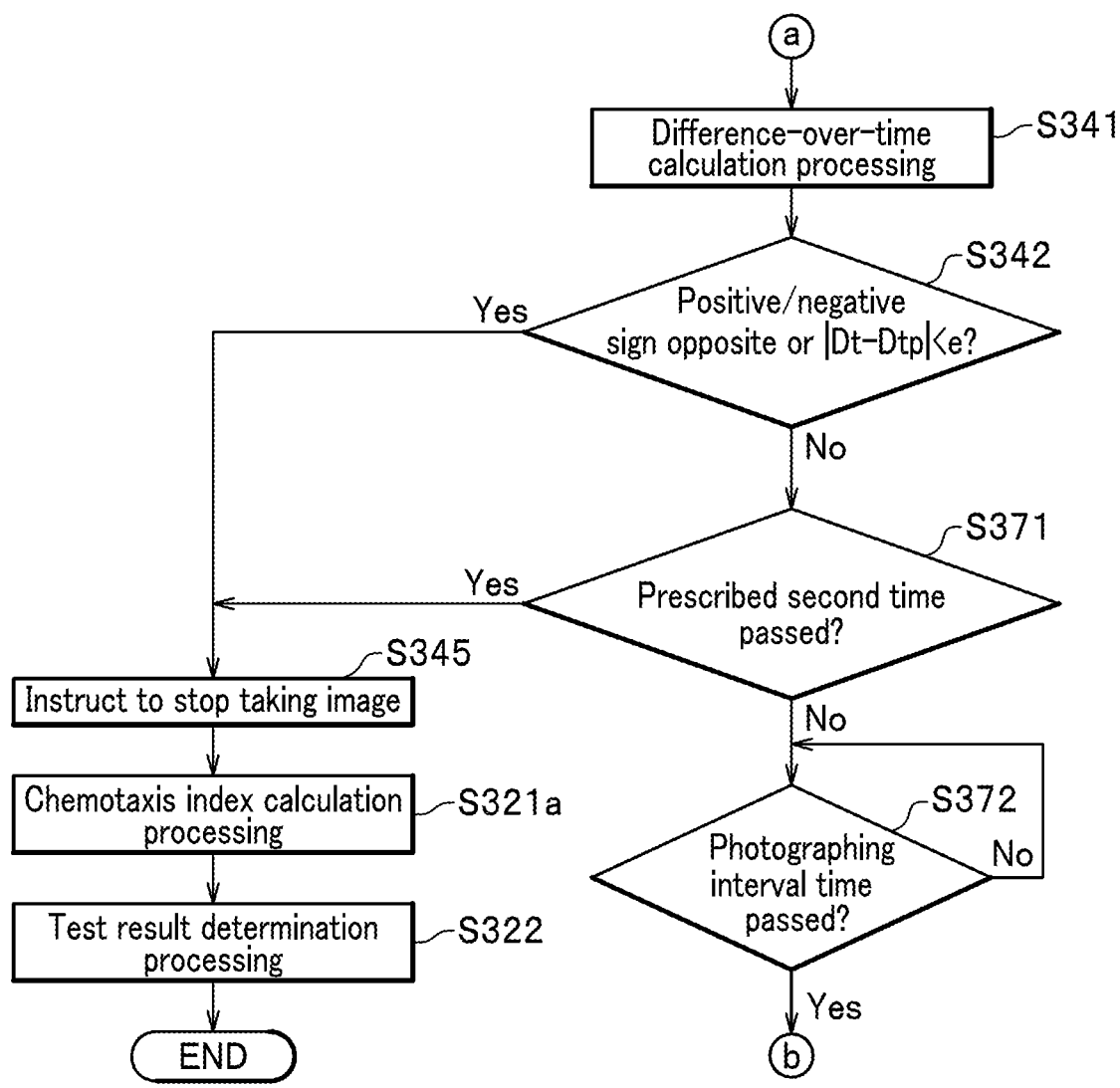
FIG. 32 is a flowchart (part 2) illustrating a procedure of steps performed by the analyzer according to the fourth embodiment.

FIG. 31 and FIG. 32 are a flowchart illustrating a procedure of steps performed by the analyzer according to the fourth embodiment, with reference to FIG. 1 and FIG. 30 where appropriate.

A processing illustrated in FIG. 31 and FIG. 32 is similar to that illustrated in FIG. 21, except the following:

In step S305, after the luminous center of gravity calculation unit 104 calculates a luminous center of gravity, the plate removal processing unit 109 determines whether or not a first prescribed period of time (for example, 2 minutes) has already passed after a chemotaxis is started (S351 in FIG. 31).

If it is determined in step S351 that the first prescribed period of time has not yet passed after the start of the chemotaxis (S351→No), the processing unit 100c determines whether or not a prescribed photographing interval time (for example, 1 minute) has already passed after a previous image has been photographed (S352).

If it is determined in step S352 that the photographing interval time has not yet passed (S352→No), the processing unit 100c returns the processing back to step S352.

If it is determined in step S352 that the photographing interval time has already passed (S352→Yes), the processing unit 100c returns the processing back to step S301, and sends an instruction to the photographing apparatus 2 to take an image of the plate P (FIG. 3).

If it is determined in step S351 that the first prescribed time has already passed after the start of the chemotaxis (S351→Yes), the plate removal processing unit 109 performs the plate removal processing (S353), and the processing unit 100c advances the processing to step S361.

In step S353, the plate removal processing unit 109 issues an instruction such that, the plate P in which a difference between the luminous center of gravity immediately after plotting of the nematodes and that after the first prescribed time has passed is equal to or smaller than a prescribed value is removed from a target to be tested. The removal instruction of the plate P may be outputted to the output device 15 of the analyzer 1c or may be displayed in a display device (not illustrated) installed near the photographing apparatus 2 or the like.

Steps S361 to S366 are similar to steps S301 to S305, and description thereof is omitted herefrom.

If "No" is determined in step S342 (FIG. 32), the photographing stop determination processing unit 108 determines whether or not a second prescribed time (for example, 13 minutes) has already passed after the first prescribed time passed (S371 in FIG. 32).

If it is determined in step S371 that the second prescribed time has already passed (S371→Yes), the photographing stop determination processing unit 108 advances the processing to step S345.

If it is determined in step S371 that the second prescribed time has not yet passed after the start of the chemotaxis (S371→No), the processing unit 100c determines whether or not a prescribed photographing interval time (for example, one minute) has passed after a previous image has been photographed (S372).

If it is determined in step S372 that the photographing interval time has not yet passed (S372→No), the processing unit 100c returns the processing back to step S372.

If it is determined in step S372 that the photographing interval time has already passed (S372→Yes), the processing unit 100c returns the processing back to step S361, and sends an instruction to the photographing apparatus 2 to take an image of the plate P.

Figure 33:
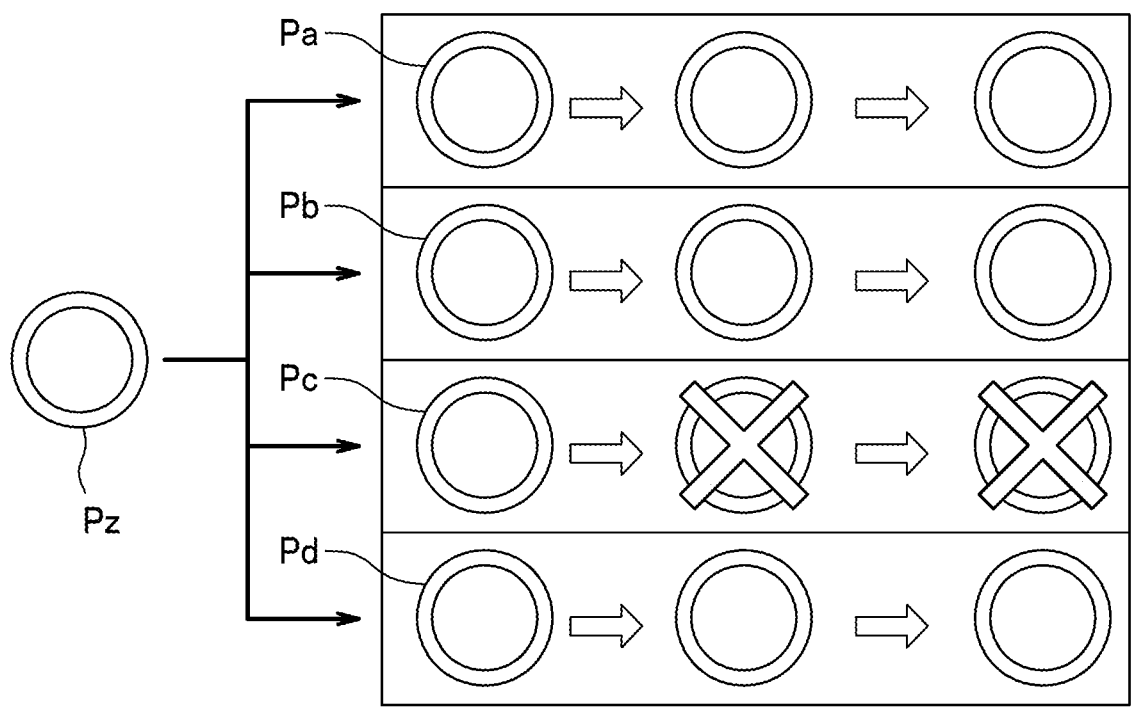
FIG. 33 is a schematic explanatory diagram illustrating a plate removal processing performed in the fourth embodiment.

FIG. 33 is a schematic explanatory diagram illustrating a plate removal processing performed in the fourth embodiment.

FIG. 33 illustrates an example of preparing four analysis plates Pa to Pd from one culture plate Pz. The culture plate Pz used herein is the plate P (FIG. 3) in which nematodes are cultured. The analysis plates Pa to Pd are each the plate P on which a urine sample and nematodes are placed and which is set in the photographing apparatus 2 (FIG. 1).

As illustrated in FIG. 33, the nematodes which have been cultured in the same culture plate Pz are divided into the four analysis plates Pa to Pd.

The four analysis plates Pa to Pd are set in the photographing apparatus 2, has an image thereof taken, are analyzed, and are discarded. The analysis used herein means calculation of a luminous center of gravity and calculation of a chemotaxis index.

Of the plates Pa to Pd, the analysis plate Pc has a value equal to or less than a prescribed value as a distance between a position of a luminous center of gravity immediately after plotting nematodes and a position of a luminous center of gravity after a lapse of a prescribed time. This indicates that the nematodes may become weak, and thus, the analysis plate Pc is not suited for a target to be tested and is thus removed.

In the fourth embodiment, the plate P in which only a small change in the luminous center of gravity is detected even after a lapse of a prescribed time, is removed. This can improve accuracy in test result determination.

Note that the fourth embodiment has a structure composed of the third embodiment with the plate removal processing added thereto. That is, in the fourth embodiment, a luminous center of gravity is calculated at prescribed intervals (for example, every one minute). The present invention is not, however, limited to this. For example, as in the first embodiment and the second embodiment, another configuration is also possible in which: images are taken immediately after plotting nematodes and after a lapse of a prescribed time (for example, after 15 minutes); and, if the plate P has a value of a difference between the luminous centers of gravity immediately after plotting nematodes and after the lapse of the prescribed time, equal to or less than a prescribed value, the plate P is removed.

In the first to fourth embodiments, a chemotaxis index is calculated based on the luminous center of gravity. The present invention is not, however, limited to this, and the chemotaxis index may be calculated based on any information other than the luminous center of gravity, as long as the information is concerning luminance in an image taken by the camera 206. For example, the chemotaxis index may be calculated based on a distance between: a coupled pixel having the highest luminance immediately after plotting nematodes in coupled pixels; and a coupled pixel having the highest luminance, after a lapse of a prescribed time from a start of the chemotaxis.

Graphs, tables, or any other items representing transition of the luminous center of gravity over time, as illustrated in FIG. 10, FIG. 14, FIG. 16, FIG. 17, FIG. 22 to FIG. 29, and FIG. 33 may be outputted to (displayed in) the output device 15.

Fifth Embodiment

When a cancer screening test is actually conducted, it is contemplated that there are two important points, a large-scale test and a quality control. The large-scale test is considered to be basically available by automating chemotaxis and performing parallel processing. In a cancer screening test according to this embodiment, however, nematodes, are used, which are living creatures, and conditions of the nematodes are thought to have a large influence on test results. That is, if nematodes in poor conditions are used, reliability of the test results can be undermined.

Currently, conditions of nematodes are managed by: a culture condition of nematodes such as a culture temperature and a culture time; a chemotaxis condition such as a chemotaxis temperature, a chemotaxis time, and the number of days elapsed after preparing a chemotaxis plate; and the like. It is, however, too difficult to take control of all those conditions.

Under the circumstances as described above in which all the conditions of managing nematodes cannot be controlled, even if only controllable conditions can be managed or optimized, states of the nematodes cannot be completely controlled.

It is thus effective to have a full realization of the states of nematodes, based on how the nematodes migrate when a test is conducted. There has not been, however, considered by which technique the states of nematodes can be known, based on the states of migration of nematodes when a test is conducted.

The first to the fourth embodiments describe the techniques of recognizing the states of nematodes, based on the states of migration of nematodes when a test is conducted. The fifth embodiment proposes a quality control technique in which a time required for a test is shorter and accuracy is higher than those of the first to the fourth embodiments.

[System Configuration]

Figure 34:
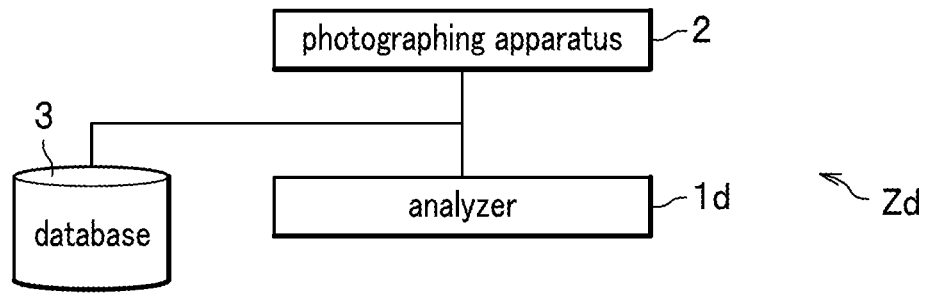
FIG. 34 is a functional block diagram illustrating a configuration of a cancer analysis system according to a fifth embodiment.

FIG. 34 is a functional block diagram illustrating a configuration of a cancer analysis system according to the fifth embodiment.

A cancer analysis system Zd includes an analyzer 1d, a photographing apparatus 2, and a database 3.

The photographing apparatus 2: takes an image of a plate on which nematodes and a urine sample are plotted; and transmits the taken image to the analyzer 1d.

The analyzer 1d acquires luminance information based on the image transmitted from the photographing apparatus 2. The analyzer 1d determines a quality state of the nematodes, based on the acquired luminance information. If the analyzer 1d determines that the quality state of the nematodes is good, the analyzer 1d calculates a chemotaxis index of the nematodes based on the acquired luminance information. The calculated chemotaxis index is used for determining positivity or negativity for cancer. The quality state and the chemotaxis index used herein will be described hereinafter.

The database 3 stores therein a time variation of a relative luminance number in a chemotaxis assay area to be described hereinafter, or the like.

[Analysis Apparatus]

Figure 35:
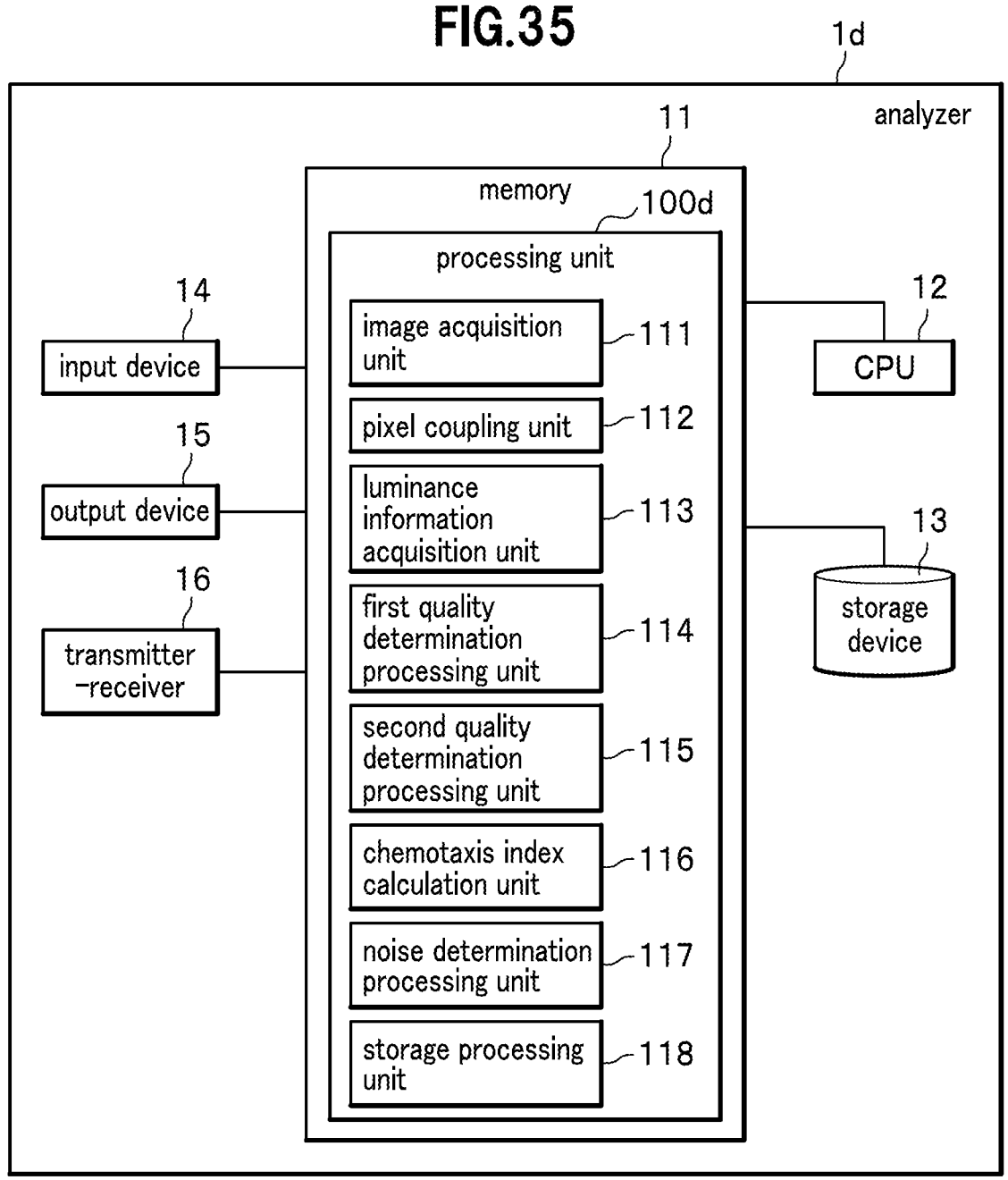
FIG. 35 is a functional block diagram illustrating a configuration of an analyzer according to the fifth embodiment.

FIG. 35 is a functional block diagram illustrating a configuration of an analyzer according to the fifth embodiment.

An analyzer 1d: is realized by a PC (Personal Computer) or the like; and includes a memory 11, a CPU (Central Processing Unit) 12, a storage device 13, an input device 14, an output device 15, and a transmitter-receiver 16.

A program stored in the storage device 13 is loaded into the memory 11. The CPU 12 executes the loaded program. The aforementioned allows to realize the processing unit 100d; and an image acquisition unit 111, a pixel coupling unit 112, and a luminance information acquisition unit 113, each of the latter constituting the processing unit 100d. The aforementioned also allows to realize a first quality determination processing unit (a quality control unit) 114, a second quality determination processing unit (a quality control unit) 115, a chemotaxis index calculation unit 116, a noise determination processing unit 117, and a storage processing unit 118.

The image acquisition unit 111, the pixel coupling unit 112, and the luminance information acquisition unit 113 perform similar processings to the image acquisition unit 101, the pixel coupling unit 102, and the luminance information acquisition unit 103 illustrated in FIG. 2, respectively, and description thereof is omitted herefrom.

The first quality determination processing unit 114 makes a determination on a first quality control to be explained hereinafter.

The second quality determination processing unit 115 makes a determination on a second quality control to be explained hereinafter.

The chemotaxis index calculation unit 116 calculates a chemotaxis index for determining positivity or negativity for cancer. The chemotaxis index will be explained hereinafter.

The noise determination processing unit 117 determines whether or not a result determined by the second quality determination processing unit 115 is caused by noise.

The storage processing unit 118 stores a time variation of a relative luminance number (to be described hereinafter) in a chemotaxis assay area to be described hereinafter, or the like, in the database 3 (FIG. 34).

<Areas>

Figure 36:
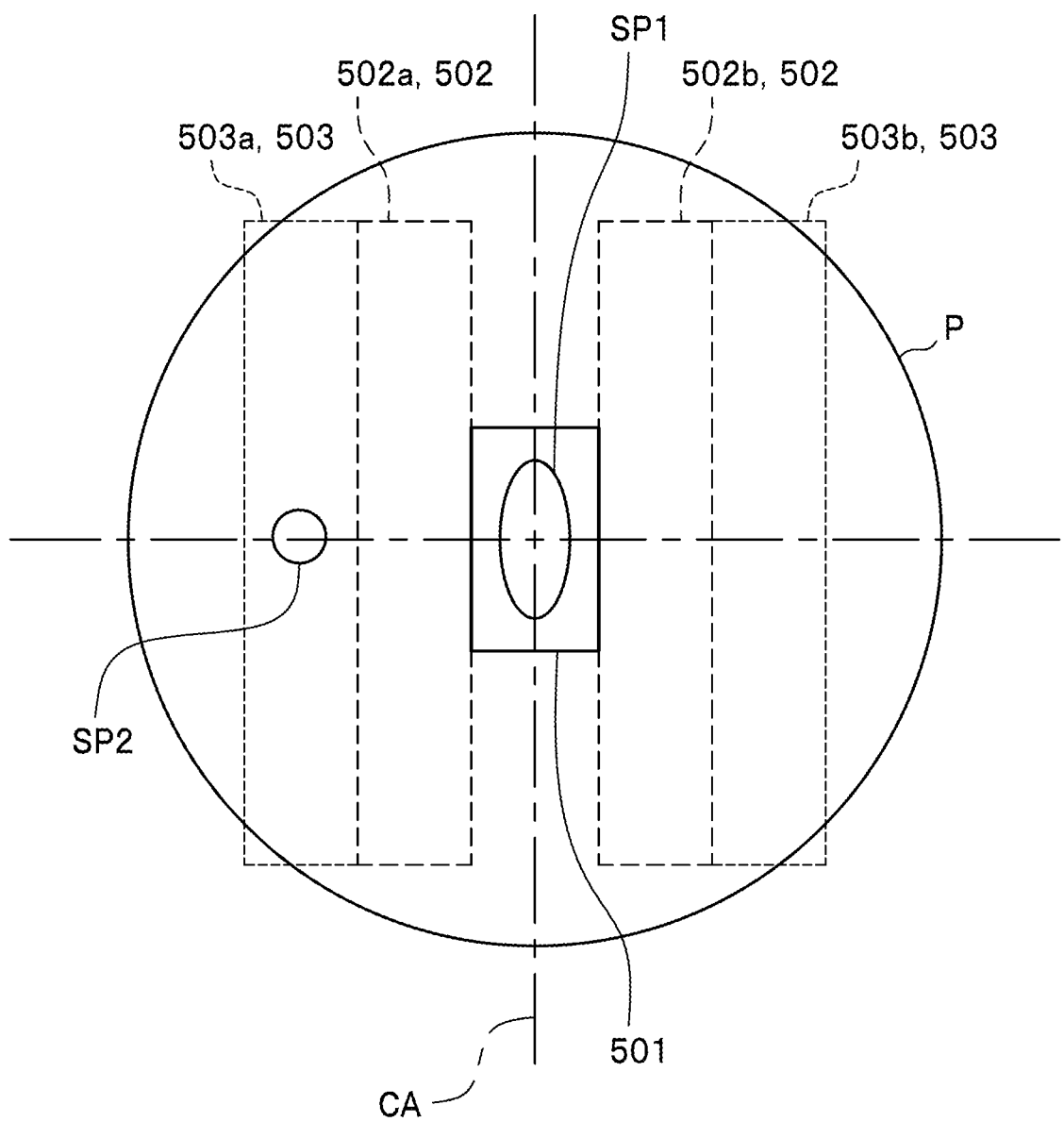
FIG. 36 is a diagram illustrating areas set in a quality control method performed in the fifth embodiment.

FIG. 36 is a diagram illustrating areas set in a quality control method performed in the fifth embodiment.

More specifically, FIG. 36 illustrates an image in which the plate P is photographed.

A reference numeral SP1 represents a point in which nematodes are plotted. A reference numeral SP2 represents a point in which a urine sample is plotted.

A first quality control area (a prescribed range, a prescribed area) 501 containing the reference numeral SP1 is an area used in a first quality control processing. A second quality control area (a prescribed range) 502 is an area used in a second quality control processing. A chemotaxis assay area 503 is an area used in a chemotaxis assay.

The second quality control area 502 includes: an attractant side quality control area (a prescribed range) 502a on a side nearer to the urine sample plotted point SP2; and a repellent side quality control area (a prescribed range) 502b which is situated farther from the urine sample plotted point SP2. As illustrated in FIG. 36, the attractant side quality control area 502a and the repellent side quality control area 502b are disposed to have a line symmetry relation with respect to a central axis CA of the plate.

Similarly, the chemotaxis assay area 503 includes: an attractant side chemotaxis assay area 503a on the side nearer to the urine sample plotted point SP2; and a repellent chemotaxis assay area 503b farther from the urine sample plotted point SP2. As illustrated in FIG. 36, the attractant side chemotaxis assay area 503a and the repellent chemotaxis assay area 503b are disposed to have a line symmetry relation with respect to the central axis CA of the plate.

Next is described a relative luminance number used in the fifth embodiment. The relative luminance number is a value calculated by formula (7) shown below.

Relative luminance number=Sum of luminance numbers in area (prescribed range) of interest/Sum of luminance numbers in all areas of image    (7)

In formula (7), a sum of the luminance numbers in an area of interest is divided by a sum of the luminance numbers in all of the areas of the image. This is because the luminance numbers in all of the areas of the image vary over time. Such variation is caused when nematodes lay on top of each other, or the like.

Note that the "number of pixels" in formula (7) is the "number of coupled pixels".

In this embodiment, the sum of luminance numbers is used. Alternatively, the number of white pixels may be counted and used. The technique of using the sum of luminance numbers can increase accuracy in quality control and chemotaxis assay while the technique of counting the number of white pixels can reduce processing load.

In the fifth embodiment: a relative luminance number on an attractant side is indicated by a positive value; and a relative luminance number on a repellent side, a negative value. A relative luminance number in the first quality control is indicated by a positive value.

[Flowchart]

Figure 37:
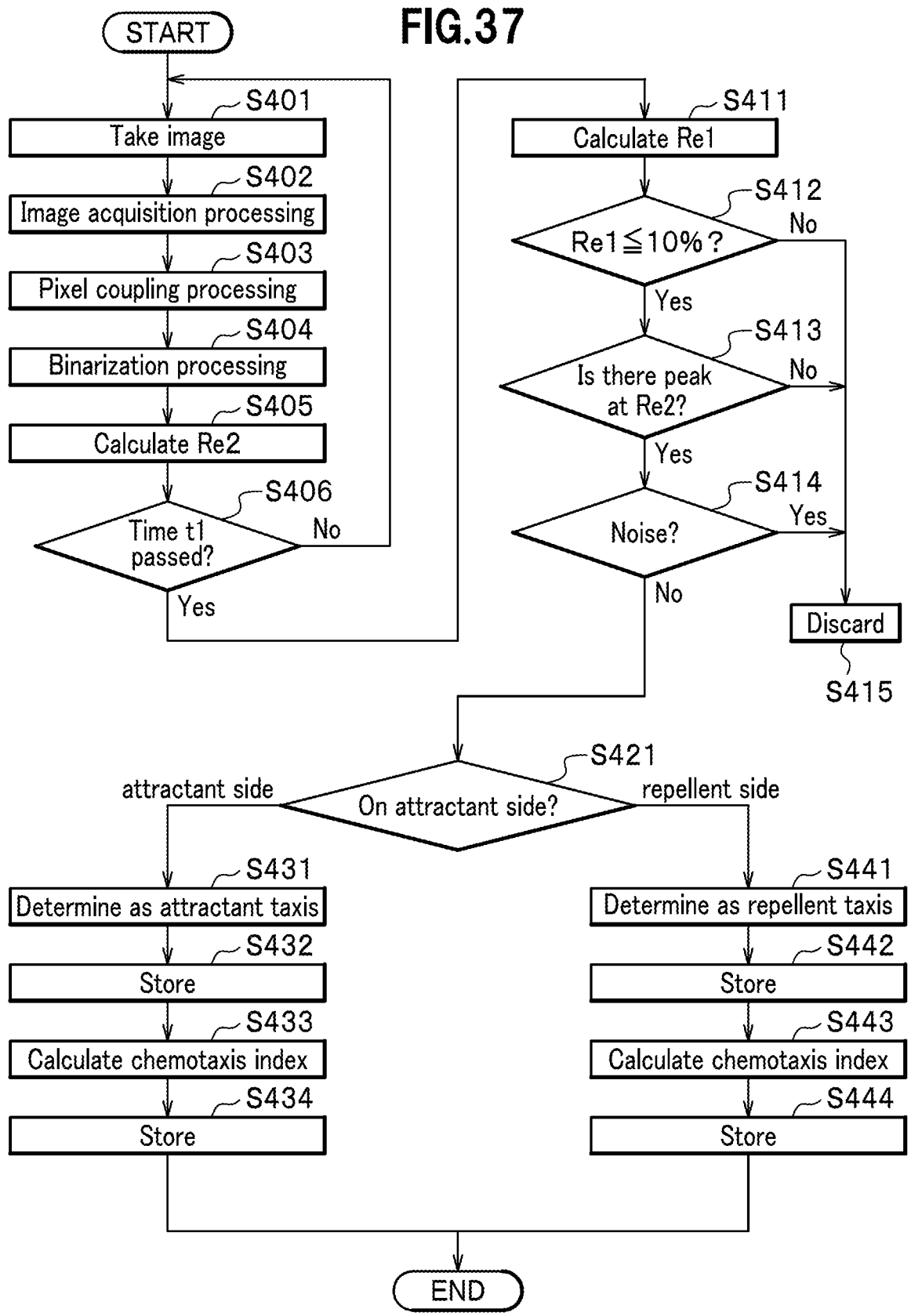
FIG. 37 is a flowchart illustrating a procedure of steps performed by a cancer analysis system according to the fifth embodiment.

FIG. 37 is a flowchart illustrating a procedure of steps performed by a cancer analysis system according to the fifth embodiment. FIG. 34 to FIG. 36 are also referenced where appropriate.

The camera 206 of the photographing apparatus 2 takes an image of the plate P (S401).

The image acquisition unit 101 of the analyzer 1d acquires the image from the photographing apparatus 2, as an image acquisition processing (S402).

The pixel coupling unit 102 performs a pixel coupling processing (S403). Note that step S403 can be omitted.

The luminance information acquisition unit 103 performs a binarization processing to a pixel coupled in step S403 (a coupled pixel) (S404). That is, the luminance information acquisition unit 103: determines a coupled pixel having a luminance number equal to or more than a prescribed number, as a white pixel; and also determines a coupling pixel having a luminance number less than the prescribed number, as a black pixel. Note that step S404 is performed only when the number of white pixels is used as the relative luminance number. When a sum of luminance numbers is used as the relative luminance number, step S404 is omitted.

The second quality determination processing unit 115: acquires luminance information from the coupled pixel; and calculates a relative luminance number Re2 in the second quality control area 502 (S405). Note that, in step S405, the second quality determination processing unit 115 calculates respective relative luminance numbers in the attractant side quality control area 502a and the repellent side quality control area 502b. The second quality determination processing unit 115 stores the calculated relative luminance number Re2 in the database 3.

Note that, when a sum of luminance numbers is used as the relative luminance number, the luminance information is the luminance number. When the number of white pixels is used as the relative luminance number, the luminance information is the number of white pixels.

The processing unit 110d determines whether or not a prescribed time t1 (for example, 5 minutes) has already passed after a start of measurement (S406).

If it is determined in step S406 that the prescribed time t1 has not yet passed (S406→No), the processing unit 100d returns the processing back to step S401.

If it is determined in step S406 that the prescribed time t1 has already passed (S406→Yes), the first quality determination processing unit 114 calculates a relative luminance number in the first quality control area 501 (S411).

The first quality determination processing unit 114 determines whether or not a calculated relative luminance number Re1 is equal to or less than 10% (S412). Note that a threshold in step S412 is not limited to 10%. The threshold may be determined using a machine learning technique. Determination of the threshold using the technique makes it possible to utilize a large volume of accumulated data, to thereby determine a threshold with which a high accuracy rate can be obtained.

If it is determined in step S412 that the relative luminance number Re1 is more than 10% (S412→No), the processing unit 100d: determines that there is a problem in the state of nematodes; and discards the acquired information (S415). The cancer analysis system Zd stops a test of the plate P as a target to be tested.

If it is determined in step S412 that the relative luminance number Re1 is equal to or less than 10% (S412→Yes), the second quality determination processing unit 115 determines whether or not a peak at the relative luminance number Re2 is shown within the prescribed time t1 (S413). In step S413, the second quality determination processing unit 115 determines whether or not a peak at the relative luminance number Re2 is shown in each of the attractant side quality control area 502a and the repellent side quality control area 502b. If it is determined that there is a peak either in the attractant side quality control area 502a or in the repellent side quality control area 502b, the second quality determination processing unit 115 determines "Yes" in step S413.

If it is determined in step S413 that no peak is shown at the relative luminance number Re2 (S413→No), the processing unit 100d: determines that there is a problem in quality; and discards the acquired information (S415). The cancer analysis system Zd stops a test of the plate P as a target to be tested.

If it is determined in step S413 that a peak is shown at the relative luminance number Re2 (S413→Yes), the noise determination processing unit 117 determines whether or not the detected peak at the relative luminance number Re2 is noise (S414). Whether or not it is noise is determined by, for example, whether or not a relative luminance number in the chemotaxis assay area 503 after a lapse of the prescribed time t1 from the start of measurement is less than the prescribed value. That is, if the relative luminance number in the chemotaxis assay area 503 after the lapse of the prescribed time t1 from the start of measurement is less than a prescribed value, the noise determination processing unit 117 determines that the peak at the relative luminance number Re2 is noise. Determination on noise will be detailed hereinafter.

If it is determined in step S414 that the peak is noise (S414→No), the processing unit 100d determines that there is a problem in quality; and discards the acquired information (S415). The cancer analysis system Zd stops a test of the plate P as a target to be tested.

If it is determined in step S414 (S414→Yes), the second quality determination processing unit 115 determines whether or not the detected peak at the relative luminance number Re2 is detected on the attractant side (S421).

If it is determined in step S421 that the peak is detected on the attractant side (S421→attractant side), the chemotaxis index calculation unit 116 determines that the sample has attractant taxis (S431).

The storage processing unit 118 stores the relative luminance numbers Re1, Re2, and a time variation of the relative luminance number in the attractant side chemotaxis assay area 503a, in the database 3 (S432).

The chemotaxis index calculation unit 116 calculates the relative luminance number in the attractant side chemotaxis assay area 503a at time t1, as a chemotaxis index (S433). The storage processing unit 118 then stores the chemotaxis index calculated in step S433, as data paired with the information stored in step S432, in the database 3 (S434).

If it is determined in step S421 that the peak is detected on the repellent side (S421→repellent side), the chemotaxis index calculation unit 116 determines that the sample has repellent taxis (S441).

The storage processing unit 118 stores the relative luminance numbers Re1, Re2 and a time variation of the relative luminance number in the repellent chemotaxis assay area 503b, in the database 3 (S442).

The chemotaxis index calculation unit 116 calculates the relative luminance number in the repellent chemotaxis assay area 503b at time t1, as a chemotaxis index (S443). The storage processing unit 118 then stores the chemotaxis index calculated in step S443, as data paired with the information stored in step S442, in the database 3.

Note that step S401 in FIG. 37 corresponds to step S212 in FIG. 6B. Steps S402 to S433 and S441 to S443 in FIG. 37 correspond to step S213 in FIG. 6B. Steps S433 and S443 in FIG. 37 correspond to step S214 in FIG. 6B. And, steps S434 and S444 in FIG. 37 correspond to step S215 in FIG. 6B.

<Test Data>

Figure 38:
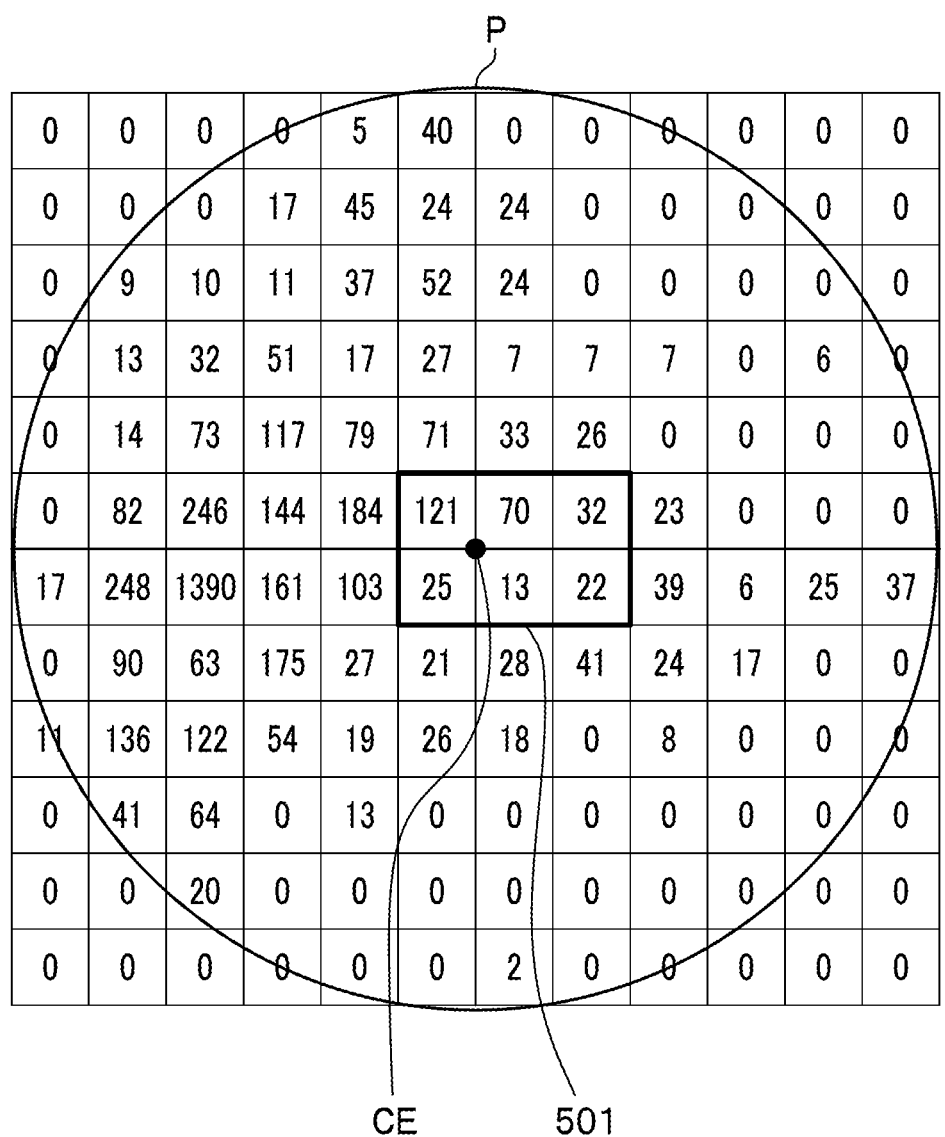
FIG. 38 is a diagram illustrating a relationship between actually acquired luminance information and the first quality control area.

FIG. 38 is a diagram illustrating a relationship between actually acquired luminance information and the first quality control area.

In FIG. 38, luminance numbers for each of coupling pixels are shown as the luminance information. The coupling pixel used herein is an approximately 6.8 mm square. A specimen is plotted in a position having a distance of 25 mm from the center CE of the plate P. The luminance number used herein is a luminance number after 5 minutes from the start of measurement. Test data that follows uses a sum of luminance numbers as the relative luminance number.

The first quality control area 501 is set in a position slightly closer to the repellent side. As described above, in plotting nematodes, the nematodes are plotted accompanied by buffer. The plate P is then tilted on the repellent side so as to remove the buffer. In this way, only the buffer is flown away on the repellent side, and the nematodes stay in the plotted point, though slightly closer to the repellent side. Therefore, the first quality control area 501 is set in the position slightly closer to the repellent side from the center CE of the plate P.

FIG. 39 is a diagram illustrating a relationship between the actually acquired luminance information, the second quality control area, and the chemotaxis assay area.

In FIG. 39, luminance numbers for each of coupling pixels are shown as the luminance information. The luminance numbers shown in FIG. 39 are same as those shown in FIG. 38.

With those luminances described above, the second quality control area 502 (502a, 502b) and the chemotaxis assay area 503 (503a, 503b) are arranged.

In the fifth embodiment, as described in steps S434 and S444 in FIG. 37, not an image data acquired in step S402 or the luminance information illustrated in FIG. 38 or FIG. 39 but a time variation of the relative luminance number in the chemotaxis assay area 503 or the like is stored in the database 3. This makes it possible to reduce a volume of information stored in the database 3.

In summary, the quality control techniques in the fifth embodiment are as follows:

(1) A state of migration of nematodes is used as a quality control index, to thereby enable a one-hundred percent test.

(2) A quality control index is set based on another idea that a degree of migration of nematodes should basically fall within an appropriate range when a lot used meets appropriate culture and chemotaxis conditions. That is, if nematodes plotted in a central portion of the plate P are in good condition, a luminance number of an area in an image in which the nematodes are plotted (the first quality control area 501) should drastically reduced. This is referred to as a first quality control index.

(3) A time variation of luminance numbers in each of both areas neighboring the area in which the nematodes are plotted (the second quality control area 502) is as described below. If the nematodes are in good condition, a peak of the luminance number in the area should appear within a certain period of time. This is because, when the nematodes pass through the area, the number of the nematodes is once increased in the second quality control area 502, and then, the nematodes migrate toward the chemotaxis assay area 503. The time variation of the luminance number in the area of interest (the second quality control area 502) can be thus used as a quality control index. This is referred to as a second quality control index.

(4) As described above, the chemotaxis assay area 503 is arranged on an outer side of the second quality control area 502. This makes it possible to obtain a chemotaxis index on the attractant side or on the repellent side situated opposite thereto.

Next is described a test result of an actual urine sample. FIG. 36 is referenced where appropriate.

[Case of Attraction: Urine Sample of Cancer Patient]
(First Quality Control)

Figure 40:
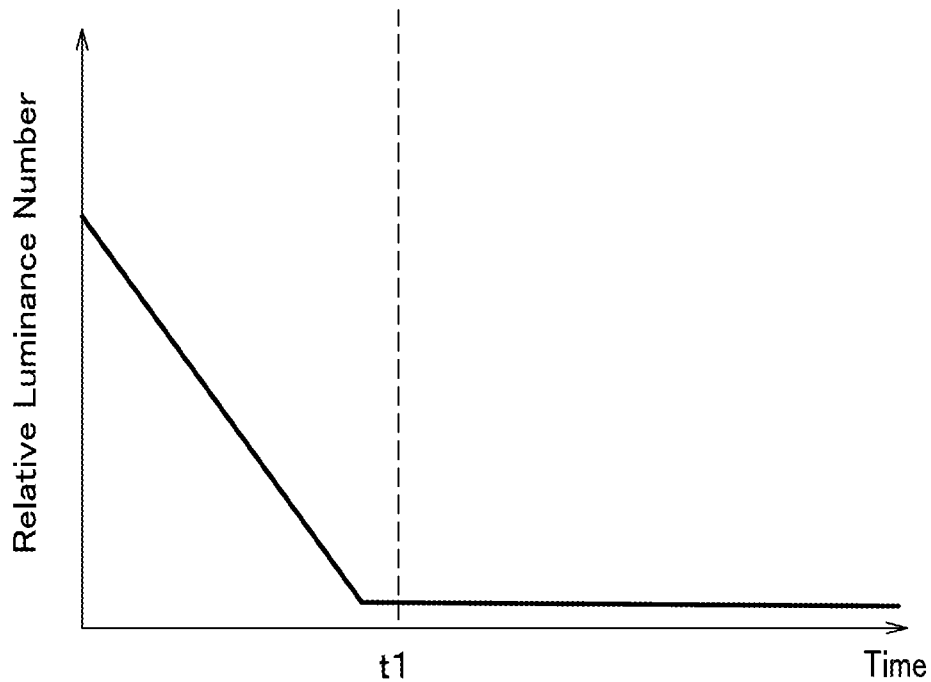
FIG. 40 is a diagram (part 1) illustrating a time variation of the relative luminance number in the first quality control area.

FIG. 40 is a diagram illustrating a time variation of the relative luminance number in the first quality control area illustrated in FIG. 36.

Note that, in each of FIG. 40 to FIG. 52, a vertical axis represents a relative luminance number, and a horizontal axis represents a time.

Herein, "Area of interest" in formula (7) is "First quality control area 501".

In FIG. 40, the relative luminance number: starts decreasing at time 0 (a time when a chemotaxis of nematodes is started); is lowered to approximately 0 just before at time t1; and is then leveled off.

This means that the nematodes have gone away from the first quality control area 501 illustrated in FIG. 36. If a period of time from time 0 to time t1 (a first period of time) is short enough, this also means that the nematodes are in good condition. If the nematodes are not in good condition, the nematodes keep on staying around the plotted point SP1, and the relative luminance number will not become lower. Note that t1=5 minutes according to experiments carried out by the inventors.

(Second Quality Control and Chemotaxis Assay)

Figure 41:
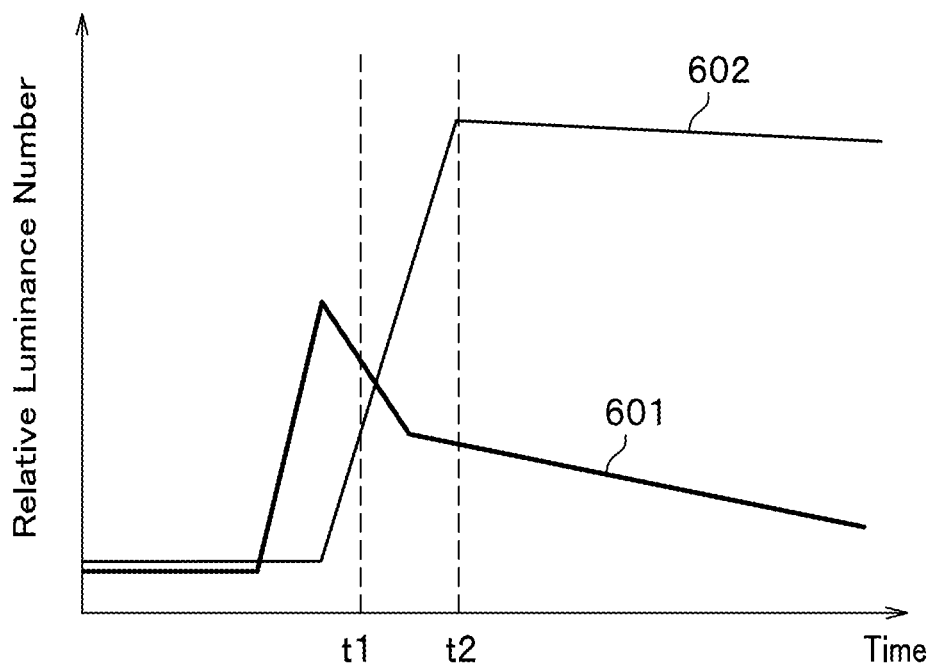
FIG. 41 is a diagram illustrating a time variation in the relative luminance number in the second quality control area and the chemotaxis assay area.

FIG. 41 is a diagram illustrating a time variation in the relative luminance number in the second quality control area and the chemotaxis assay area.

Herein, the second quality control area 502 of interest is the attractant side quality control area 502a. The chemotaxis assay area 503 of interest is the attractant side chemotaxis assay area 503a.

A reference numeral 601 represents a time variation of the relative luminance number in the attractant side quality control area 502a. A reference numeral 602 represents a time variation of the relative luminance number in the attractant side chemotaxis assay area 503a.

Note that the relative luminance number of the reference numeral 601 corresponds to "Area of interest"="Attractant side quality control area 502a" in formula (7). The relative luminance numbers on the reference numeral 602 corresponds to "Area of interest"="attractant side chemotaxis assay area 503a" in formula (7).

A graph of the reference numeral 601: shows a peak just before time t1; and is gradually decreased. A graph of the reference numeral 602 keeps on moving upward from time 0 (at the start of the chemotaxis) to time t2 (t2>t1 (a second time)); and is then leveled off.

This is because the nematodes pass through the attractant side quality control area 502a and reach the attractant side chemotaxis assay area 503a.

Note that t1=5 minutes and t2=10 minutes according to experiments carried out by the inventors.

As described above, in the fifth embodiment, firstly, if the luminance number in the first quality control area 501 becomes approximately 0 within a prescribed period of time, the state of the nematodes is determined to be in good condition. This makes it possible to confirm that the plotted nematodes do not keep on staying around the plotted point SP1.

After the above-described first quality control processing, the luminance number in the second quality control area 502 shows a peak within a prescribed time, the state of the nematodes is determined to be in good condition. This makes it possible to confirm that the nematodes are migrating on the attractant side, in addition to the migration away from the plotted point within the prescribed time as a result of the first quality control processing.

Thus, there is no problem in that a chemotaxis assay index is calculated at time t1 in FIG. 41. Note that the chemotaxis assay index is herein indicated by the relative luminance numbers in the attractant side chemotaxis assay area 503a at time t1.

Next is described in detail significance of the second quality control with reference to FIG. 36.

In the first quality control, whether or not the nematodes are away from the first quality control area 501 is determined. That is, in the first quality control area 501, whether or not the nematodes keep on staying around the plotted point SP1 is determined. Such migration of the nematodes from around the plotted point SP1 does not always mean that the nematodes migrate on the attractant side or the repellent side. For example, the nematodes may migrate in an upward or a downward direction with respect to the plane of FIG. 36. For example, when a tester has the plate P with his/her hand, a temperature of a portion which is touched by the hand is raised. The nematodes have a behavior of migrating toward a lower temperature. When the plate P is touched by the hand, the nematodes may not appropriately migrate toward the attractant side or the repellent side.

Therefore, in the fifth embodiment, the second quality determination processing unit 115 determines whether or not the nematodes have passed through, based on whether or not the relative luminance number in the second quality control area 502 shows a peak within a prescribed time. This makes it possible to determine whether or not the nematodes are migrating toward the attractant side or the repellent side.

(Actual Data; First Quality Control Area)

Figure 42:
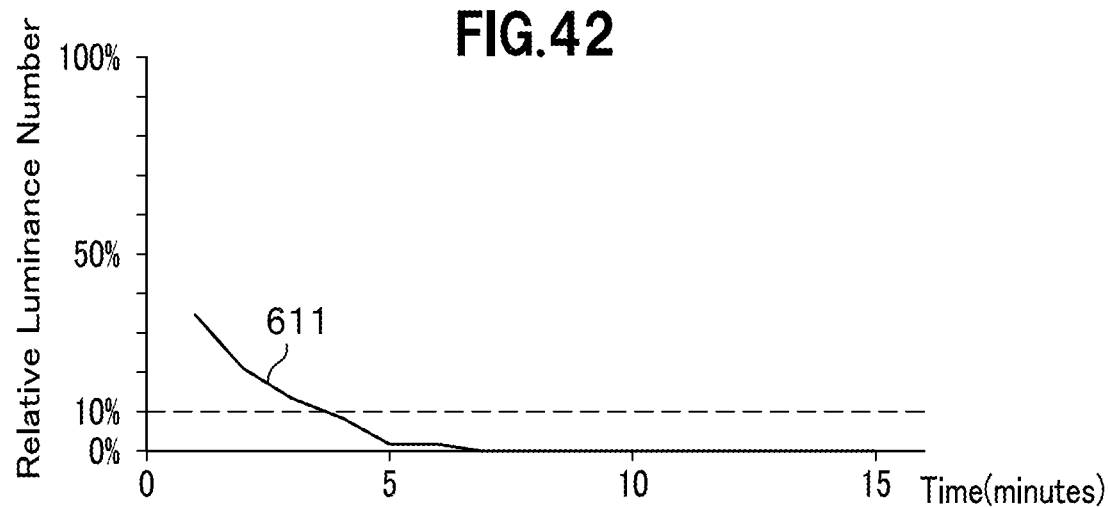
FIG. 42 is a diagram illustrating a time variation of the relative luminance number in the first quality control area, using a urine sample of a cancer patient based on actual data.

FIG. 42 is a diagram illustrating a time variation of the relative luminance number in the first quality control area, using a urine sample of a cancer patient based on actual data.

Figure 43:
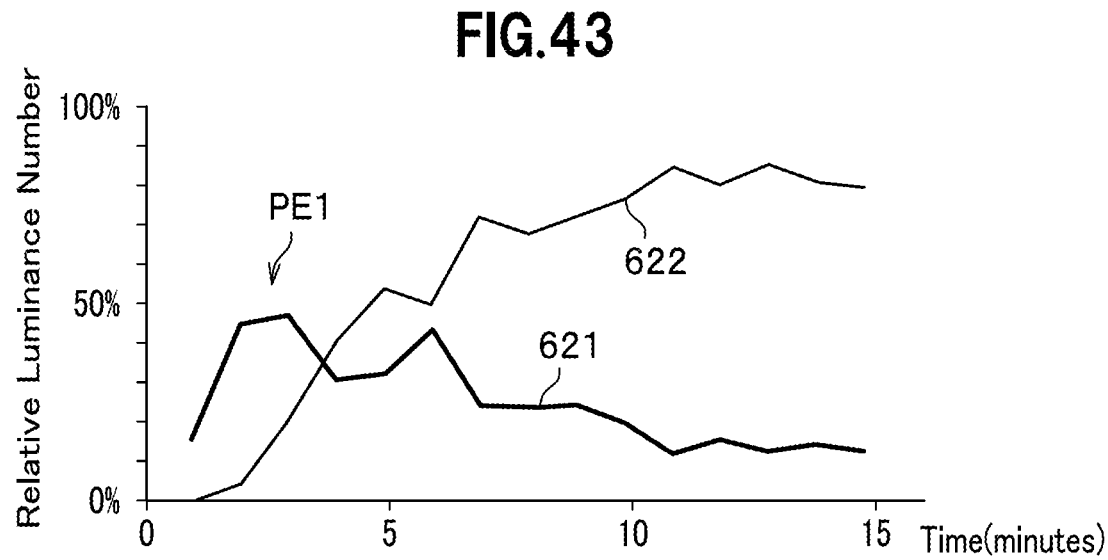
FIG. 43 is a diagram illustrating a time variation of the relative luminance number in the attractant side quality control area and the attractant side chemotaxis assay area, using a urine sample of a cancer patient based on actual data.
Figure 44:
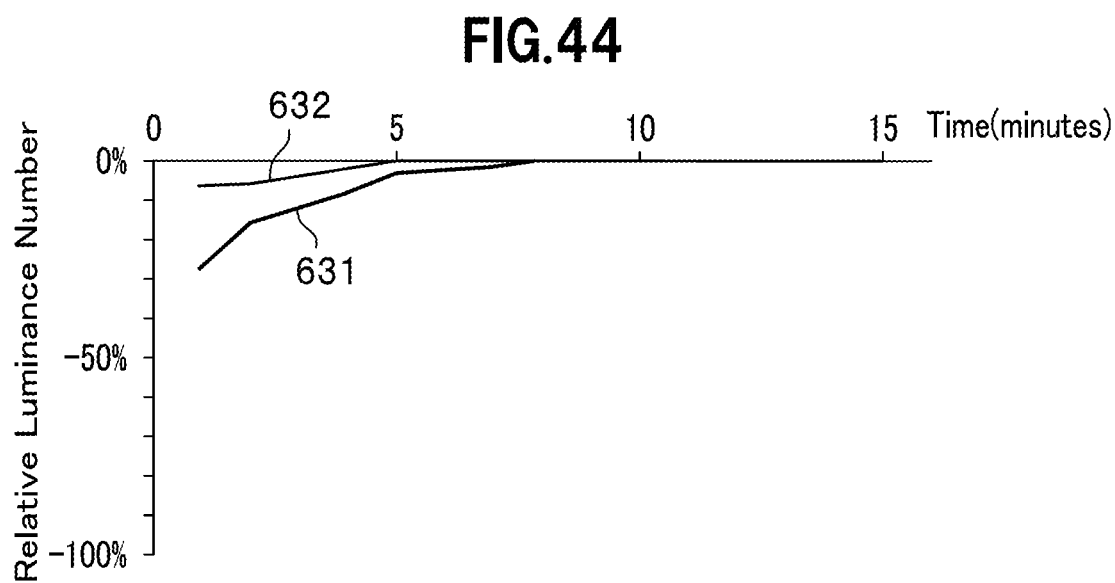
FIG. 44 is a diagram illustrating a time variation of the relative luminance number in the repellent side quality control area and the repellent side chemotaxis assay area, using a urine sample of a cancer patient based on actual data.

A graph illustrated in each of FIG. 42 to FIG. 44 shows a test result using the urine sample of the cancer patient.

As shown in a graph 611, the relative luminance number is decreased to a 10% after 5 minutes from a start of measurement (at a time of 0 minutes). This makes it possible to determine that a state of the nematodes used is in good condition.

(Actual Data: Attractant Side Quality Control Area and Attractant Side Chemotaxis Assay Area)

FIG. 43 is a diagram illustrating a time variation of the relative luminance number in the attractant side quality control area and the attractant side chemotaxis assay area, using a urine sample of a cancer patient based on actual data.

A graph 621 shows a time variation of the relative luminance number in the attractant side quality control area 502a when the urine sample of the cancer patient is used. Similarly, a graph 622 shows a time variation of the relative luminance number in the attractant side chemotaxis assay area 503a when the urine sample of the cancer patient is used.

In the graph 621, a peak PE1 appears within 5 minutes after the start of measurement (at time 0). In the graph 621, the relative luminance numbers are decreased after the peak PE1.

In the graph 622, the relative luminance numbers basically keep on rising after the start of measurement (at time 0).

It is thus confirmed that the nematodes have passed through the attractant side quality control area 502a and reach the attractant side chemotaxis assay area 503a. This makes it possible to determine that the state of the nematodes used is in good condition.

(Actual Data: Repellent Side Quality Control Area and Repellent Side Chemotaxis Assay Area)

FIG. 44 is a diagram illustrating a time variation of the relative luminance number in the repellent side quality control area and the repellent side chemotaxis assay area, using a urine sample of a cancer patient based on actual data.

A graph 631 shows a time variation of the relative luminance number in the repellent side quality control area 502b, using the urine sample of the cancer patient. Similarly, a graph 632 shows a time variation of the relative luminance number in the repellent chemotaxis assay area 503b, using the urine sample of the cancer patient.

Note that, in FIG. 44, the relative luminance number is indicated by a negative value so as to represent the repellent side.

As illustrated in FIG. 44, in both the graph 631 and the graph 632, the relative luminance number: shows a negative value after the start of measurement (at time 0); and becomes 0 in due course.

This shows that the nematodes wander into the repellent side and then migrate toward the attractant side.

[Case of Repellent: Urine Sample of Healthy Subject]
(First Quality Control)

Figure 45:
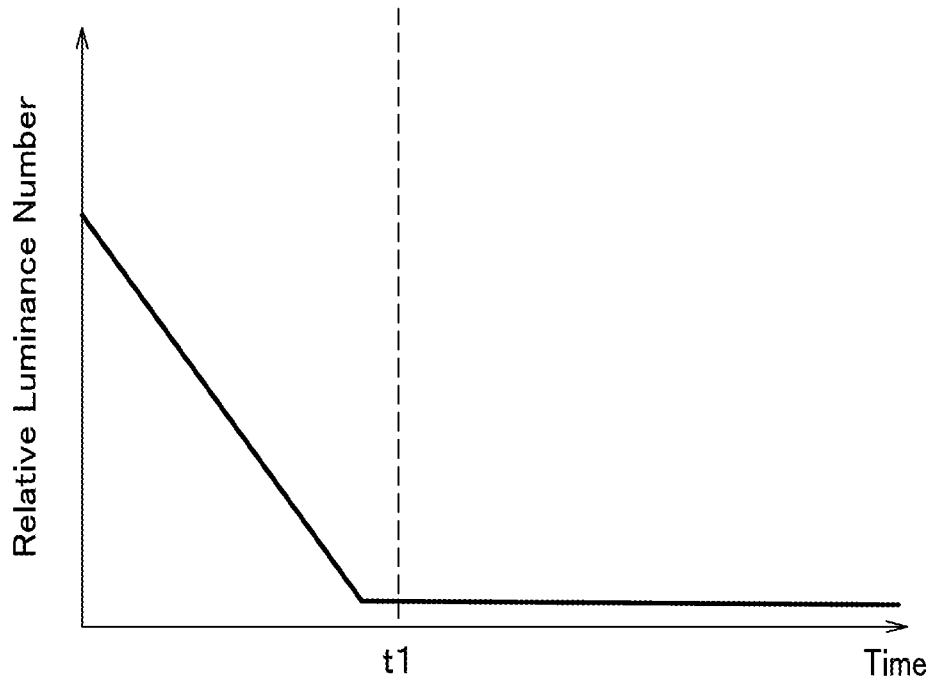
FIG. 45 is a diagram (part 1) illustrating a time variation of the relative luminance number in the first quality control area.

FIG. 45 shows a time variation of the relative luminance number in the first quality control area illustrated in FIG. 36.

In FIG. 45, a vertical axis represents a relative luminance number, and a horizontal axis represents a time.

Herein, "Area of interest" in formula (7) is "First quality control area 501".

In FIG. 45, similarly to FIG. 40, the relative luminance numbers are decreased from time 0 (a time when the nematodes chemotaxis is started) and the relative luminance number becomes approximately 0; and is then leveled off.

This means that, similarly to FIG. 40, the nematodes have gone away from the first quality control area 501 illustrated in FIG. 36.

(Second Quality Control and Chemotaxis Assay)

Figure 46:
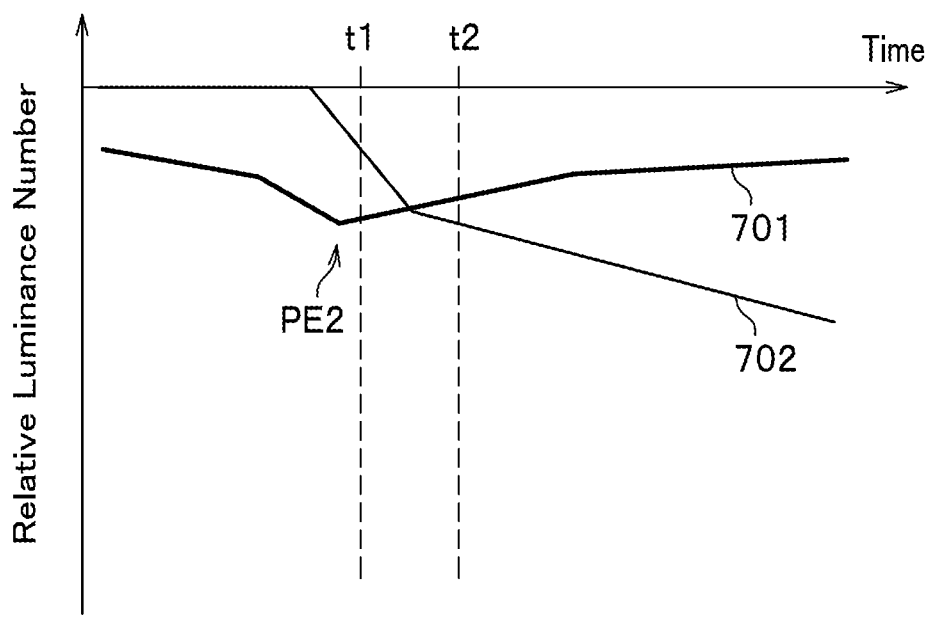
FIG. 46 is a diagram (part 2) illustrating a time variation of the relative luminance number in the second quality control area and the chemotaxis assay area.

FIG. 46 is a diagram illustrating a time variation of the relative luminance number in the second quality control area and the chemotaxis assay area.

Note that, in FIG. 46, the relative luminance number is indicated by a negative value so as to show the repellent side.

Herein, the second quality control area 502 of interest is the repellent side quality control area 502b. The chemotaxis assay area 503 of interest is the repellent chemotaxis assay area 503b.

A reference numeral 701 represents a time variation of the relative luminance number in the repellent side quality control area 502b. A reference numeral 702 represents a time variation of the relative luminance number in the repellent chemotaxis assay area 503b.

Note that the relative luminance numbers of the reference numeral 701 corresponds to "Area of interest"="Repellent side quality control area 502b" in formula (7). The relative luminance numbers on the reference numeral 702 corresponds to "Area of interest"="Repellent chemotaxis assay area 503b" in formula (7).

A graph of the reference numeral 701: shows a peak PE2 just before time t2; and is gradually increased. A graph of the reference numeral 702 keeps on moving upward from time 0 (at the start of the chemotaxis) to time t2 (t2>t1); and is then continued to decrease, though a rate of decrease becomes lower.

This is because the nematodes pass through the repellent side quality control area 502b and reach the repellent chemotaxis assay area 503b.

Note that t1=5 minutes and t2=10 minutes according to experiments carried out by the inventors.

As described above, in the fifth embodiment, firstly, if the luminance numbers in the first quality control area 501 become approximately 0 within a prescribed period of time, the state of the nematodes is determined to be in good condition. This makes it possible to confirm that the plotted nematodes do not keep on staying around the plotted point SP1.

After the above-described first quality control processing, if the luminance numbers in the second quality control area 502 show a peak within a prescribed time, the state of the nematodes is determined to be in good condition. This makes it possible to confirm that the nematodes are migrating on the repellent side, in addition to the migration away from the plotted point within the prescribed time as a result of the first quality control processing.

Thus, there is no problem in that a chemotaxis assay index is calculated at time t1 in FIG. 46. Note that the chemotaxis assay index is indicated by the relative luminance numbers in the repellent side chemotaxis assay area 503b at time t1.

(Actual Data; First Quality Control Area)

Figure 47:
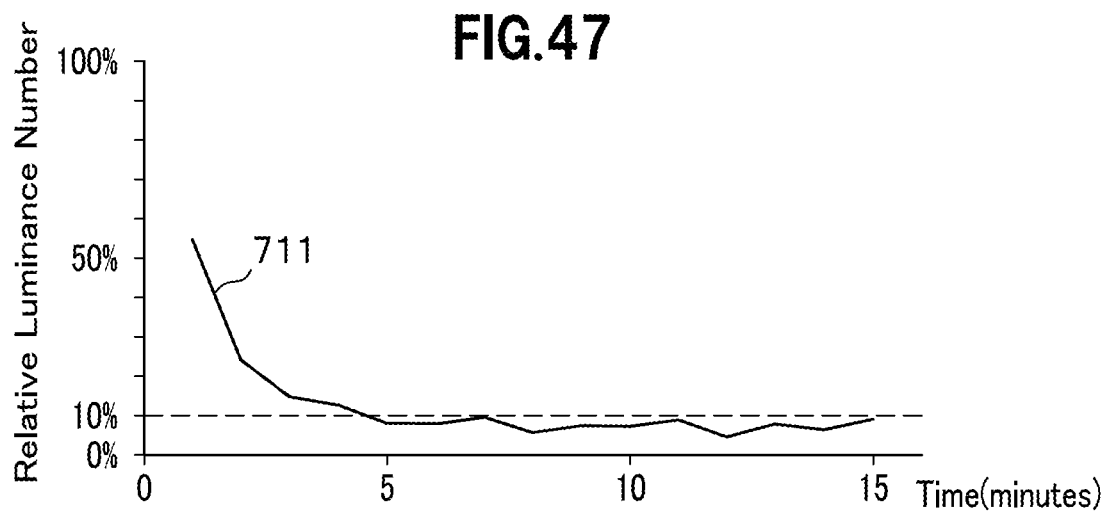
FIG. 47 is a diagram illustrating a time variation of the relative luminance number in the first quality control area, using a urine sample of a healthy subject based on actual data.

FIG. 47 is a diagram illustrating a time variation of the relative luminance number in the first quality control area, using a urine sample of a healthy subject based on actual data.

Figure 48:
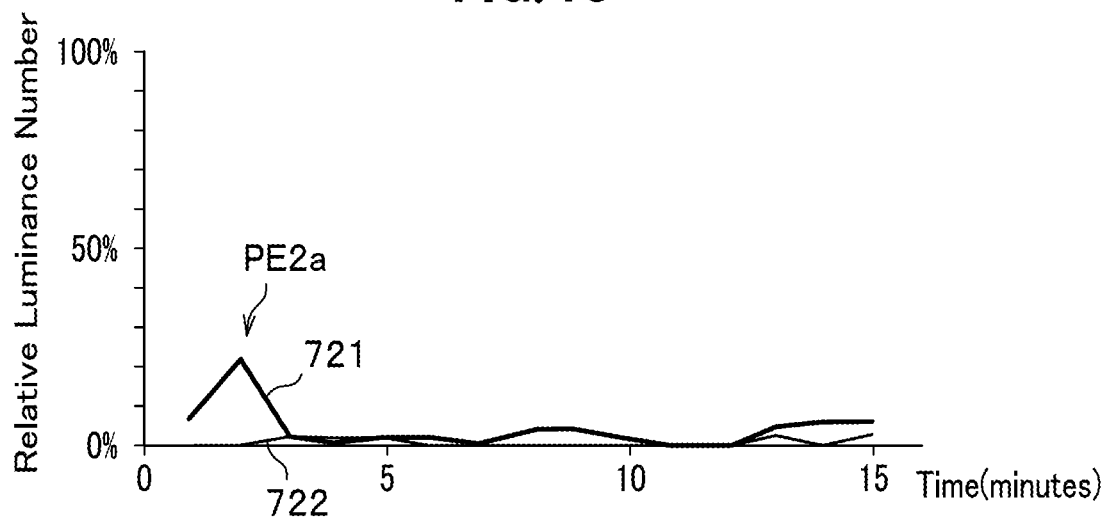
FIG. 48 is a diagram illustrating a time variation of the relative luminance number in the attractant side quality control area and the attractant side chemotaxis assay area, using the urine sample of the healthy subject based on actual data.
Figure 49:
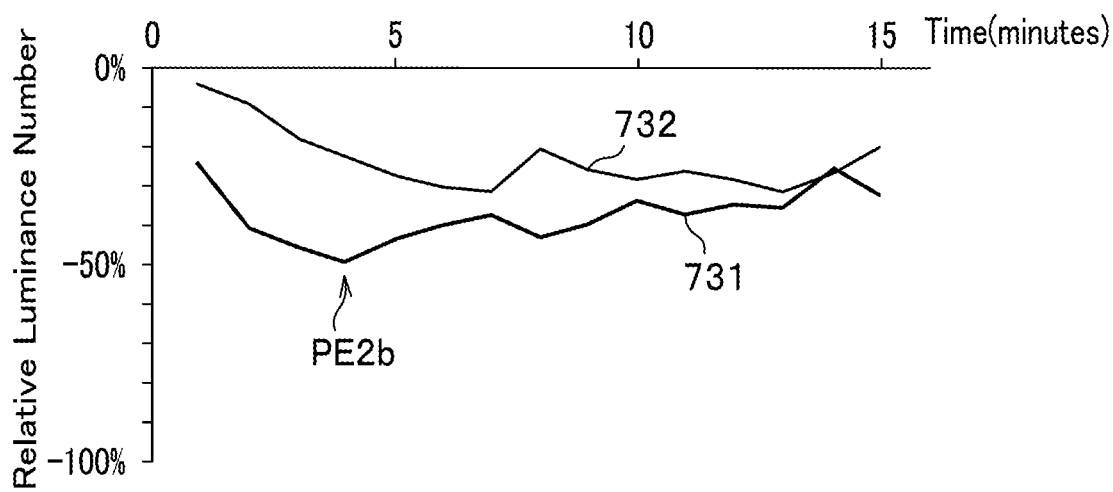
FIG. 49 is a diagram illustrating a time variation of the relative luminance number in the repellent side quality control area and the repellent side chemotaxis assay area, using the urine sample of the healthy subject based on actual data.

Note that a graph illustrated in each of FIG. 47 to FIG. 49 shows a test result using the urine sample of the healthy subject.

In each of FIG. 47 to FIG. 49, a vertical axis represents a relative luminance number, and a horizontal axis represents a time (minute).

As shown in a graph 711 in FIG. 47, the relative luminance number is decreased to a 10% after 5 minutes from a start of measurement (at a time of 0 minutes). This makes it possible to determine that a state of the nematodes used is in good condition.

(Actual Data: Attractant Side Quality Control Area and Attractant Side Chemotaxis Assay Area)

FIG. 48 is a diagram illustrating a time variation of the relative luminance number in the attractant side quality control area and the attractant side chemotaxis assay area, using the urine sample of the healthy subject based on actual data.

A graph 721 shows a time variation of the relative luminance number in the attractant side quality control area 502a when the urine sample of the healthy subject is used. Similarly, a graph 722 shows a time variation of the relative luminance number in the attractant side chemotaxis assay area 503a when the urine sample of the healthy subject is used.

In the graph 721, a peak PE2 appears within 5 minutes after the start of measurement (at time 0). The peak PE2 is, however, observed within a certain time width only, and is therefore determined as noise. That is, the graph 721 shows low values other than the peak PE2a. If a peak is not noise, as shown in the graph 621 of FIG. 43, the relative luminance numbers at both sides of the peak should take substantial values.

In the graph 722, the relative luminance numbers are basically 0. The peak PE2 described above is determined as noise also by the fact that no rise is seen in the relative luminance numbers (in the graph 722) in the attractant side chemotaxis assay area 503a.

(Actual Data: Repellent Side Quality Control Area and Repellent Side Chemotaxis Assay Area)

FIG. 49 is a diagram illustrating a time variation of the relative luminance number in the repellent side quality control area and the repellent side chemotaxis assay area, using the urine sample of the healthy subject based on actual data.

A graph 731 shows a time variation of the relative luminance number in the repellent side quality control area 502b, using the urine sample of the healthy subject. Similarly, a graph 732 shows a time variation of the relative luminance number in the repellent chemotaxis assay area 503b, using the urine sample of the healthy subject.

Note that, in FIG. 49, the relative luminance number is indicated by a negative value so as to show the repellent side.

In FIG. 49, in the graph 731, a peak PE2b appears within 5 minutes after the start of measurement (at time 0). In the graph 731, after the peak PE2b, the relative luminance number is increased.

In the graph 732, the relative luminance number: is decreased from the start of measurement (at time 0) till approximately 7 minutes; is basically leveled off; and is slightly increased after approximately 13 minutes.

Thus, it can be confirmed that the nematodes have passed through the repellent side quality control area 502*b* and reach the repellent chemotaxis assay area 503*b*.

[Control Test]

Figure 50:
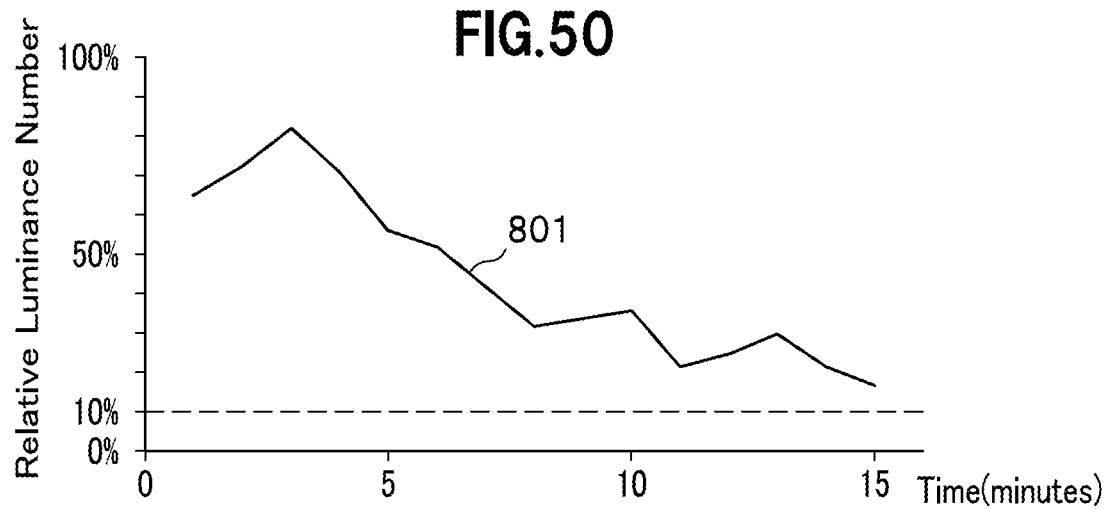
FIG. 50 is a diagram illustrating a time variation of the relative luminance number in the first quality control area using distilled water based on actual data.
Figure 51:
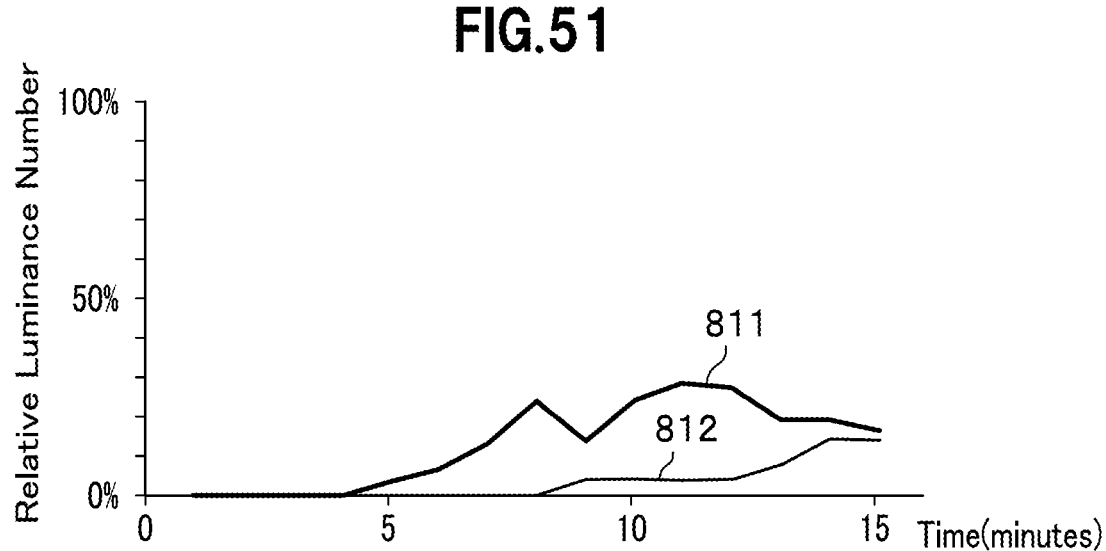
FIG. 51 is a diagram illustrating a time variation of the relative luminance number in the attractant side quality control area and the attractant side chemotaxis assay area, using distilled water based on actual data.
Figure 52:
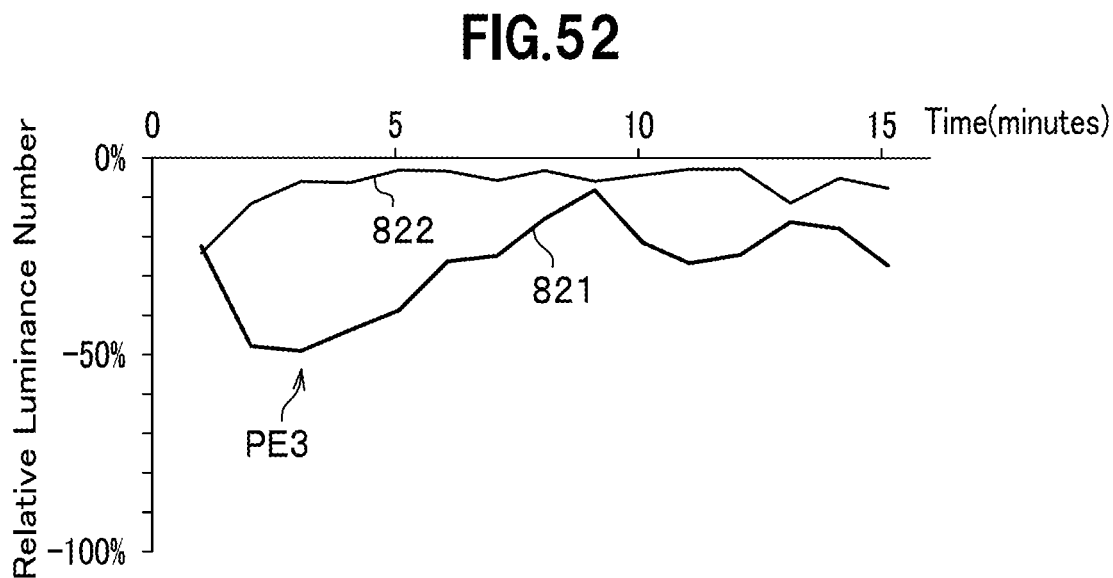
FIG. 52 is a diagram illustrating a time variation of the relative luminance number in the repellent side quality control area and the repellent side chemotaxis assay area using distilled water based on actual data.

Next is described a test result of a control test using distilled water in place of a urine sample, with reference to FIG. 50 to FIG. 52. That is, a state of nematodes in a pseudo poor condition is created by using the distilled water in place of the urine sample.

(Actual Data; First Quality Control Area)

FIG. 50 is a diagram illustrating a time variation of the relative luminance number in the first quality control area using distilled water based on actual data.

Note that, in FIG. 50 to FIG. 52, a vertical axis represents a relative luminance number, and a horizontal axis represents a time (minute).

As illustrated in FIG. 50, a graph 801 on the relative luminance number shows that the relative luminance number is not decreased to 10% or less even after 15 minutes from the start of measurement (at time 0). This shows that the nematodes keep on staying around the plotted point SP1.

(Actual Data: Attractant Side Quality Control Area and Attractant Side Chemotaxis Assay Area)

FIG. 51 is a diagram illustrating a time variation of the relative luminance number in the attractant side quality control area and the attractant side chemotaxis assay area, using distilled water based on actual data.

A graph 811 shows a time variation of the relative luminance number in the attractant side quality control area 502*a* using distilled water. Similarly, a graph 812 shows a time variation of the relative luminance number in the attractant side chemotaxis assay area 503*a* using distilled water.

As illustrated in FIG. 51, in the graph 811, no peak appears within 5 minutes from the start of measurement (at time 0).

The graph 812 shows a value 0 until approximately 8 minutes from the start of measurement (at time 0) and, after that, shows a low rise rate.

It can be therefore confirmed that not so many nematodes have migrated to the attractant side.

(Actual Data: Repellent Side Quality Control Area and Repellent Side Chemotaxis Assay Area)

FIG. 52 is a diagram illustrating a time variation of the relative luminance number in the repellent side quality control area and the repellent side chemotaxis assay area using distilled water based on actual data.

A graph 821 shows a time variation of the relative luminance number in the repellent side quality control area 502*b* when distilled water is used. Similarly, a graph 822 shows a time variation of the relative luminance number in the repellent chemotaxis assay area 503*b* when distilled water is used.

Note that, in FIG. 52, the relative luminance number is indicated by a negative value so as to show the repellent side.

In the graph 821, a peak PE3 appears within 5 minutes from the start of measurement (at time 0). The peak PE3 can be, however, determined as noise, because the graph 822 shows no decrease after the peak PE3.

In the first place, however, such a sample is discarded when subjected to the first quality determination processing, as illustrated in FIG. 50, because the relative luminance number in the first quality control area 501 has not decreased to 10% or less within 5 minutes.

FIG. 52 also shows that not so many nematodes have migrated to the repellent side.

<Integrated Value>

A time integrated value (a cumulative addition value) of the relative luminance numbers in a prescribed duration is also used as a chemotaxis index. An integration time is 0 to 5 minutes or 0 to 10 minutes after a start of measurement.

FIG. 53 and FIG. 54 are each a table showing an example of relative luminance numbers without integration and relative luminance numbers with integration (cumulative addition) of relative luminance numbers (integrated values) every one minute. Note that an addition of luminance numbers is used for obtaining the relative luminance numbers.

FIG. 53 shows a case of attraction (when a urine sample of a cancer patient is used), and FIG. 54 shows a case of repellent (when a urine sample of a healthy subject is used). Each of FIG. 53 and FIG. 54 shows respective relative luminance numbers after 5 minutes and after 10 minutes from the start of measurement. Each of FIG. 53 and FIG. 54 further shows time integrated values (integrated values) of the relative luminance numbers for 5 minutes (in FIG. 53 and FIG. 54, described as 5 minutes) and for 10 minutes (in FIG. 53 and FIG. 54, described as 10 minutes) from the start of measurement.

As illustrated in FIG. 53, by integrating the relative luminance numbers, noise component can be reduced. This makes it possible to improve accuracy.

As another calculation of a chemotaxis index, firstly, respective chemotaxis indexes in the attractant side chemotaxis assay area 503*a* and in the repellent chemotaxis assay area 503*b* are calculated. The two indexes are then added, and the addition result can be used as a new chemotaxis index. At this time, the attractant side takes a sign "+"; and, the repellent side, "−". For example, let us assume that a chemotaxis index (relative luminance numbers) in the attractant side chemotaxis assay area 503*a* is "+10", and a chemotaxis index (relative luminance numbers) in the repellent chemotaxis assay area 503*b* is "−2" in a test. In this case, +10+(−2)=+8 is taken as a final chemotaxis index.

By using the above technique, even if whether a taxis is attractant or repellent is not clear, an appropriate determination can be made. The case in which a taxis is attractant or repellent is not clear is, for example, when a chemotaxis index in the attractant side chemotaxis assay area 503*a* is "+10" and a chemotaxis index in the repellent chemotaxis assay area 503*b* is "−8". In this case, +10+(−8)=+2 is taken as a final chemotaxis index (attractant). As described above, even when it is seemingly difficult to determine whether a taxis is attractant or repellent, an appropriate determination on attraction or repellent can be made.

In the fifth embodiment, a chemotaxis assay is performed after a quality control, which allows a one-hundred percent test of a state of nematodes. The quality control herein is performed based on a state of movement of nematodes when a test is conducted, which allows a solid quality control to be achieved. This makes it possible to improve reliability of the test. Also, it is not herein required to perform a chemotaxis assay of the plate P inappropriate for a test (an image analysis), which allows an efficient image analysis to be performed.

The quality control is herein performed based on a time variation of luminances, which can reduce load on a tester or a processing, compared to a technique of counting the number of nematodes. For example, in the technique of counting the number of nematodes, when it is difficult to discriminate the nematodes one by one in such a case that the nematodes lay on top of each other or the like, counting is prone to be arbitrary. As described in the fifth embodiment, when a quality control is performed based on a time variation of luminances, a quality control of nematodes can be performed based on an objective index.

In the fifth embodiment, the first quality determination processing unit 114 determines how much relative luminance numbers in a prescribed area (the first quality control area 501) containing the nematode-plotted point SP1 is decreased. This makes it possible to determine whether or not the nematodes have migrated from the plotted point SP1.

In the fifth embodiment, when relative luminance numbers in the first quality control area 501 take a value equal to or less than a prescribed value (in the fifth embodiment, 10%), nematodes are determined to be in good condition (a quality of the nematodes is guaranteed). This makes it possible to know whether or not the nematodes have no difficulties in migrating from the plotted point SP1.

In the fifth embodiment, a quality control is performed depending on whether or not any peak appears in the attractant side quality control area 502a and the repellent side quality control area 502b within a prescribed period. This makes it possible to know whether or not the nematodes have passed the attractant side or the repellent side or whether or not the nematodes are properly migrating on the attractant side or on the repellent side.

In the fifth embodiment, after the first quality determination processing, the second quality determination processing is performed. Thus, after whether or not nematodes have migrated from the plotted point SP1 is determined, whether or not the nematodes are migrated toward the attractant side or the repellent side can be determined. This makes it possible to improve accuracy of the quality control.

In the fifth embodiment, the relative luminance is used as the luminance, in place of the luminous center of gravity in the first to the fourth embodiments. This makes it possible to obtain a clearer test result.

As described above, a luminance number of the relative luminance number is basically obtained by adding up luminance numbers. The luminance number used herein is the number of white pixels obtained by binarizing an image. This makes it possible to reduce load on processing.

In the fifth embodiment, a relative luminance number is used as a chemotaxis index. This makes it possible to obtain a clearer test result based on a luminous center of gravity thereof, compared to that in the first to the fourth embodiments.

A chemotaxis assay is herein performed, after a prescribed time has passed for obtaining a result of the first quality control or the second quality control (a second time). This can make a time required for the test shorter. Further, the shorter time required for the test makes it possible to complete the test before a specimen used is diffused.

A width of the second quality control area 502 illustrated in FIG. 36 or a width of the chemotaxis assay area 503 in the upward or the downward direction with respect to the plane may be made smaller. This makes it possible to improve accuracy in whether or not nematodes are migrating toward the attractant side or the repellent side.

It is possible to perform only the first quality control processing or only the second quality control processing.

Note that the first quality determination processing unit 114 determines whether or not the relative luminance number takes a prescribed value (for example, 10%) within a prescribed time (for example, 5 minutes). Not limited to this, however, whether or not a time variation rate of the relative luminance number in the first quality control area 501 takes a prescribed value or less may be determined.

In the fifth embodiment, relative luminance is used as a chemotaxis index. Any other index may be, however, used as the chemotaxis index.

The present invention is carried out not only by the above-described embodiments but also by variations of many types. For example, the above-described embodiments are intended to be illustrative of the present invention in an easily understandable manner, and the present invention is not limited to the one that includes all of the components explained in the embodiment. Part of a configuration of an embodiment of the present invention can be substituted by or added to that of another embodiment. Part of a configuration of an embodiment can be deleted.

Part or all of a configuration, a function, the units 100 to 109 and 111 to 118, the storage device 13, the database 3, or the like can be realized by hardware by means of, for example, designing of integrated circuits. As illustrated in FIG. 2, FIG. 12, FIG. 20, FIG. 30, and FIG. 35, the above-described configuration, function, or the like can be embodied by software in which, for example, a processor such as the CPU 12 interprets and executes a program which realizes the function. As illustrated in FIG. 2, FIG. 12, FIG. 20, FIG. 30, and FIG. 35, data in a program, a table, a file, and the like for realizing such a function can be stored in the storage device 13 including the memory 11, a hard disk, and a SSD (Solid State Drive) or in a storage medium including an IC (Integrated Circuit) card, a SD (Secure Digital) card, and a DVD (Digital Versatile Disc).

In the embodiments, only a control line or an information line which are deemed necessary for explanation is illustrated, and not all of them which are necessary in a product are illustrated. In practice, almost all configurations are deemed to be connected to each other.

DESCRIPTION OF REFERENCE NUMERALS 1, 1a-1d analyzer (analysis unit)
2 photographing apparatus (photographing unit)
100, 100a to 100c processing unit
101, 111 image acquisition unit
102, 112 pixel coupling unit
103, 113 luminance information acquisition unit
104 luminous center of gravity calculation unit
105 chemotaxis index calculation unit
106 test result determination unit
107 pixel removal unit
108 photographing stop determination processing unit
109 plate removal processing unit
114 first quality determination processing unit (quality control unit)
115 second quality determination processing unit (quality control unit)
116 chemotaxis index calculation unit
117 noise determination processing unit
118 storage processing unit
201 base unit
202 light source unit
203 seat
204 first support member
205 second support member
206 camera (photographing unit)
221 diffuser-panel-attached ring LED light source
222 douser
231 imaging lens
232 image pickup device
233 front focus
241 diffuser panel 301 center of a coupled image
302 dashed circle
401, 411 point of origin (luminous center of gravity immediately after plotting)
402, 412 point at which behavior of nematodes is slowed down
501 first quality control area (prescribed range, prescribed area)
501 second quality control area (prescribed range)
501a attractant side quality control area (prescribed range)
502b repellent side quality control area (prescribed range)
503 chemotaxis assay area
503a attractant side chemotaxis assay area
503b repellent side chemotaxis assay area
E, E1 to E3 nematodes
P plate
Pz culture plate
Pa to Pc analysis plate
SP1 point in which nematodes are plotted
SP2 point in which urine sample is plotted
t1 time (first time, second time)
Z, Zd cancer analysis system

The invention claimed is:

1. A cancer analysis system, comprising:
a plate on which nematodes and a urine sample are placed;
a light source for irradiating light toward the plate;
a photographing device for taking an image of the nematodes on the plate irradiated by the light from the light source, the taken image having a prescribed area;
a memory for storing a program; and
a processor programmed to execute the program so as to:
   determine a taxis speed of the nematodes based on the taken image; and
   calculate a chemotaxis index based on the taken image when the processor determines that the taxis speed of the nematodes meets a predetermined condition, the chemotaxis index representing a taxis of the nematodes,
wherein the prescribed area corresponds to an area in which the nematodes are placed on the plate that is taken by the photographing device;
the predetermined condition includes a state in which a relative luminance number decreases to 10% during a first period of time from a start of measurement to a first prescribed time,
the relative luminance number is calculated by dividing a sum of first luminance numbers in the prescribed area in the taken image by a sum of second luminance numbers in an entirety of the taken image, and
the first period of time is within five minutes.

2. The cancer analysis system according to claim 1,
wherein the prescribed area includes:
   a urine area corresponds to an area in which the urine sample is placed on the plate;
   an attraction area that is located between a center line of the taken image and the urine area; and
   an avoidance area that is located in an area that is in line symmetry with the attraction area with respect to the center line of the taken image; and
when the processor is programmed to determine that a peak of a time variation in luminance in one of the attraction area or the avoidance area exists during a second period of time from the start of measurement to a second prescribed time, the processor programmed to determine that the predetermined condition is met.

3. The cancer analysis system according to claim 2,
wherein the processor is programmed to calculate the chemotaxis index when the second period of time passes.

4. The cancer analysis system according to claim 1,
wherein the processor is further programmed to:
   calculate the second luminance numbers which are obtained by adding up luminances in subranges constituting the entirety of the taken image; and
   calculate the first luminance numbers which are obtained by adding up luminances in the subranges in the prescribed area.

5. The cancer analysis system according to claim 1,
wherein the processor is further programmed to:
   calculate a number of a total white pixel which is obtained by adding up numbers of white pixels in the entirety of the taken image to obtain the sum of the second luminance numbers, the white pixel being a pixel created by a binarization processing of the taken image;
   calculate a number of an area white pixel which is obtained by adding up numbers of the white pixels in the prescribed area to obtain the sum of the first luminance numbers; and
   divide the number of the area white pixel by the number of the total white pixel, to thereby obtain the relative luminance number.

6. The cancer analysis system according to claim 4,
wherein the chemotaxis index is the relative luminance number in either an attraction area in the prescribed area or an avoidance area in the prescribed area,
the attraction area has a urine area corresponding to an area in which the urine sample is placed on the plate, and
the avoidance area is located in an area that is in line symmetry with the attraction area with respect to a center line of the taken image.

7. The cancer analysis system according to claim 4,
wherein the relative luminance number is cumulatively added during a prescribed period of time.

* * * * *